(12) United States Patent
Gao et al.

(10) Patent No.: US 11,268,159 B2
(45) Date of Patent: *Mar. 8, 2022

(54) COMPOSITIONS AND METHOD FOR DETECTING HEPATITIS A VIRUS NUCLEIC ACIDS IN SINGLE-PLEX OR MULTIPLEX ASSAYS

(71) Applicant: GEN-PROBE INCORPORATED, San Diego, CA (US)

(72) Inventors: Kui Gao, San Diego, CA (US); Jeffrey M. Linnen, Poway, CA (US); Kurt C. Norton, La Mesa, CA (US); Patricia C. Gordon, Spring Valley, CA (US); Dat Do, San Diego, CA (US); Tan N. Le, La Mesa, CA (US)

(73) Assignee: Gen-Probe Incorporated, San Diego, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 15/618,598

(22) Filed: Jun. 9, 2017

(65) Prior Publication Data

US 2018/0057895 A1    Mar. 1, 2018

Related U.S. Application Data

(62) Division of application No. 14/232,874, filed as application No. PCT/US2012/046630 on Jul. 13, 2012, now Pat. No. 9,752,201.

(60) Provisional application No. 61/508,597, filed on Jul. 15, 2011.

(51) Int. Cl.
*C12Q 1/70* (2006.01)

(52) U.S. Cl.
CPC .............. *C12Q 1/706* (2013.01); *C12Q 1/701* (2013.01); *C12Q 2600/16* (2013.01); *Y02A 50/30* (2018.01)

(58) Field of Classification Search
CPC .... C12Q 1/701; C12Q 1/706; C12Q 2600/16; Y02A 50/54
See application file for complete search history.

(56) References Cited

U.S. PATENT DOCUMENTS

| | | |
|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,868,105 A | 9/1989 | Urdea et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold, Jr. et al. |
| 5,312,728 A | 5/1994 | Lizardi et al. |
| 5,378,825 A | 1/1995 | Cook et al. |
| 5,399,491 A | 3/1995 | Kacian et al. |
| 5,422,252 A | 6/1995 | Walker et al. |
| 5,437,990 A | 8/1995 | Burg et al. |
| 5,449,608 A | 9/1995 | Young et al. |
| 5,547,842 A | 8/1996 | Hogan et al. |
| 5,554,516 A | 9/1996 | Kacian et al. |
| 5,585,481 A | 12/1996 | Arnold, Jr. et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 6,110,678 A | 8/2000 | Weisburg et al. |
| 6,274,307 B1 | 8/2001 | Soutschek et al. |
| 6,280,952 B1 | 8/2001 | Weisburg et al. |
| 6,361,945 B1 | 3/2002 | Becker et al. |
| 6,649,339 B1 | 11/2003 | Zerlauth et al. |
| 6,949,367 B1 | 9/2005 | Dempcy et al. |
| 7,094,541 B2 | 8/2006 | Brentano et al. |
| 7,291,452 B1 | 11/2007 | Nguyen et al. |
| 8,105,610 B2 | 1/2012 | Nguyen et al. |
| 2003/0124578 A1 | 7/2003 | Brentano et al. |
| 2003/0170612 A1 | 9/2003 | Pichuantes et al. |
| 2005/0221300 A1 | 10/2005 | Pichuantes et al. |
| 2006/0014142 A1 | 1/2006 | Carlson et al. |
| 2006/0057643 A1 | 3/2006 | McCarthy et al. |
| 2006/0068417 A1 | 3/2006 | Becker et al. |
| 2009/0208968 A1* | 8/2009 | Carlson ................ C12Q 1/6865 435/5 |
| 2011/0306038 A1 | 12/2011 | Carrick |

FOREIGN PATENT DOCUMENTS

| | | |
|---|---|---|
| DE | 102006034844 B3 | 12/2007 |
| EP | 0320308 | 11/1993 |
| EP | 0569237 | 11/1993 |

(Continued)

OTHER PUBLICATIONS

Buck, G.A. et al., Design Strategies and Performance of Custom DNA Sequencing Primers, Biotechniques, vol. 27, pp. 528-536 (Year: 1999).*
Gen Bank Accession No. AB020564, Hepatitis A virus genomic RNA, complete sequence, isolate AH1, pp. 1-3 (Year: 2001).*
EPO Communication Pursuant to Article 94(3) EPC, European Patent Application No. 12737458.5, dated Dec. 20, 2017.
APO Examination Report No. 1, Australian Patent Application No. 2016244315, dated Feb. 22, 2018.
JPO Penultimate Official Action, Japanese Patent Application No. 2016-104894, dated Mar. 9, 2018.

(Continued)

*Primary Examiner* — Teresa E Strzelecka
(74) *Attorney, Agent, or Firm* — Knobbe Martens Olson & Bear, LLP

(57) ABSTRACT

Nucleic acid oligomers specific for human parvovirus genomic DNA are disclosed. An assay for amplifying and detecting human parvovirus genotypes 1, 2 and 3 nucleic acid in biological specimens is disclosed. Compositions for amplifying and detecting the presence of human parvovirus genotypes 1, 2 and 3 genomic DNA in human biological specimens are disclosed.

23 Claims, No Drawings

Specification includes a Sequence Listing.

(56) References Cited

FOREIGN PATENT DOCUMENTS

| | | |
|---|---|---|
| EP | 0747706 | 12/1996 |
| JP | 2008506392 A | 3/2008 |
| WO | WO 1988/001302 | 2/1988 |
| WO | WO 1988/010315 | 12/1988 |
| WO | WO 1990/014439 | 11/1990 |
| WO | WO 1993/022461 | 11/1993 |
| WO | WO 1994/003472 | 2/1994 |
| WO | WO 1995/003430 | 2/1995 |
| WO | WO 1995/032305 | 11/1995 |
| WO | WO 1996/009391 | 3/1996 |
| WO | WO 1996/027799 | 9/1996 |
| WO | WO 1999/013121 | 3/1999 |
| WO | 01/14593 A2 | 3/2001 |
| WO | WO 2003/002753 | 1/2003 |
| WO | WO 2003/020742 | 3/2003 |
| WO | WO 2006/007603 | 1/2006 |
| WO | 2006031608 A2 | 3/2006 |
| WO | WO 2008/016988 | 2/2008 |
| WO | WO 2008/089193 | 7/2008 |
| WO | 2009131728 A2 | 10/2009 |
| WO | 2010/099378 A2 | 9/2010 |

OTHER PUBLICATIONS

PCT International Preliminary Report on Patentability International Application No. PCT/US2012/046630, dated Jan. 21, 2014.
PCT International Search Report & Written Opinion,, International Application No. PCT/US2012/046630, dated Oct. 2, 2012.
EPO Extended European Search Report, European Patent Application No. 15193844.6, dated Feb. 26, 2016.
EPO Communication pursuant to Article 94(3) EPC, European Patent Application No. 15193844.6, dated May 24, 2017.
Gao et al., "A Duplex Transcription-Mediated Amplification Assay for the Simultaneous Quantitation of Parvovirus B19 DNA and Qualitative Detection of Hepatitis A Virus RNA on a Fully Automated Instrument System," International Society of Blood Transfusion, Vox Sanguinis, 2011.
Linnen et al., "Performance Characteristics of the Procleix Parvo/HAV Assay on the Procleix Trigris System, A Duplex Assay for Quantitative Detection of Parvovirus B19 and Qualitative Detection of Hepatitis A Virus," International Society of Blood Transfusion, Vox Sanguinis, 2012.
Pichl et al., "Performance of the Roche Cobas (R) Taqscreen DPX Test for B19 and HAV in a Blood Transfusion Service," International Society of Blood Transfusion, Vox Sanguinis, 2010.
Wessberg et al., "Finish Red Cross Evaluation of the Roche Cobas Taqscreen DPX Test for Simultaneous Detection and Quantitation of Human Parvovirus B19 and Detection of Hepatitis A Virus," International Society of Blood Transfusion, Vox Sanguinis, 2010.
EPO extended European search report, European Patent Application No. 19164993.8, dated May 28, 2019.
Abraham et al., "Nucleobase analogs for degenerate hybridization devised through conformational pairing analysis", BioTechniques, (2007), vol. 43, pp. 617-624.
Adams et al., "The Biochemistry of the Nucleic Acids", Chapman & Hall, Eleventh Edition, pp. 5-39, 1992.
Arnold et al., "Assay Formats Involving Acridinium-Ester-Labeled DNA Probes", Clin. Chem., (1989), vol. 35, pp. 1588-1594.
Brown et al., "Parvovirus B19 in Human Disease", Annu. Rev. Med., (1997), vol. 48, pp. 59-67.
Dato et al., "Hepatitis A Outbreak Associated with Green Onions at a Restaurant—Monaca, Pennsylvania, 2003", Morbidity Mortality Wkly. Rpt., (2003), vol. 52, No. 47, pp. 1155-1157.
Ekman et al., "Biological and Immunological Relations among Human Parvovirus B19 Genotypes 1 to 3", J. Virol., (2007), vol. 81, No. 13, pp. 6927-6935.
Laporte et al., "Foodborne Transmission of Hepatitis A—Massachusetts, 2001", Morbidity Mortality Wkly. Rpt., (2003), vol. 52, No. 24, pp. 565-567.
Mullis et al., "Specific Synthesis of DNA in Vitro via Polymerase-Catalyzed Chain Reaction" Methods in Enzymology, (1987), vol. 155, pp. 335-350.
Servant et al., "Genetic Diversity within Human Erythroviruses: Identification of Three Genotypes" J. Virol., (2002), vol. 76, No. 18, pp. 9124-9134.
Shade et al., "Nucleotide Sequence and Genome Organization of Human Parvovirus B19 Isolated from the Serum of a Child during Aplastic Crisis", J. Virol., (1986), vol. 58, No. 3, pp. 921-936.
Vester et al., "LNA (Locked Nucleic Acid): High-Affinity Targeting of Complementary RNA and DNA", Biochemistry, (2004), vol. 43, pp. 13233-13241.
International Search Report and Written Opinion in International Application No. PCT/US2012/046630, dated Feb. 10, 2012.
APO, Patent Examination Report No. 1, Australian Patent Application No. 2012284307, dated Jan. 16, 2015.
APO, Patent Examination Report No. 1, Australian Patent Application No. 2012284307, dated Jun. 24, 2016.
EPO, Communication Pursuant to Article 94(3), European Patent Application No. 12737458.5, dated Mar. 30, 2015.
EPO, Communication Pursuant To Article 94(3), European Patent Application No. 12737458.5, dated Mar. 24, 2016.
SIPO, Third Office Action, Chinese Patent Application No. 201280035195.2, dated Jun. 24, 2016.
SIPO, Second Office Action, Chinese Patent Application No. 201280035195.2, dated Oct. 22, 2015.
SIPO, Search Report, Chinese Patent Application No. 201280035195.2, dated Dec. 29, 2014.
SIPO, First Office Action, Chinese Patent Application No. 201280035195.2, dated Dec. 29, 2014.
JPO, Office Action, Japanese Patent Application No. 2014-520358, dated Apr. 11, 2016.
JPO, Office Action, Japanese Patent Application No. 2014-520358, dated Sep. 30, 2016.

* cited by examiner

COMPOSITIONS AND METHOD FOR DETECTING HEPATITIS A VIRUS NUCLEIC ACIDS IN SINGLE-PLEX OR MULTIPLEX ASSAYS

CROSS-REFERENCE TO RELATED APPLICATIONS

This application is a divisional application of U.S. Pat. No. 9,752,201, issued Sep. 5, 2017, which is the national stage entry under 35 U.S.C. § 371 of International App. No. PCT/US2012/046630, filed Jul. 13, 2012, which claims the benefit of priority under 35 U.S.C. § 119 to U.S. App. No. 61/508,597 filed on Jul. 15, 2011, the entire contents of each are incorporate herein by reference.

REFERENCE TO SEQUENCE LISTING

The instant application contains a Sequence Listing which has been submitted in ASCII format via EFS-Web and is hereby incorporated by reference in its entirety. Said ASCII Copy, created on Jun. 5, 2017, is named "GP274-03-DV1_ST25.txt" and is 59 KB in size.

FIELD

This invention relates to diagnostic methods and compositions for detecting a human infectious agent, and specifically relates to methods and compositions for detecting in vitro the nucleic acid of human parvovirus genotypes 1, 2 and 3 and/or hepatitis A virus.

BACKGROUND

A number of therapeutic proteins, including clotting factors, immunoglobulin (IVIG), and albumin, are purified from human plasma by companies like Grifols, Baxter, and CSL. It's important to test for parvovirus B19 and HAV because they are non-enveloped viruses, making these viruses resistant to inactivation during the purification (fractionation) process. Relatively low levels of B19 are allowed to exist is a plasma fraction (current regulations require less than 10,000 IU in a manufacturing pool which can contain 4,000 to 5,000 individual plasma units). Rather than taking the risk of assembling a large manufacturing pool and then finding out that it's contaminated with B19, plasma fractionators typically screen smaller pools to identify individual plasma units that contain high titers of B19. There are currently no regulations related to HAV but testing is generally performed because doing so has become an industry standard.

Human parvovirus (genus *Erythrovirus*) is a blood borne, non-enveloped virus that has a single-stranded DNA (ssDNA) genome of about 5.5 kb (Shade et al., 1986, *J. Virol.* 58(3): 921-936, Brown et al., 1997, *Ann. Rev. Med.* 48: 59-67). Individual virions contain one copy of either the plus or minus strand of the genome, represented in approximately equal numbers. The ssDNA genome has inverted terminal repeats that form 5' and 3' hairpins of about 350 nt, which are essential for viral replication. The genome includes two open reading frames on the plus strand, which code for structural proteins (VP1 and VP2) and non-structural protein (NS1).

At one time it was believed that human parvovirus was highly conserved at less than 2% genetic diversity. More recently, though, it has been discovered that a human *Erythrovirus* isolate, originally termed V9, has a greater than 11% divergence in genome sequence compared to B19, with the most striking DNA dissimilarity at >20%, observed within the p6 promoter region. The V9 isolate was determined to have a clinical presence of greater than 11%, as well. Now the human *Erythrovirus* group is divided into three distinct virus genotypes: genotype 1 (B19), genotype 2 (A6- and LaLi-like), and genotype 3 (V9-like). (Servant et al., 2002, *J. Virol.* 76(18): 9124-34; Ekman et al., 2007, *J. Virol.* 81(13): 6927-35). Servant et al., refer to genotype 1 as viruses corresponding to parvovirus B19 and refer to genotypes 2 and 3 as viruses corresponding to parvovirus V9-related. Ekman et al., refer to genotypes 1-3 as all corresponding to parvovirus B19. For convenience herein, genotypes 1, 2 and 3 are referred to as parvovirus genotypes 1, 2 and 3 or human parvovirus genotypes 1, 2 and 3. Nucleic acid detection assays that do not accurately detect all parvovirus genotypes result in many plasma pools remaining contaminated with human parvovirus. Thus, there is a need for a nucleic acid test that detects human parvovirus genotypes 1, 2 and 3.

Infection with human parvovirus can occur via respiratory transmission or through infected blood or blood products. Infected individuals may exhibit no symptoms, or have erythema infectiosum symptoms that include mild flu-like symptoms, rash ("fifth disease"), temporary arthritis-like joint pain (arthropathy), aplastic crisis in patients with hemolytic anemias, persistent parvovirus infection and loss of about 10% of early pregnancies due to fetal death. Thus, the failure to detect parvovirus in a pooled plasma sample or for diagnosis of infection has serious consequences.

Further, there is a need that detection assays provide a detection sensitivity that allows for detection of low titers of virus, as may occur early in an infection or in diluted or pooled samples. Parvovirus nucleic acid detection assays that can detect an appropriate level of contamination may facilitate removal of infected donated units from the blood supply or contaminated lots of pooled plasma before use.

Many immunodiagnostic methods detect anti-parvovirus antibodies (IgM or IgG) present in an individual's serum or plasma (e.g., see PCT Nos. WO 96/09391 by Wolf et al. and WO 96/27799 by Hedman et al.). These methods have limitations in detecting recent or current infections because they rely on detecting the body's response to the infectious agent. The rapid rise in viremia following infection results in high levels of parvovirus in an individual's blood without corresponding detectable levels of anti-parvovirus antibodies (See, e.g., U.S. Pat. No. 7,094,541 to Brentano et al at Example 4). Thus, immunological-based detection assays are susceptible to false negative results. Furthermore, viremia is often quickly cleared, yet a person may remain antibody-positive in the absence of these infective particles, thusly leading to false positive results. As many as 90% of adults are seropositive for parvovirus, making accurate immunological detection of recent or current infections difficult. Other similar assays detect the presence of parvovirus by detecting the virus or empty viral capsid bound to a purified cellular receptor (U.S. Pat. No. 5,449,608 to Young et al.), and these immuno-based assays experience similar problems.

DNA hybridization and amplification methods have also been used to detect human parvovirus, though these tests are generally directed to the detection of genotype 1 only. Yet, U.S. and European regulatory bodies have promulgated standards specifying that plasma pools used for manufacturing anti-D immunoglobulin and other plasma derivatives can contain no more than 10,000 IU/ml (10 IU/microliter in Europe) of any human parvovirus. As discussed above, therapeutic plasma pools and diagnostic tests need similarly to reliably identify human parvovirus types 1, 2 and 3. Thus, there is a need in the art for compositions, kits and methods useful in the in vitro nucleic acid detection of human parvovirus types 1, 2 and 3.

Hepatitis A virus (HAV) is the causative agent of one form of hepatitis that may produce symptoms that include fever, fatigue, nausea, abdominal pain, diarrhea, loss of appetite, and jaundice over less than two months. Of those infected with HAV, about 10% to 15% have a prolonged or relapsing symptoms over a six to nine months following infection Immunity to HAV, based on the individual's production of anti-HAV immunoglobulin G (IgG), follows both symptomatic and asymptomatic infections.

Although the incidence of HAV infections has dramatically decreased in parts of the world in which vaccination for HAV has been widely used since the late 1990's, epidemics of HAV infections (>700 cases per 100,000 population, and for children who live in areas with high rates of hepatitis A the rate increases to >20 cases per 100,000 population) may occur in non-immune populations where poor sanitary conditions exist, even temporarily, e.g. following an earthquake. Transmission may also result from contact with HAV-contaminated serum or blood products. Even in the USA, every year about 100 persons die from acute liver failure due to hepatitis A (death rate of about 0.015%). Even in nonfatal hepatitis A cases, substantial costs are associated with HAV infections, including those that result from patient hospitalization, outpatient visits, and lost work days.

HAV is a 27-nm RNA virus (a picornavirus) that contains a plus-sense single-stranded RNA genome of about 7.5 kb. The virus replicates in the liver, is excreted in bile, and is shed in feces (e.g., up to 108 virus per ml) during the acute phase of infection. The incubation period is usually two to six weeks before symptoms appear. A single serotype of HAV has been found worldwide. Diagnosis of hepatitis A cannot be differentiated from other types of viral hepatitis by symptoms or other clinical features (e.g., elevated serum aminotransferase levels). Typically, hepatitis A diagnosis is confirmed by serological testing that provides positive results for the presence of anti-HAV immunoglobulins (Ig). Anti-HAV IgM is generally present five to ten days before the onset of symptoms and is undetectable in most patients by six months later, whereas anti-HAV IgG appears early during infection and remains detectable for the individual's lifetime. HAV RNA can be detected in the blood and stool of most persons during the acute phase of infection by using nucleic acid testing methods, e.g., amplification by the polymerase chain reaction (PCR), and nucleic acid sequencing has been used to identify the genetic relatedness of HAV following community-wide infections (Dato et al., Morbidity Mortality Wkly. Rpt., 2003, 52(47): 1155-57; LaPorte et al., Morbidity Mortality Wkly. Rpt., 2003, 52(24): 565-67). These methods, however, are not generally used for diagnostic purposes.

Therefore, there exists a need to accurately detect the presence of HAV in the biological samples and environmental samples. There is also a need to detect the presence of HAV contamination in products that may be used in medical treatment (e.g., blood or serum for transfusions, or factors derived from human blood or serum). There is also a need to detect the presence of HAV in potentially contaminated materials, such as water or food, to prevent community-wide outbreaks or epidemics resulting from consumption of contaminated materials.

The inventions disclosed herein respond to those needs by describing oligonucleotide sequences that are used in nucleic acid testing methods to detect the presence of HAV nucleic acid (HAV RNA or sequences derived therefrom, e.g., cDNA). This application also describes nucleic acid testing methods that detect the presence of HAV RNA present in a sample.

SUMMARY

The present invention relates to compositions, kits and methods for the detection of hepatitis A virus and/or human parvovirus genotypes 1, 2 and 3. These compositions, kits and methods are configured to amplify target sequences of hepatitis A virus and/or human parvovirus nucleic acids and are configured to detect target sequences of Hepatitis A virus and/or human parvovirus nucleic acids or amplified nucleic acids. In certain embodiments and aspects, particular regions within target sequences of the hepatitis A virus and particular regions within the human parvovirus have been identified as preferred targets for nucleic acid amplification reactions of a sample, including biological specimens derived from infected humans, such as plasma samples. Amplification oligomers or detection oligomers targeting these regions may share common core sequences, and thus provide a plurality of particularly preferred amplification oligomers or detection oligomers. Amplification products generated using such particularly preferred amplification oligomers will contain target specific sequences useful for specific detection of human parvovirus or HAV from a sample. Detection of an amplification product can include any of a variety of methods, including, but not limited to, probe-based detection, hybridization protection assays, molecular torch, molecular beacon or molecular switch based assays, mass spectrometry, MALDI-TOF mass spectrometry, ESI-TOF mass spectrometry, real-time detection assays, gel-electrophoresis, SDS-PAGE electrophoresis, Sanger sequencing, Next Generation Sequencing and the like. These preferred regions of a target sequence provide improvements in relation to specificity, sensitivity, or speed of detection, and detection with high sensitivity. Using these amplification and/or detection oligomers, the methods include the steps of amplifying target sequences within human parvovirus genome or an HAV genome and detecting the amplification products. Detection oligomers are preferably used for detecting amplified products.

One embodiment is an oligomer combination for detecting at least one of a human parvovirus target nucleic acid and a hepatitis A virus (HAV) target nucleic acid in a sample, said oligomer combination comprising: (I) first and second amplification oligomers for amplifying a human parvovirus nucleic acid target region, wherein, (a) the first parvovirus amplification oligomer comprises a first target-hybridizing sequence that is from about 14 to about 27 contiguous nucleotides contained in the sequence of SEQ ID NO:181 and that includes at least the sequence of SEQ ID NO:117, SEQ ID NO:179 or SEQ ID NO:180; and (b) the second parvovirus amplification oligomer comprises a second target-hybridizing sequence selected from the group consisting of: (i) a sequence that is from about 14 to about 30 contiguous nucleotides contained in the sequence of SEQ ID NO:189 and that includes at least the sequence of SEQ ID NO:188; and (ii) a sequence that is from about 14 to about 30 contiguous nucleotides contained in the sequence of SEQ ID NO:193 and that includes at least the sequence of SEQ ID NO:192; and/or (II) first and second amplification oligomers for amplifying an HAV nucleic acid target region, wherein (a) the first HAV amplification oligomer comprises a first target-hybridizing sequence that is from about 14 to about 27 contiguous nucleotides contained in the sequence of SEQ ID NO:174 and that includes at least the sequence of SEQ ID NO:173; and (b) the second HAV amplification oligomer comprises a second target-hybridizing sequence that is from about 14 to about 30 contiguous nucleotides contained in the sequence of SEQ ID NO:177 and that includes at least the sequence of SEQ ID NO:175.

In one aspect, the oligomer combination comprises the first and second parvovirus amplification oligomers of (I). In one aspect, the first parvovirus target-hybridizing sequence of (I)(a) is contained in the sequence of SEQ ID NO:182 and includes at least the sequence of SEQ ID NO:179. In one aspect, the first parvovirus target-hybridizing sequence of (I)(a) includes at least the sequence of SEQ ID NO:183 or SEQ ID NO:117. In one aspect, the first target-hybridizing sequence of (I)(a) has a sequence selected from the group consisting of SEQ ID NOs:75-80. In one aspect, the first parvovirus target-hybridizing sequence of (I)(a) is contained in the sequence of SEQ ID NO:184. In one aspect, the first parvovirus target-hybridizing sequence of (I)(a) is selected from the group consisting of SEQ ID NOs:81-84. In one aspect, the first parvovirus target-hybridizing sequence of (I)(a) is contained in the sequence of SEQ ID NO:185 and includes at least the sequence of SEQ ID NO:180. In one aspect, the first parvovirus target-hybridizing sequence of (I)(a) is selected from the group consisting of SEQ ID NOs:82-84. In one aspect, the second parvovirus target-hybridizing sequence of (I)(b) is contained in the sequence of SEQ ID NO:187 and includes at least the sequence of SEQ ID NO:188. In one aspect, the second parvovirus target-hybridizing sequence of (I)(b) includes at least the sequence of SEQ ID NO:186. In one aspect, the second parvovirus target-hybridizing sequence of (I)(b) is selected from the group consisting of SEQ ID NOs:108-113. In one aspect, the second parvovirus target-hybridizing sequence of (I)(b) is contained in the sequence of SEQ ID NO:191. In one aspect, the second parvovirus target-hybridizing sequence of (I)(b) includes at least the sequence of SEQ ID NO:190. In one aspect, the second parvovirus target-hybridizing sequence of (I)(b) is selected from the group consisting of SEQ ID NOs:118-121. In one aspect, the second parvovirus amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second parvovirus amplification oligomer has a sequence selected from the group consisting of SEQ ID NO:88-93 and 98-101.

In one aspect, the oligomer combination described above, further comprises (III) third and fourth amplification oligomers for amplifying the human parvovirus nucleic acid target region, wherein: (a) the third parvovirus amplification oligomer comprises a third target-hybridizing sequence that is from about 14 to about 27 contiguous nucleotides contained in the sequence of SEQ ID NO:181 and that includes at least the sequence of SEQ ID NO:179 SEQ ID NO:117, or SEQ ID NO:180; and (b) the fourth parvovirus amplification oligomer comprises a fourth target-hybridizing sequence selected from the group consisting of (i) a sequence that is from about 14 to about 30 contiguous nucleotides contained in the sequence of SEQ ID NO:189 and that includes at least the sequence of SEQ ID NO:188; and (ii) a sequence that is from about 14 to about 30 contiguous nucleotides contained in the sequence of SEQ ID NO:193 and that includes at least the sequence of SEQ ID NO:192; wherein the third target-hybridizing sequence of (III)(a) is different from the first parvovirus target-hybridizing sequence of (I)(a); and wherein the fourth target-hybridizing sequence of (III)(b) is different from the second parvovirus target-hybridizing sequence of (I)(b).

In one aspect, the third parvovirus amplification oligomer is as above and the first parvovirus amplification oligomer is as set forth in the following: the first parvovirus target-hybridizing sequence of (I)(a) is contained in the sequence of SEQ ID NO:182 and includes at least the sequence of SEQ ID NO:179; the first parvovirus target-hybridizing sequence of (I)(a) includes at least the sequence of SEQ ID NO:117 or SEQ ID NO:183; the first target-hybridizing sequence of (I)(a) has a sequence selected from the group consisting of SEQ ID NOs:75-80; the first parvovirus target-hybridizing sequence of (I)(a) is contained in the sequence of SEQ ID NO:184; the first parvovirus target-hybridizing sequence of (I)(a) is selected from the group consisting of SEQ ID NOs:81-84; the first parvovirus target-hybridizing sequence of (I)(a) is contained in the sequence of SEQ ID NO:185 and includes at least the sequence of SEQ ID NO:180, or the first parvovirus target-hybridizing sequence of (I)(a) is selected from the group consisting of SEQ ID NOs:82-84.

In one aspect, the fourth parvovirus amplification oligomer is as above and the second amplification oligomer as set forth the following: the second parvovirus target-hybridizing sequence of (I)(b) is contained in the sequence of SEQ ID NO:187 and includes at least the sequence of SEQ ID NO:188; the second parvovirus target-hybridizing sequence of (I)(b) includes at least the sequence of SEQ ID NO:186; the second parvovirus target-hybridizing sequence of (I)(b) is selected from the group consisting of SEQ ID NOs:108-113; the second parvovirus target-hybridizing sequence of (I)(b) is contained in the sequence of SEQ ID NO:191; the second parvovirus target-hybridizing sequence of (I)(b) includes at least the sequence of SEQ ID NO:190; the second parvovirus target-hybridizing sequence of (I)(b) is selected from the group consisting of SEQ ID NOs:118-121; the second parvovirus amplification oligomer is a promoter primer or promoter provider further comprising a promoter sequence located 5' to the target-hybridizing sequence; the second parvovirus amplification oligomer is a promoter primer or promoter provider further comprising a promoter sequence that is a T7 promoter sequence; the second parvovirus amplification oligomer is a promoter primer or promoter provider further comprising and the T7 promoter sequence has the sequence shown in SEQ ID NO:196; and the second parvovirus amplification oligomer has a sequence selected from the group consisting of SEQ ID NO:88-93 and 98-101.

In one embodiment, there is provided an oligomer combination made up of any of the amplification oligomer described herein and the oligomer combination further comprises at least one parvovirus-specific capture probe oligomer comprising a target-hybridizing sequence covalently attached to a sequence or moiety that binds to an immobilized probe, wherein said target-hybridizing sequence is selected from the group consisting of SEQ ID NOs:132-135. In one aspect. the parvovirus-specific capture probe oligomer has a sequence selected from the group consisting of SEQ ID NOs:128-131.

In one embodiment, there is provided an oligomer combination made up of any of the amplification oligomer described herein and the oligomer combination further comprises a displacer oligomer comprising a target-hybridizing sequence configured to hybridize to the parvovirus target nucleic acid upstream from the first or second parvovirus amplification oligomer. In one aspect, the oligomer combination further comprises at least one parvovirus-specific capture probe oligomer comprising a target-hybridizing sequence covalently attached to a sequence or moiety that binds to an immobilized probe, wherein said target-hybridizing sequence is selected from the group consisting of SEQ ID NOs:132-135. In one aspect, the parvovirus-specific capture probe oligomer has a sequence selected from the group consisting of SEQ ID NOs:128-131.

In one embodiment, there is provided an oligomer combination made up of any of ant of the amplification oligomer described herein and the oligomer combination further comprises at least one parvovirus-specific detection probe oligomer comprising a target-hybridizing sequence that is from about 14 to about 40 nucleotides in length and is configured to specifically hybridize to a target sequence contained within SEQ ID NO:199 from about nucleotide position 2921 to about nucleotide position 2966, or from about nucleotide position 2921 to about nucleotide position 3067. In one aspect, the parvovirus-specific detection probe target-hybridizing sequence is contained in the sequence of SEQ ID NO:194 or 195. In one aspect, the parvovirus-specific detection probe target-hybridizing sequence is selected from the group consisting of SEQ ID NOs:137-169. In one aspect, the oligomer combination further comprises a displacer oligomer comprising a target-hybridizing sequence configured to hybridize to the parvovirus target nucleic acid upstream from the first or second parvovirus amplification oligomer. In one aspect, the oligomer combination further comprises at least one parvovirus-specific capture probe oligomer comprising a target-hybridizing sequence covalently attached to a sequence or moiety that binds to an immobilized probe, wherein said target-hybridizing sequence is selected from the group consisting of SEQ ID NOs:132-135. In one aspect, the parvovirus-specific capture probe oligomer has a sequence selected from the group consisting of SEQ ID NOs:128-131.

In one embodiment, the combination of oligomers is any of the above parvovirus oligomer combinations further comprising the first and second HAV amplification oligomers of (II). In one aspect, the first target-hybridizing sequence of (II)(a) is contained in the sequence of SEQ ID NO:172. In one aspect, the first target-hybridizing sequence of (II)(a) includes at least the sequence of SEQ ID NO:170. In one aspect, the first HAV target-hybridizing sequence of (II)(a) is selected from the group consisting of SEQ ID NOs:1-6 and 11. In one aspect, the first HAV target-hybridizing sequence of (II)(a) includes at least the sequence of SEQ ID NO:171. In one aspect, the first HAV target-hybridizing sequence of (II)(a) is selected from the group consisting of SEQ ID NOs:1-6. in one aspect, the second HAV target-hybridizing sequence of (II)(b) is contained in the sequence of SEQ ID NO:176. In one aspect, the second HAV target-hybridizing sequence of (II)(b) is selected from the group consisting of SEQ ID NOs:29-38 and 45. In one aspect, the second HAV amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second HAV amplification oligomer has a sequence selected from the group consisting of SEQ ID NO:12-21 and 28.

In one embodiment, the combination of oligomers is any of the above parvovirus oligomer combinations and HAV oligomer combination, further comprising (IV) third and fourth amplification oligomers for amplifying the HAV nucleic acid target region, wherein (a) the third HAV amplification oligomer comprises a third target-hybridizing sequence that is from about 14 to about 27 contiguous nucleotides contained in the sequence of SEQ ID NO:174 and that includes at least the sequence of SEQ ID NO:173; and (b) the fourth HAV amplification oligomer comprises a fourth target-hybridizing sequence that is from about 14 to about 30 contiguous nucleotides contained in the sequence of SEQ ID NO:177 and that includes at least the sequence of SEQ ID NO:175; wherein the third target-hybridizing sequence of (IV)(a) is different from the first HAV target-hybridizing sequence of (II)(a); and wherein the fourth target-hybridizing sequence of (IV)(b) is different from the second HAV target-hybridizing sequence of (II)(b). In one aspect, the third HAV amplification oligomer is an oligomer as set forth in any of claims 30 to 34 for the first HAV amplification oligomer. In one aspect, the fourth HAV amplification oligomer is an oligomer as set forth in claims 35 to 40 for the second HAV amplification oligomer.

In one embodiment, there is provided an oligomer combination made up of any of the amplification oligomer described herein and the oligomer combination further comprises at least one HAV-specific capture probe oligomer comprising a target-hybridizing sequence covalently attached to a sequence or moiety that binds to an immobilized probe, wherein said target-hybridizing sequence is selected from the group consisting of SEQ ID NOs:52-57. In one aspect, the HAV-specific capture probe oligomer has a sequence selected from the group consisting of SEQ ID NOs:46-51.

In one embodiment, there is provided an oligomer combination made up of any of the amplification oligomer described herein and the oligomer combination further comprises a a displacer oligomer comprising a target-hybridizing sequence configured to hybridize to the HAV target nucleic acid upstream from the first or second HAV amplification oligomer. In one aspect, the oligomer combination further comprises at least one HAV-specific capture probe oligomer comprising a target-hybridizing sequence covalently attached to a sequence or moiety that binds to an immobilized probe, wherein said target-hybridizing sequence is selected from the group consisting of SEQ ID NOs:52-57. In one aspect, the HAV-specific capture probe oligomer has a sequence selected from the group consisting of SEQ ID NOs:46-51.

In one embodiment, there is provided an oligomer combination made up of any of ant of the amplification oligomer described herein and the oligomer combination further comprises at least one parvovirus-specific HAV-specific detection probe oligomer comprising a target-hybridizing sequence that is from about 14 to about 40 nucleotides in length and is configured to specifically hybridize to a target sequence contained within SEQ ID NO:198 from about nucleotide position 5965 to about nucleotide position 6028. In one aspect, the HAV-specific capture probe oligomer has a sequence selected from the group consisting of SEQ ID NOs:46-51. In one aspect the HAV-specific detection probe target-hybridizing sequence is contained in the sequence of SEQ ID NO:178. In one aspect, the HAV-specific detection probe target-hybridizing sequence is selected from the group consisting of SEQ ID NOs:58-74. In one aspect, the oligomer combination made up of any of the amplification oligomer described herein and the oligomer combination further comprises a a displacer oligomer comprising a target-hybridizing sequence configured to hybridize to the HAV target nucleic acid upstream from the first or second HAV amplification oligomer. In one aspect, the oligomer combination further comprises at least one HAV-specific capture probe oligomer comprising a target-hybridizing sequence covalently attached to a sequence or moiety that binds to an immobilized probe, wherein said target-hybridizing sequence is selected from the group consisting of SEQ ID NOs:52-57.

One embodiment is a kit comprising any of the oligomer combinations described herein. One embodiment is a reaction mixture comprising any of the oligomer combinations described herein. One embodiment is a singleplex amplification assay for the amplification of hepatitis A virus using at least one amplification oligomer described herein. In one aspect, the hepatitis A virus singleplex amplification assay is for the amplification and detection of hepatitis A virus using at least one detection probe oligomer described herein. One embodiment is a singleplex amplification assay for the amplification of parvovirus using at least one amplification oligomer described herein. In one aspect, the parvovirus singleplex amplification assay is for the amplification and detection of parvovirus using at least one detection probe oligomer described herein. One embodiment is a multiplex amplification assay for the amplification of hepatitis A virus and parvovirus using at least one amplification oligomer described herein. In one aspect, the hepatitis A virus and parvovirus multiplex amplification assay is for the amplification and detection of hepatitis A virus and parvovirus using at least one detection probe oligomer described herein.

One embodiment is a method for detecting at least one of a human parvovirus target nucleic acid and a hepatitis A virus (HAV) target nucleic acid in a sample, the method comprising: (A) providing a sample, wherein the sample is suspected of containing at least one of human parvovirus and HAV; (B) contacting said sample with an oligomer combination for amplifying at least one of a human parvovirus nucleic acid target region and an HAV nucleic acid target region, said oligomer combination comprising (I) for the parvovirus target region, (a) a first parvovirus amplification oligomer comprising a first target-hybridizing sequence that is from about 14 to about 27 contiguous nucleotides contained in the sequence of SEQ ID NO:181 and that includes at least the sequence of SEQ ID NO:117, SEQ ID NO:179 or SEQ ID NO:180; and (b) a second parvovirus amplification oligomer comprising a second target-hybridizing sequence selected from the group consisting of (i) a sequence that is from about 14 to about 30 contiguous nucleotides contained in the sequence of SEQ ID NO:189 and that includes at least the sequence of SEQ ID NO:188, and (ii) a sequence that is from about 14 to about 30 contiguous nucleotides contained in the sequence of SEQ ID NO:193 and that includes at least the sequence of SEQ ID NO:192; and/or (II) for the HAV target region, (a) a first HAV amplification oligomer comprising a first target-hybridizing sequence that is from about 14 to about 27 contiguous nucleotides contained in the sequence of SEQ ID NO:174 and that includes at least the sequence of SEQ ID NO:173; and (b) a second HAV amplification oligomer comprising a second target-hybridizing sequence that is from about 14 to about 30 contiguous nucleotides contained in the sequence of SEQ ID NO:177 and that includes at least the sequence of SEQ ID NO:175; (C) performing an in vitro nucleic acid amplification reaction, wherein any parvovirus and/or HAV target nucleic acid present in said sample is used as a template for generating a parvovirus and/or HAV amplification product; and (D) detecting the presence or absence of the parvovirus and/or HAV amplification product, thereby indicating the presence or absence of parvovirus and/or HAV in said sample.

In one aspect, the method is for detecting the human parvovirus target nucleic acid and the sample is contacted with the first and second parvovirus amplification oligomers of (I). In one aspect. the first parvovirus target-hybridizing sequence of (I)(a) is contained in the sequence of SEQ ID NO:182 and includes at least the sequence of SEQ ID NO:179. In one aspect, the first parvovirus target-hybridizing sequence of (I)(a) includes at least the sequence of SEQ ID NO:117 or SEQ ID NO:183. In one aspect, the first parvovirus target-hybridizing sequence of (I)(a) has a sequence selected from the group consisting of SEQ ID NOs:75-80. In one aspect, the first parvovirus target-hybridizing sequence of (I)(a) is contained in the sequence of SEQ ID NO:184. In one aspect, the first parvovirus target-hybridizing sequence of (I)(a) is selected from the group consisting of SEQ ID NOs:75, 76, 77 and 81-84. In one aspect, the first parvovirus target-hybridizing sequence of (I)(a) is contained in the sequence of SEQ ID NO:185 and includes at least the sequence of SEQ ID NO:180. In one aspect, the first parvovirus target-hybridizing sequence of (I)(a) is selected from the group consisting of SEQ ID NOs:82-84. In one aspect, the second parvovirus target-hybridizing sequence of (I)(b) is contained in the sequence of SEQ ID NO:187 and includes at least the sequence of SEQ ID NO:188. In one aspect, the second parvovirus target-hybridizing sequence of (I)(b) includes at least the sequence of SEQ ID NO:186. in one aspect, the second parvovirus target-hybridizing sequence of (I)(b) is selected from the group consisting of SEQ ID NOs:108-113. In one aspect, the second parvovirus target-hybridizing sequence of (I)(b) is contained in the sequence of SEQ ID NO:191. In one aspect, the second parvovirus target-hybridizing sequence of (I)(b) includes at least the sequence of SEQ ID NO:190. In one aspect, the second parvovirus target-hybridizing sequence of (I)(b) is selected from the group consisting of SEQ ID NOs:118-121. In one aspect, the second parvovirus amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second parvovirus amplification oligomer has a sequence selected from the group consisting of SEQ ID NO:88-93 and 98-101.

In one embodiment, step (B) further comprises contacting the sample with (III) third and fourth amplification oligomers for amplifying the human parvovirus nucleic acid target region, wherein (a) the third parvovirus amplification oligomer comprises a third target-hybridizing sequence that is from about 14 to about 27 contiguous nucleotides contained in the sequence of SEQ ID NO:181 and that includes at least the sequence of SEQ ID NO:117, SEQ ID NO:179 or SEQ ID NO:180; and (b) the fourth parvovirus amplification oligomer comprises a fourth target-hybridizing sequence selected from the group consisting of (i) a sequence that is from about 14 to about 30 contiguous nucleotides contained in the sequence of SEQ ID NO:189 and that includes at least the sequence of SEQ ID NO:188, and (ii) a sequence that is from about 14 to about 30 contiguous nucleotides contained in the sequence of SEQ ID NO:193 and that includes at least the sequence of SEQ ID NO:192; wherein the third target-hybridizing sequence of (III)(a) is different from the first parvovirus target-hybridizing sequence of (I)(a); and wherein the fourth target-hybridizing sequence of (III)(b) is different from the second parvovirus target-hybridizing sequence of (I)(b). In one aspect, the third parvovirus amplification oligomer is an oligomer contained in the sequence of SEQ ID NO:182 and includes at least the sequence of SEQ ID NO:179. In one aspect, the third parvovirus target-hybridizing sequence of (I)(a) includes at least the sequence of SEQ ID NO:117 or SEQ ID NO:183. In one aspect, the third parvovirus target-hybridizing sequence of (I)(a) has a sequence selected from the group consisting of SEQ ID NOs:75-80. In one aspect, the third parvovirus target-hybridizing sequence of (I)(a) is contained in the sequence of SEQ ID NO:184. In one aspect, the third parvovirus target-hybridizing sequence of (I)(a) is selected from the group consisting of SEQ ID NOs:75-77 and 81-84. In one aspect, the third parvovirus target-hybridizing sequence of (I)(a) is contained in the sequence of SEQ ID NO:185 and includes at least the sequence of SEQ ID NO:180. In one aspect, the third parvovirus target-hybridizing sequence of (I)(a) is selected from the group consisting of SEQ ID NOs:82-84. In one aspect, the fourth parvovirus amplification oligomer is contained in the sequence of SEQ ID NO:187 and includes at least the sequence of SEQ ID NO:188. In one aspect, the fourth parvovirus target-hybridizing sequence of (I)(b) includes at least the sequence of SEQ ID NO:186. In one aspect, the fourth parvovirus target-hybridizing sequence of (I)(b) is selected from the group consisting of SEQ ID NOs:108-113. In one aspect, the fourth parvovirus target-hybridizing sequence of (I)(b) is contained in the sequence of SEQ ID NO:191. In one aspect, the fourth parvovirus target-hybridizing sequence of (I)(b) includes at least the sequence of SEQ ID NO:190. In one aspect, the fourth parvovirus target-hybridizing sequence of (I)(b) is selected from the group consisting of SEQ ID NOs:118-121. In one aspect, the fourth parvovirus amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the fourth parvovirus amplification oligomer has a sequence selected from the group consisting of SEQ ID NO:88-93 and 98-101.

In one embodiment, the method for detecting at least one of a human parvovirus target nucleic acid and a hepatitis A virus (HAV) target nucleic acid in a sample further comprises purifying the parvovirus target nucleic acid from other components in the sample before step (B). In one aspect, the purifying step comprises contacting the sample with at least one parvovirus-specific capture probe oligomer comprising a target-hybridizing sequence covalently attached to a sequence or moiety that binds to an immobilized probe, wherein said target-hybridizing sequence is selected from the group consisting of SEQ ID NOs:132-135. In one aspect, the parvovirus-specific capture probe oligomer has a sequence selected from the group consisting of SEQ ID NOs:128-131.

In one embodiment of the method for detecting at least one of a human parvovirus target nucleic acid and a hepatitis A virus (HAV) target nucleic acid in a sample, step (B) further comprises contacting the sample with a displacer oligomer comprising a target-hybridizing sequence configured to hybridize to the parvovirus target nucleic acid upstream from the first or second parvovirus amplification oligomer.

In one embodiment of the method for detecting at least one of a human parvovirus target nucleic acid and a hepatitis A virus (HAV) target nucleic acid in a sample, the detecting step (D) comprises contacting said in vitro nucleic acid amplification reaction with a parvovirus-specific detection probe oligomer configured to specifically hybridize to the parvovirus amplification product under conditions whereby the presence or absence of the parvovirus amplification product is determined, thereby indicating the presence or absence of parvovirus in said sample. In one aspect, the parvovirus-specific detection probe oligomer comprises a target-hybridizing sequence that is from about 14 to about 40 nucleotides in length and is configured to specifically hybridize to a target sequence contained within SEQ ID NO:199 from about nucleotide position 2921 to about nucleotide position 2966, or from about nucleotide position 2921 to about nucleotide position 3067. In one aspect, the parvovirus-specific detection probe target-hybridizing sequence is contained in the sequence of SEQ ID NO:194 or 195. In one aspect, the parvovirus-specific detection probe target-hybridizing sequence is selected from the group consisting of SEQ ID NOs:137-169. In one aspect, the parvovirus-specific detection probe comprises a label selected from the group consisting of (a) a chemiluminescent label; (b) a fluorescent label; (c) a quencher; and (d) a combination of one or more of (a), (b), and (c).

In one embodiment, the method for detecting at least one of a human parvovirus target nucleic acid and a hepatitis A virus (HAV) target nucleic acid in a sample, further comprises contacting the sample with a pseudotarget oligomer that can be amplified, using the first and second parvovirus amplification oligomers, in the in vitro nucleic acid amplification reaction to generate a second amplification product that does not specifically hybridize to the parvovirus-specific detection probe under the detection reaction conditions.

In one embodiment, the method for detecting at least one of a human parvovirus target nucleic acid and a hepatitis A virus (HAV) target nucleic acid in a sample further comprises contacting the sample with a cold probe oligomer that competes with the parvovirus-specific detection probe oligomer for hybridization to the parvovirus amplification product.

In one embodiment, the method for detecting at least one of a human parvovirus target nucleic acid and a hepatitis A virus (HAV) target nucleic acid in a sample further comprises contacting the sample with a tuner oligomer configured to specifically hybridize to both the first and second parvovirus amplification oligomers.

In one embodiment of the method for detecting at least one of a human parvovirus target nucleic acid and a hepatitis A virus (HAV) target nucleic acid in a sample the detecting step (D) occurs during the amplifying step (C). In one aspect, the parvovirus-specific detection probe comprises a fluorescent label, a quencher, or both. In one aspect, the parvovirus-specific detection probe is a TaqMan detection probe or a molecular beacon. In one aspect, the parvovirus-specific detection probe comprises a label selected from the group consisting of (a) a chemiluminescent label; (b) a fluorescent label; (c) a quencher; and (d) a combination of one or more of (a), (b), and (c). In one aspect, the parvovirus-specific detection probe further comprises a non-target-hybridizing sequence. In one aspect, the parvovirus-specific detection probe is a hairpin detection probe. In one aspect, the hairpin detection probe is a molecular beacon or a molecular torch.

In one embodiment of the method for detecting at least one of a human parvovirus target nucleic acid and a hepatitis A virus (HAV) target nucleic acid in a sample, the amplification reaction at step (C) is an isothermal amplification reaction. In one aspect, the amplification reaction is a real-time amplification reaction.

In one embodiment of the method for detecting at least one of a human parvovirus target nucleic acid and a hepatitis A virus (HAV) target nucleic acid in a sample, the amplification reaction at step (C) is a PCR amplification reaction. In one aspect, the amplification reaction is a real-time amplification reaction.

In one embodiment of the method for detecting at least one of a human parvovirus target nucleic acid and a hepatitis A virus (HAV) target nucleic acid in a sample, wherein the method is for detecting the HAV target nucleic acid the sample is contacted with the first and second HAV amplification oligomers of (II). In one aspect, the first HAV target-hybridizing sequence of (II)(a) is contained in the sequence of SEQ ID NO:172. In one aspect, the first HAV target-hybridizing sequence of (II)(a) includes at least the sequence of SEQ ID NO:170. In one aspect, the first HAV target-hybridizing sequence of (II)(a) is selected from the group consisting of SEQ ID NOs:1-6 and 11. In one aspect, the first HAV target-hybridizing sequence of (II)(a) includes at least the sequence of SEQ ID NO:171. In one aspect, the first HAV target-hybridizing sequence of (II)(a) is selected from the group consisting of SEQ ID NOs:1-6. In one aspect, the second HAV target-hybridizing sequence of (II)(b) is contained in the sequence of SEQ ID NO:176. In one aspect, the second HAV target-hybridizing sequence of (II)(b) is selected from the group consisting of SEQ ID NOs:29-38 and 45. In one aspect, the second HAV amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second HAV amplification oligomer has a sequence selected from the group consisting of SEQ ID NO:12-21 and 28.

In one embodiment, step (B) further comprises contacting the sample with (IV) third and fourth amplification oligomers for amplifying the HAV nucleic acid target region, wherein (a) the third HAV amplification oligomer comprises a third target-hybridizing sequence that is from about 14 to about 27 contiguous nucleotides contained in the sequence of SEQ ID NO:174 and that includes at least the sequence of SEQ ID NO:173; and (b) the fourth HAV amplification oligomer comprises a fourth target-hybridizing sequence that is from about 14 to about 30 contiguous nucleotides contained in the sequence of SEQ ID NO:177 and that includes at least the sequence of SEQ ID NO:175; wherein the third target-hybridizing sequence of (IV)(a) is different from the first HAV target-hybridizing sequence of (II)(a); and wherein the fourth target-hybridizing sequence of (IV) (b) is different from the second HAV target-hybridizing sequence of (II)(b). In one aspect, the third HAV amplification oligomer is an oligomer as set forth in any of claims 96 to 100 for the first HAV amplification oligomer. In one aspect, the fourth HAV amplification oligomer is an oligomer as set forth in claims 101 to 106 for the second HAV amplification oligomer.

In one embodiment, the method for detecting at least one of a human parvovirus target nucleic acid and a hepatitis A virus (HAV) target nucleic acid in a sample further comprises purifying the HAV target nucleic acid from other components in the sample before step (B). In one aspect, the purifying step comprises contacting the sample with at least one HAV-specific capture probe oligomer comprising a target-hybridizing sequence covalently attached to a sequence or moiety that binds to an immobilized probe, wherein said target-hybridizing sequence is selected from the group consisting of SEQ ID NOs:52-57. In one aspect, the HAV-specific capture probe oligomer has a sequence selected from the group consisting of SEQ ID NOs:46-51.

In one embodiment, the method for detecting at least one of a human parvovirus target nucleic acid and a hepatitis A virus (HAV) target nucleic acid in a sample further comprises at the amplification step, using a displacer oligomer comprising a target-hybridizing sequence configured to hybridize to the HAV target nucleic acid upstream from the first or second HAV amplification oligomer.

In one embodiment of the method for detecting at least one of a human parvovirus target nucleic acid and a hepatitis A virus (HAV) target nucleic acid in a sample, the detecting step (D) comprises contacting said in vitro nucleic acid amplification reaction with an HAV-specific detection probe oligomer configured to specifically hybridize to the HAV amplification product under conditions whereby the presence or absence of the HAV amplification product is determined, thereby indicating the presence or absence of HAV in said sample. In one aspect, the HAV-specific detection probe oligomer comprises a target-hybridizing sequence that is from about 14 to about 40 nucleotides in length and is configured to specifically hybridize to a target sequence contained within SEQ ID NO:198 from about nucleotide position 5965 to about nucleotide position 6028. In one aspect, the HAV-specific detection probe target-hybridizing sequence is contained in the sequence of SEQ ID NO:178. In one aspect, the HAV-specific detection probe target-hybridizing sequence is selected from the group consisting of SEQ ID NOs:58-74. In one aspect, the HAV-specific detection probe comprises a label selected from the group consisting of (a) a chemiluminescent label; (b) a fluorescent label; (c) a quencher; and (d) a combination of one or more of (a), (b), and (c).

In one embodiment, the method for detecting at least one of a human parvovirus target nucleic acid and a hepatitis A virus (HAV) target nucleic acid in a sample further comprises contacting the sample with a pseudotarget oligomer that can be amplified, using the first and second HAV amplification oligomers, in the in vitro nucleic acid amplification reaction to generate a second amplification product that does not specifically hybridize to the HAV-specific detection probe under the detection reaction conditions.

In one embodiment, the method for detecting at least one of a human parvovirus target nucleic acid and a hepatitis A virus (HAV) target nucleic acid in a sample further comprises contacting the sample with a cold probe oligomer that competes with the HAV-specific detection probe oligomer for hybridization to the HAV amplification product.

In one embodiment, the method for detecting at least one of a human parvovirus target nucleic acid and a hepatitis A virus (HAV) target nucleic acid in a sample further comprises contacting the sample with a tuner oligomer configured to specifically hybridize to both the first and second HAV amplification oligomers.

In one embodiment of the method for detecting at least one of a human parvovirus target nucleic acid and a hepatitis A virus (HAV) target nucleic acid in a sample, the detecting step (D) occurs during the amplifying step (C). In one aspect, the HAV-specific detection probe comprises a fluorescent label, a quencher, or both. In one aspect, the HAV-specific detection probe is a TaqMan detection probe or a molecular beacon. In one aspect, the HAV-specific detection probe comprises a label selected from the group consisting of (a) a chemiluminescent label; (b) a fluorescent label; (c)

a quencher; and (d) a combination of one or more of (a), (b), and (c). In one aspect, the HAV-specific detection probe further comprises a non-target-hybridizing sequence. In one aspect, the HAV-specific detection probe is a hairpin detection probe. In one aspect, the hairpin detection probe is a molecular beacon or a molecular torch.

In one embodiment of the method for detecting at least one of a human parvovirus target nucleic acid and a hepatitis A virus (HAV) target nucleic acid in a sample, the amplification reaction at step (C) is an isothermal amplification reaction.

In one embodiment of the method for detecting at least one of a human parvovirus target nucleic acid and a hepatitis A virus (HAV) target nucleic acid in a sample, the amplification reaction at step (C) is a PCR amplification reaction.

In one embodiment of the method for detecting at least one of a human parvovirus target nucleic acid and a hepatitis A virus (HAV) target nucleic acid in a sample, the amplification reaction is a real-time amplification reaction.

In one embodiment of the method for detecting at least one of a human parvovirus target nucleic acid and a hepatitis A virus (HAV) target nucleic acid in a sample, the sample is from an individual patient. In one aspect, the sample is pooled. In one aspect, the pooled sample is a pooled plasma sample. In one aspect, the sample is a plasma sample for deriving a therapeutic compound. In one aspect, the sample is a plasma sample for deriving a compound that is human thrombin, a human antibody or portions thereof, a human protein, a human cytokine receptor, a human cytokine ligand, or other plasma derived compound.

In one embodiment of the method for detecting at least one of a human parvovirus target nucleic acid and a hepatitis A virus (HAV) target nucleic acid in a sample, wherein the method is for detecting both the human parvovirus target nucleic acid and the HAV target nucleic acid, and wherein the detecting step (D) comprises contacting said in vitro nucleic acid amplification reaction with a parvovirus-specific detection probe oligomer and an HAV-specific detection probe oligomer configured to specifically hybridize, respectively, to the parvovirus amplification product and the HAV amplification under conditions whereby the presence or absence of the parvovirus amplification product and the HAV amplification product are determined, thereby indicating the presence or absence of parvovirus and HAV in said sample. In one aspect, the parvovirus-specific and HAV-specific detection probe oligomers are differentially labeled. In one aspect wherein each of the parvovirus-specific and HAV-specific detection probe oligomers comprises a label, the labels are independently selected from the group consisting of (a) a chemiluminescent label and (b) a fluorescent label. In one aspect, each of the parvovirus-specific and HAV-specific detection probe oligomers comprises a chemiluminescent label. In one aspect, the chemiluminescent labels for the parvovirus-specific and HAV-specific detection probe oligomers are characterized by different light emission kinetics sufficient to distinguish between parvovirus-specific and HAV-specific chemiluminescent signals. In one aspect, each of the chemiluminescent labels for the parvovirus-specific and HAV-specific detection probe oligomers comprises an acridinium ester (AE). In one aspect, the first parvovirus target-hybridizing sequence of (I)(a) is contained in the sequence of SEQ ID NO:182 and includes at least the sequence of SEQ ID NO:117 or SEQ ID NO:179. In one aspect, the first parvovirus target-hybridizing sequence of (I)(a) includes at least the sequence of SEQ ID NO:183. In one aspect, the first parvovirus target-hybridizing sequence of (I)(a) has a sequence selected from the group consisting of SEQ ID NOs:75-80. In one aspect, the first parvovirus target-hybridizing sequence of (I)(a) is contained in the sequence of SEQ ID NO:184. In one aspect, the first parvovirus target-hybridizing sequence of (I)(a) is selected from the group consisting of SEQ ID NOs:81-84. In one aspect, the first parvovirus target-hybridizing sequence of (I)(a) is contained in the sequence of SEQ ID NO:185 and includes at least the sequence of SEQ ID NO:180. In one aspect, the first parvovirus target-hybridizing sequence of (I)(a) is selected from the group consisting of SEQ ID NOs:82-84. In one aspect, the second parvovirus target-hybridizing sequence of (I)(b) is contained in the sequence of SEQ ID NO:187 and includes at least the sequence of SEQ ID NO:188. In one aspect, the second parvovirus target-hybridizing sequence of (I)(b) includes at least the sequence of SEQ ID NO:186. In one aspect, the second parvovirus target-hybridizing sequence of (I)(b) is selected from the group consisting of SEQ ID NOs:108-113. In one aspect, the second parvovirus target-hybridizing sequence of (I)(b) is contained in the sequence of SEQ ID NO:191. In one aspect, the second parvovirus target-hybridizing sequence of (I)(b) includes at least the sequence of SEQ ID NO:190. In one aspect, the second parvovirus target-hybridizing sequence of (I)(b) is selected from the group consisting of SEQ ID NOs:118-121. In one aspect, the second parvovirus amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second parvovirus amplification oligomer has a sequence selected from the group consisting of SEQ ID NO:88-93 and 98-101. In one aspect, the first HAV target-hybridizing sequence of (II)(a) is contained in the sequence of SEQ ID NO:172. In one aspect, the first HAV target-hybridizing sequence of (II)(a) includes at least the sequence of SEQ ID NO:170. In one aspect, the first HAV target-hybridizing sequence of (II)(a) is selected from the group consisting of SEQ ID NOs:1-6 and 11. In one aspect, the first HAV target-hybridizing sequence of (II)(a) includes at least the sequence of SEQ ID NO:171. In one aspect, the first HAV target-hybridizing sequence of (II)(a) is selected from the group consisting of SEQ ID NOs:1-6. In one aspect, the second HAV target-hybridizing sequence of (II)(b) is contained in the sequence of SEQ ID NO:176. In one aspect, the second HAV target-hybridizing sequence of (II)(b) is selected from the group consisting of SEQ ID NOs:29-38 and 45. In one aspect, the second HAV amplification oligomer is a promoter primer or promoter provider further comprising a promoter sequence located 5' to the target-hybridizing sequence. In one aspect, the promoter sequence is a T7 promoter sequence. In one aspect, the T7 promoter sequence has the sequence shown in SEQ ID NO:196. In one aspect, the second HAV amplification oligomer has a sequence selected from the group consisting of SEQ ID NO:12-21 and 28. In one aspect, the parvovirus-specific detection probe oligomer comprises a target-hybridizing sequence that is from about 14 to about 40 nucleotides in length and is configured to specifically hybridize to a target sequence contained within SEQ ID NO:199 from about nucleotide position 2921 to about nucleotide position 2966, or from about nucleotide position 2921 to about nucleotide position 3067. In one aspect, the parvovirus-specific detection probe target-hybridizing sequence is contained in the sequence of SEQ ID NO:194 or 195. In one aspect, the parvovirus-specific detection probe target-hybridizing sequence is selected from the group consisting of SEQ ID NOs:137-169. In one aspect, the HAV-specific detection probe oligomer comprises a target-hybridizing sequence that is from about 14 to about 40 nucleotides in length and is configured to specifically hybridize to a target sequence contained within SEQ ID NO:198 from about nucleotide position 5965 to about nucleotide position 6028. In one aspect, the HAV-specific detection probe target-hybridizing sequence is contained in the sequence of SEQ ID NO:178. In one aspect, the HAV-specific detection probe target-hybridizing sequence is selected from the group consisting of SEQ ID NOs:58-74.

In one embodiment there is provided a method for the multiplex amplification and detection of human parvovirus genotypes 1, 2 and 3 target nucleic acids and hepatitis A virus target nucleic acid from a sample. In one aspect of this embodiment, the amplification oligomers for the amplification and detection of human parvovirus genotypes 1, 2 and 3 include one or more amplification oligomers described in Table 3. In another aspect, two or more amplification oligomers described in Table 3. In another aspect, three or more amplification oligomers described in Table 3. In another aspect, four or more amplification oligomers described in Table 3. In another aspect, five or more amplification oligomers described in Table 3. In another aspect, six or more amplification oligomers described in Table 3. In another aspect, seven or more amplification oligomers described in Table 3. In one aspect of this embodiment, the amplification oligomers for the amplification and detection of HAV include one or more amplification oligomers described in Table 3. In another aspect, two or more amplification oligomers described in Table 3. In another aspect, three or more amplification oligomers described in Table 3. In another aspect, four or more amplification oligomers described in Table 3. In another aspect, five or more amplification oligomers described in Table 3. In another aspect, six or more amplification oligomers described in Table 3. In another aspect, seven or more amplification oligomers described in Table 3. In one aspect of this embodiment, the detection probe oligomers for detection of amplification products generated from human parvovirus genotypes 1, 2 and 3, and for detection of amplification products generated from HAV include one or more parvovirus detection probes described in Table 3 and one or more HAV detection probes described in Table 3. In another aspect, the detection probe oligomers are present during amplification for a real time detection. In another aspect, the detection probe oligomers are combined with the amplification products after the amplification reaction for an end point detection. In one aspect of this embodiment, the multiplex amplification and detection of human parvovirus genotypes 1, 2, and 3 target nucleic acids HAV target nucleic acids is a quantitative multiplex amplification and detection reaction. In one aspect of this embodiment, the human parvovirus genotype 1, 2 and 3 target nucleic acids are isolated from other sample components. In another aspect, the isolation is performed using a target capture oligomer. In one aspect of this embodiment, the HAV target nucleic acids are isolated from other sample components. In another aspect, the isolation is performed using a target capture oligomer. In one aspect of this embodiment, the amplification and detection reactions include an internal control.

DETAILED DESCRIPTION

This application discloses oligonucleotide sequences configured for use as amplification oligomers and detection probe oligomers for detecting by an in vitro nucleic acid amplification assay hepatitis A virus and/or parvovirus types 1, 2 and 3 nucleic acid sequences present in a biological sample. An embodiment of the method uses transcription-mediated nucleic acid amplification (as previously disclosed in detail in U.S. Pat. Nos. 5,399,491 and 5,554,516 to Kacian et al.). Methods for detecting amplified nucleic acid use sequence-specific probes that hybridize specifically to a portion of the amplified sequences. In one aspect, the method uses any known homogeneous detection step to detect, in a mixture, a labeled probe that is bound to an amplified nucleic acid (e.g., as disclosed by Arnold et al., Clin. Chem. 35:1588-1594 (1989); U.S. Pat. No. 5,658,737 to Nelson et al., and U.S. Pat. Nos. 5,118,801 and 5,312,728 to Lizardi et al.). This application also discloses oligonucleotide sequences that are useful for capturing hepatitis A virus target DNA or parvovirus types 1, 2 and 3 target DNA by using nucleic acid hybridization techniques. One embodiment of the capturing step uses magnetic particles to separate the captured target (see U.S. Pat. No. 6,110,678 to Weisburg et al.).

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

By "sample" or "biological sample" is meant any material derived from a living or dead human which may contain parvovirus nucleic acid and/or hepatitis A virus nucleic acid, including, for example, sputum, peripheral blood, plasma, serum, biopsy tissue including lymph nodes, respiratory tissue or exudates, or other body fluids, tissues or materials. The sample may be treated to physically, chemically and/or mechanically disrupt tissue or cell structure, thus releasing intracellular components. Sample preparation may use a solution that contains buffers, salts, enzymes, detergents and the like which are used to prepare the sample for analysis. Samples may be pooled from two or more sources (e.g., a pooled plasma sample from two or more donors). Samples may be fractionated (e.g., a fraction of a sample such as a pooled sample). Samples may be a manufacturer's pool of plasma for isolating components therefrom.

"Nucleic acid" refers to a multimeric compound comprising two or more covalently bonded nucleosides or nucleoside analogs made up of a sugar moiety and a nitrogenous heterocyclic bases, or base analogs. Nucleosides are linked together by phosphodiester bonds or other linkages to form RNA, DNA, or chimeric DNA-RNA polymers or oligonucleotides, and analogs thereof. A nucleic acid "backbone" may be made up of a variety of linkages, (see, e.g., International Patent Application Pub. No. WO 95/32305). The sugar moiety of one or more residues in the nucleic acid may be either ribose or deoxyribose, or similar compounds having known substitutions such as, for example, 2'-methoxy substitutions and 2'-halide substitutions (e.g., 2'-F). The nitrogenous base of one or more residues in the nucleic acid may be conventional bases (A, G, C, T, U), analogs thereof (see, e.g., The Biochemistry of the Nucleic Acids 5-36, Adams et al., ed., 11th ed., 1992; Abraham et al., 2007, BioTechniques 43: 617-24), which include derivatives of purine or pyrimidine bases (see e.g., U.S. Pat. Nos. 5,378,825, 6,949,367 and International Patent Application Pub. No. WO 93/13121), or "abasic" wherein the nucleoside unit is lacking a nitrogenous base (see, e.g., U.S. Pat. No. 5,585,481). Nucleic acids may include one or more "locked nucleic acid" (LNA) residues (Vester et al., Biochemistry 43:13233-41, 2004). Nucleic acids may include a 3'-terminal dideoxynucleotide to block additional nucleotides from being added to the nucleic acid. Synthetic methods for making nucleic acids in vitro are well known in the art although nucleic acids may be purified from natural sources using routine techniques. The backbone of an oligomer may affect stability of a hybridization complex (e.g., formed between of a capture oligomer to its target nucleic acid). Such embodiments include peptide linkages, 2'-O-methoxy linkages and sugar-phosphodiester type linkages. Peptide nucleic acids are advantageous for forming a hybridization complex with RNA. An oligomer having 2'-methoxy substituted RNA groups or a 2'-fluoro substituted RNA may have enhance hybridization complex stability relative to standard DNA or RNA and is preferred for forming a hybridization complex with a complementary 2'-OH RNA. A linkage joining two sugar groups may affect hybridization complex stability by affecting the overall charge or the charge density, or by affecting steric interactions (e.g., bulky linkages may reduce hybridization complex stability). Preferred linkages include those with neutral groups (e.g., methylphosphonates) or charged groups (e.g., phosphorothioates) to affect complex stability.

The term "polynucleotide" as used herein denotes a nucleic acid chain. Throughout this application, nucleic acids are designated by the 5'-terminus to the 3'-terminus.

A "nucleotide" as used herein is a subunit of a nucleic acid consisting of a phosphate group, a 5-carbon sugar, and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

The interchangeable terms "oligomer," "oligo," and "oligonucleotide" refer to a polynucleotide having a contiguous nucleotide residue (nt) length of from 1,000 nts to as few as 5 nts. It is understood that the range from 1000 nts to as few as 5 is an inclusive range such that 1000 nts, 5 nts and each whole number of nts there between are included in the range. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein.

By "amplification oligonucleotide" or "amplification oligomer" is meant an oligonucleotide, at least the 3'-end of which is complementary to a target nucleic acid, and which hybridizes to a target nucleic acid, or its complement, and participates in nucleic acid amplification. Examples of amplification oligomers include primers and promoter-primers. Preferably, an amplification oligonucleotide contains at least 10 contiguous bases, and more preferably at least about 12 contiguous bases but less than about 70 bases, that hybridize specifically with a region of the target nucleic acid sequence under standard hybridization conditions. The contiguous bases that hybridize to the target sequence are at least about 80%, preferably at least about 90%, and more preferably about 100% complementary to the sequence to which the amplification oligonucleotide hybridizes. At least about X % refers to all a range of all whole and partial numbers from X % to 100%. An amplification oligonucleotide optionally may include modified nucleotides.

Amplification oligomers may be referred to as "primers" or "promoter-primers." A "primer" refers to an oligonucleotide that hybridizes to a template nucleic acid and has a 3' end that can be extended in a known polymerization reaction. The 5' region of the primer may be non-complementary to the target nucleic acid, e.g., the 5' non-complementary region may include a promoter sequence and the oligomer is referred to as a "promoter-primer" or it may include a tag sequence, or it may include an adapter sequence. As used herein, a "promoter" is a specific nucleic acid sequence that is recognized by a DNA-dependent RNA polymerase ("transcriptase") as a signal to bind to the nucleic acid and begin the transcription of RNA at a specific site. Further, promoter primers may comprise blocked 3' ends to prevent their use as a primer, and in these instances, the amplification oligomer is referred to as a promoter provider. In some embodiments, blocking moieties replace an oligomer's 3'OH to prevent enzyme-mediated extension of the oligomer in an amplification reaction. In alternative embodiments a blocking moiety may be within five residues of the 3' end and is sufficiently large to limit binding of a polymerase to the oligomer. In other embodiments a blocking moiety is covalently attached to the 3' terminus of an oligomer. Many different chemical groups may be used to block the 3' end of an oligomer, including, but not limited to, alkyl groups, non-nucleotide linkers, alkane-diol dideoxynucleotide residues, and cordycepin. Those skilled in the art will further appreciate that any oligomer that can function as a primer (i.e., an amplification oligonucleotide that hybridizes specifically to a target sequence and has a 3' end that can be extended by a polymerase) can be modified to include a 5' promoter sequence, and thus function as a promoter-primer. Similarly, any promoter-primer can be modified by removal of, or synthesis without, a promoter sequence and function as a primer.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence, which may not be amplified. Target nucleic acids include the genomic nucleic acid, a gene product (e.g., mRNA), and amplification products thereof. Target nucleic acids herein are human parvovirus nucleic acids and HAV nucleic acids.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during the processes of amplification. Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands.

"Target binding sequence" is used herein to refer to the portion of an oligomer that is configured to hybridize with a target nucleic acid sequence. Preferably, the target binding sequences are configured to specifically hybridize with a target nucleic acid sequence. Target binding sequences may be 100% complementary to the portion of the target sequence to which they are configured to hybridize; but not necessarily. Target-binding sequences may also include inserted, deleted and/or substituted nucleotide residues relative to a target sequence. Less than 100% complementarity of a target binding sequence to a target sequence may arise, for example, when the target nucleic acid is a plurality strains within a species, such as would be the case for an oligomer configured to hybridize to the various strains and genotypes of human parvovirus. It is understood that other reasons exist for configuring a target binding sequence to have less than 100% complementarity to a target nucleic acid.

The term "targets a sequence" as used herein in reference to a region of human parvovirus nucleic acid refers to a process whereby an oligonucleotide hybridizes to the target sequence in a manner that allows for amplification and detection as described herein. In one embodiment, the oligonucleotide is complementary with the targeted human parvovirus nucleic acid sequence and contains no mismatches. In another embodiment, the oligonucleotide is complementary but contains 1; or 2; or 3; or 4; or 5 mismatches with the targeted human parvovirus nucleic acid sequence. Preferably, the oligonucleotide that hybridizes to the human parvovirus nucleic acid sequence includes at least 10 to as many as 50 nucleotides complementary to the target sequence. It is understood that at least 10 and as many as 50 is an inclusive range such that 10, 50 and each whole number there between are disclosed. Preferably, the oligomer specifically hybridizes to the target sequence. The term "configured to target a sequence" as used herein means that the target hybridizing region of an amplification oligonucleotide is designed to have a polynucleotide sequence that could specifically hybridize to the referenced human parvovirus region or referenced HAV region. Such an amplification oligonucleotide is not limited to targeting that sequence only, but is rather useful as a composition, in a kit or in a method for targeting a human parvovirus target nucleic acid including genotypes 1, 2 and/or 3, or an HAV target nucleic acid, as is described herein. The term "configured to" denotes an actual arrangement of the polynucleotide sequence configuration of the amplification oligonucleotide target hybridizing sequence.

The term "region" as used herein refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a human parvovirus genome, the term "region" may be used to refer to a smaller area of the nucleic acid, wherein the smaller area is targeted by one or more oligonucleotides of the invention. The target binding sequence of an oligonucleotide may hybridize all or a portion of a region. A target binding sequence that hybridizes to a portion of a region is one that hybridizes within the referenced region. As another non-limiting example of the use of the term region, when the nucleic acid in reference is an amplicon, the term region may be used to refer to the smaller nucleotide sequence identified for hybridization by the target binding sequence of a probe.

"Amplification" refers to any known procedure for obtaining multiple copies of a target nucleic acid sequence or its complement or fragments thereof, and preferred embodiments amplify the target specifically by using sequence-specific methods. Known amplification methods include, for example, transcription-mediated amplification, replicase-mediated amplification, polymerase chain reaction (PCR) amplification, including RT-PCR, ligase chain reaction (LCR) amplification and strand-displacement amplification (SDA). Replicase-mediated amplification uses self-replicating RNA molecules, and a replicase such as QB-replicase (e.g., see U.S. Pat. No. 4,786,600 to Kramer et al. and PCT No. WO 90/14439). PCR amplification is well known and uses DNA polymerase, sequence-specific primers and thermal cycling to synthesize multiple copies of the two complementary strands of DNA or cDNA (e.g., U.S. Pat. Nos. 4,683,195, 4,683,202, and 4,800,159 to Mullis et al., and *Methods in Enzymology*, 1987, Vol. 155: 335-350). LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.) As illustrated below, preferred embodiments use transcription-associated amplification. It will be apparent to one skilled in the art that method steps and amplification oligonucleotides of the present invention may be readily adapted to a variety of nucleic acid amplification procedures based on primer extension by a polymerase activity.

Amplification of a "fragment" or "portion" of the target sequence refers to production of an amplified nucleic acid containing less than the entire target region nucleic acid sequence. Such fragments may be produced by amplifying a portion of the target sequence, e.g., by using an amplification oligonucleotide that hybridizes to and initiates polymerization from an internal position in the target sequence.

By "transcription-mediated amplification" (TMA) or "transcription-associated amplification" is meant a nucleic acid amplification that uses an RNA polymerase to produce multiple RNA transcripts from a nucleic acid template. Transcription-associated amplification generally employs RNA polymerase and DNA polymerase activities, deoxyribonucleoside triphosphates, ribonucleoside triphosphates, and a promoter-primer, and optionally may include one or more other amplification oligonucleotides, including "helper" oligomers. Variations of transcription-associated amplification are well known in the art and described in detail elsewhere (see U.S. Pat. Nos. 5,399,491 and 5,554,516 to Kacian et al., U.S. Pat. No. 5,437,990 to Burg et al., U.S. Pat. Nos. 5,130,238 to Malek et al., U.S. Pat. Nos. 4,868,105 and 5,124,246 to Urdea et al., PCT No. WO 93/22461 by Kacian et al., PCT Nos. WO 88/01302 and WO 88/10315 by Gingeras et al., PCT No. WO 94/03472 by McDonough et al., and PCT No. WO 95/03430 by Ryder et al.). The procedures of U.S. Pat. Nos. 5,399,491 and 5,554,516 are preferred amplification embodiments. As used herein, the term "real-time TMA" refers to single-primer transcription-mediated amplification ("TMA") of target nucleic acid that is monitored by real-time detection means.

By "probe," "detection probe" or "detection probe oligomer" it is meant a nucleic acid oligomer that hybridizes specifically to a target sequence in a nucleic acid, preferably in an amplified nucleic acid, under conditions that allow hybridization, thereby allowing detection of the target or amplified nucleic acid. Detection may either be direct (i.e., resulting from a probe hybridizing directly to the sequence) or indirect (i.e., resulting from a probe hybridizing to an intermediate molecular structure that links the probe to the target). The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe (e.g., U.S. Pat. Nos. 5,118,801 and 5,312,728 to Lizardi et al., and U.S. Pat. No. 6,361,945 B1 to Becker et al.). Probes may be DNA, RNA, analogs thereof or combinations thereof and they may be labeled or unlabeled. Probe sequences are sufficiently complementary to their target sequences if they are configured to allow stable hybridization in appropriate hybridization conditions between the probe oligomer and a target sequence that is not completely complementary to the probe's target-specific sequence.

A "cold probe" refers to an oligonucleotide that has a substantially similar or an identical oligonucleotide sequence compared to a detection probe oligomer. The main difference between the cold probe and a detection probe is that the cold probe lacks a detectable label while the detection probe oligomer possesses a detectable label. Cold probe oligomers are used in detection reactions to compete with the detection probe oligomer, thereby decreasing the total signal received at a detection step. Detection signal is often decreased for one target of a multiplex amplification and detection assay wherein one or more, but not all, of the target nucleic acids have robust amplification kinetics compares to one or more other members of the multiplex. The cold probe is used to compete with the detection probe on the stronger amplifications, thus in a sense "de-tuning" the robust amplification(s). De-tuned amplifications are then brought into a range that is more comparable to the weaker amplifying species of the multiplex. In a similar way, a pseudo-target is a nucleic acid that is applied to a multiplex amplification reaction to de-tune a stronger amplification species thereby making its reaction kinetics more similar to that of a weaker amplification species. A pseudotarget is a nucleic acid that typically contains binding sites for the primers of the stronger amplification species, but has little or no additional sequence there between. Primers are then diverted from generating amplification product for the stronger amplification species.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more non-complementary residues, including abasic residues. Sufficiently complementary contiguous sequences typically are at least 80%, or at least 90%, complementary to a sequence to which an oligomer is intended to specifically hybridize (including all whole and rational numbers up to and including 100%). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary, (e.g., Sambrook et al., Molecular Cloning, A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "preferentially hybridize" or "specifically hybridize" is meant that under stringent hybridization assay conditions, probes hybridize to their target sequences, or replicates thereof, to form stable probe: target hybrids, while at the same time formation of stable probe: non-target hybrids is minimized Thus, a probe hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art, may be predicted based on sequence composition, or can be determined by using routine testing methods (e.g., Sambrook et al., Molecular Cloning, A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "capture oligonucleotide" or "capture oligomer" or "capture probe" is meant a nucleic acid oligomer that hybridizes specifically to a target nucleic acid to be captured and provides a means for isolating and/or concentrating the target from other sample components. Embodiments of capture oligomers include two binding regions: a target-binding region and an immobilized probe-binding region, whereby the capture oligomer forms a hybridization complex in which the target-binding region of the capture oligomer binds to the target sequence and the immobilized probe-binding region binds to an oligomer immobilized on a solid support (see U.S. Pat. Nos. 6,110,678 and 6,280,952 to Weisburg et al.). Although the target-binding region and immobilized probe-binding region are usually on the same capture oligomer, the two functional regions may be present on two different oligomers joined together by one or more linkers. For example, an immobilized probe-binding region may be present on a first oligomer, a target-binding region may be present on a second oligomer, and the two oligomers are joined by hydrogen bonding with a third oligomer that is a linker that hybridizes specifically to sequences of the first and second oligomers. The target-binding region of a capture probe may also be referred to as a target-specific portion of the capture probe and the immobilized probe-binding region may be referred to as a tail portion. Embodiments of tail portions include homopolymers (e.g., poly-dT or poly-dA) or non-homopolymers (e.g., $T_{0-3}A_{15-30}$), preferably attached to the 3' end of the target-specific portion of the oligomer.

By "immobilized probe" or "immobilized oligomer" is meant a nucleic acid oligomer that joins, directly or indirectly, a capture oligomer to an immobilized support. An immobilized probe joined to a solid support facilitates separation of bound target sequence from unbound material in a sample. Any known solid support may be used, such as matrices and particles in solution, e.g., nitrocellulose, nylon, glass, polyacrylate, mixed polymers, polystyrene, silane polypropylene and metal particles, preferably, magnetically attractable particles. Preferred supports are monodisperse paramagnetic spheres (e.g., uniform size±5%), to provide consistent results, to which an immobilized probe is joined directly (e.g., via a direct covalent linkage, chelation, or ionic interaction), or indirectly (e.g., via one or more linkers), where the linkage or interaction is stable during nucleic acid hybridization conditions.

"Sample preparation" refers to any steps or method that treats a sample for subsequent amplification and/or detection of human parvovirus nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and PCT Pub. No. WO 2008/016988).

By "separating" or "purifying" is meant that one or more components of the biological sample are removed from at least one other component of the sample. Sample components generally include an aqueous solution of nucleic acids, salts, proteins, carbohydrates, and lipids. A step of separating or purifying a nucleic acid removes at least about 70%, preferably at least about 90% and, more preferably, at least about 95% of the other components in the sample.

By "label" is meant a molecular moiety or compound that can be detected or can lead to a detectable signal. A label is joined, directly or indirectly, to a nucleic acid probe. Direct labeling uses bonds or interactions that link the label to the probe, including covalent bonds or non-covalent interactions, such as hydrogen bonds, hydrophobic and ionic interactions, or through formation of chelates or coordination complexes. Indirect labeling uses a bridging moiety or "linker" (e.g., oligonucleotide or antibody), to link the label and probe. Linkers can be used to amplify a detectable signal. Labels are any known detectable moiety, e.g., radionuclide, ligand (e.g., biotin, avidin), enzyme or enzyme substrate, reactive group, or chromophore, such as a dye or detectable particle (e.g., latex beads or metal particles), luminescent compounds (e.g., bioluminescent, phosphorescent or chemiluminescent labels) and fluorescent compounds. Preferably, the label on a labeled probe is detectable in a homogeneous reaction (i.e., in a mixture, bound labeled probe exhibits a detectable change, such as stability or differential degradation, compared to unbound labeled probe). One embodiment of a label for use in a homogenous assay is a chemiluminescent compound (e.g., described in detail in U.S. Pat. No. 5,656,207 to Woodhead et al., U.S. Pat. No. 5,658,737 to Nelson et al., and U.S. Pat. No. 5,639,604 to Arnold, Jr., et al.). Preferred chemiluminescent labels are acridinium ester (AE) compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Synthesis and methods of attaching labels to nucleic acids and detecting labels are well known in the art (e.g., Sambrook et al., *Molecular Cloning, A Laboratory Manual*, 2nd ed. (Cold Spring Harbor Laboratory Press, Cold Spring Habor, N.Y., 1989), Chapter 10; U.S. Pat. No. 4,581,333 to Kourilsky et al., U.S. Pat. No. 5,658,737 to Nelson et al., U.S. Pat. No. 5,656,207 to Woodhead et al., U.S. Pat. No. 5,547,842 to Hogan et al., U.S. Pat. No. 5,283,174 to Arnold, Jr. et al., and EP Patent Pub. No. 0747706 by Becker et al.). Another embodiment of a label for use in a homogenous assay is a fluorescent compound attached to a probe with a quencher compound in functional proximity to the fluorescent label when the probe is not hybridized to its target (e.g., U.S. Pat. Nos. 5,118,801 and 5,312,728 to Lizardi et al., and U.S. Pat. No. 6,361,945 B1 to Becker et al.).

A "homogeneous detectable label" refers to a label whose presence can be detected in a homogeneous fashion based upon whether the labeled probe is hybridized to a target sequence (i.e., can be detected without physically removing unhybridized label or labeled probe). Embodiments of homogeneous detectable labels and methods of detecting them have been described (U.S. Pat. No. 5,283,174 to Arnold et al., U.S. Pat. No. 5,656,207 to Woodhead et al., U.S. Pat. No. 5,658,737 to Nelson et al., U.S. Pat. Nos. 5,118,801 and 5,312,728 to Lizardi et al., and U.S. Pat. No. 6,361,945B1 to Becker et al.).

By "consisting essentially of" is meant that additional component(s) and method step(s) that do not materially change the basic and novel characteristics of the present invention may be included. Such characteristics include salts, buffering agents, nucleic acid oligomers and similar biochemical reagents that do not have a material effect on the characteristics of the claimed components or method steps described herein that detect hepatitis A virus and/or parvovirus types 1, 2 and 3 nucleic acid sequences. Similarly, additional method steps that do not have a material effect on the basic nature of the assay may be included.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, an oligonucleotide that "corresponds to" or is "corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "corresponding oligonucleotides" can vary from the referred to sequence and still hybridize to the same target nucleic acid sequence. It is also understood that a first nucleic acid corresponding to a second nucleic acid includes the complements thereof and includes the RNA and DNA thereof. This variation from the nucleic acid may be stated in terms of a percentage of identical bases within the sequence or the percentage of perfectly complementary bases between the probe or primer and its target sequence. Thus, an oligonucleotide "corresponds to" a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

The term "amplicon" or the term "amplification product" as used herein refers to the nucleic acid molecule generated during an amplification procedure that is complementary or homologous to a sequence contained within the target sequence. This complementary or homologous sequence of an amplicon is sometimes referred to herein as a "target-specific sequence." Amplicons can be double stranded or single stranded and can include DNA, RNA or both. For example, DNA-dependent RNA polymerase transcribes single stranded amplicons from double stranded DNA during transcription-mediated amplification procedures. These single stranded amplicons are RNA amplicons and can be either strand of a double stranded complex; depending on how the amplification oligomers are designed. Thus, amplicons can be single stranded RNA. RNA-dependent DNA polymerases synthesize a DNA strand that is complementary to an RNA template. Thus, amplicons can be double stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double stranded DNA. RNA-dependent RNA polymerases synthesize RNA from an RNA template. Thus, amplicons can be double stranded RNA. DNA Dependent RNA polymerases synthesize RNA from double stranded DNA templates, also referred to as transcription. Thus, amplicons can be single stranded RNA Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons; all within the spirit of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers, and molecular beacons. An amplification oligomer may contain a sequence that is not complementary to the target or template sequence; for example, the 5' region of a primer may include a promoter sequence that is non-complementary to the target nucleic acid (referred to as a "promoter-primer"). Those skilled in the art will understand that an amplification oligomer that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

Assays of the present invention detect human parvovirus present in a biological sample (e.g., blood, serum, plasma, sputum, bronchial lavage). In one embodiment, the assay detected parvovirus and/or HAV target nucleic acids in plasma samples that are from individual donors, or from a pooled collection of donor samples. To prepare plasma specimens, whole blood samples were centrifuged using standard methods, and the plasma was stored at 4.deg. C. or −20.deg. C. before testing. To lyse viral particles in the specimen, a lysing reagent containing a detergent was mixed with the specimen to release the target nucleic acids from viral particles. Specimen processing may combine viral lysis with purification of the viral target nucleic acids by including a capture oligomer and immobilized oligomer in the lysing reagent. Then the method includes a target capture step in which the target nucleic acids are hybridized specifically to the capture oligomers, which are then hybridized to immobilized oligomers, and each bound complex (i.e., immobilized oligomer, capture oligomer, and target nucleic) is substantially separated from other sample components. Washing the solid support with the bound parvovirus-containing complex washes residual sample components away. Thus, the target nucleic acid is separated from other sample components and concentrated in the bound complexes, without releasing the bound target nucleic acid from the solid support.

Typical sample processing involved the following steps (described in detail in U.S. Pat. No. 6,110,678, International App. Pub. No. WO 2008/016988 and US App. No. 2006/0068417). Viral particles in body fluid (e.g., 0.5 ml of plasma) were lysed upon contact at 60.deg. C. with target capture reagent (790 mM HEPES, 680 mM LiOH, 10% lithium lauryl sulfate (LLS), 230 mM succinate, at least one capture probe at 7 pm/ml, and 100 µg/ml of poly-dT14 bound to magnetic particles (SERADYN™, Indianapolis, Ind.)). Capture oligomers comprised a 5' target-binding region sequence. Capture oligomers further comprised homopolymer or non-homopolymer 3' tail sequence that hybridizes to the complementary oligomer attached to the solid support (e.g., an oligo-dT attached to a solid support and an oligo-dA tail portion of a capture oligomer). Target capture hybridization occurs in this reaction mixture by incubating the mixture at a first temperature (60.deg. C.), allowing the capture oligomer to bind specifically to its complementary target sequence in a target nucleic acid. Then, the mixture was cooled to 40.deg. C. or lower (e.g., room temperature) to allow the 3' tail of the capture oligomer to hybridize to its complementary oligomer on the particle. Following the second hybridization, the mixture is treated to separate the solid support with its bound complex of nucleic acids from the other sample components, e.g., by using gravitational, centrifugal, or magnetic separation. Generally, separation employed a rack containing a magnet to pull the magnetic particles with bound nucleic acid complexes to the side of the tube. Then the supernatant was removed and the bound complexes on the particles were washed with 1 ml of a washing buffer (10 mM HEPES, 6.5 mM NaOH, 1 mM EDTA, 0.3% (v/v) absolute ethanol, 0.02% (w/v) methyl paraben, 0.01% (w/v) propyl paraben, 150 mM NaCl, 0.1% sodium dodecyl sulfate (SDS), pH 7.5) by suspending the magnetic particles in washing buffer, separating particles to the tube side, and removing the supernatant.

Following sample preparation, amplification of the hepatitis A virus and/or parvovirus target nucleic acid was achieved by using amplification oligomers that define the 5' and 3' ends of the region amplified by in vitro enzyme-mediated nucleic acid synthesis to generate an amplicon. One embodiment uses a transcription-mediated amplification (TMA) method, substantially as described in U.S. Pat. Nos. 5,399,491 and 5,554,516, which is a substantially isothermal system that produces a large number of amplification products (RNA transcripts) that can be detected. Preferred embodiments of the method used mixtures of amplification oligomers in which at least one promoter primer is combined with at least one primer.

A preferred embodiment of amplification oligomer combinations comprises a primer oligomer member and a promoter-based oligomer member. Preferably, a promoter-based amplification oligomer is a promoter primer comprising a 5' RNA polymerase promoter sequence and a 3' target binding sequence. RNA polymerase promoter sequences are known in the art to include, but not be limited to, sp6 RNA polymerase promoter sequences, T3 RNA polymerase promoter sequences and T7 RNA polymerase promoter sequences. In the preferred embodiments, a promoter primer comprises a 5' T7 RNA polymerase promoter sequence and a 3' target binding sequence. Most preferably, the 5' T7 RNA polymerase promoter sequence is SEQ ID NO:196.

In one preferred embodiment, the 3' target binding sequence of a promoter-based amplification oligomer is from about 10 to about 40 nucleobases in length and comprises a nucleic acid sequence that is configured to specifically hybridize to a region within a target sequence of a human parvovirus nucleic acid or a hepatitis A virus target nucleic acid. Other preferred promoter primers comprise an internal tag sequence, which is flanked on its 5' end by a promoter sequence and on its 3' end by a target binding sequence. Internal tag sequences are also referred to herein as insert sequences. An internal tag sequence is any nucleic acid sequence that preferably does not stably hybridize with the target nucleic acid or interfere with the target binding sequence hybridizing with the target nucleic acid. Moreover, an internal tag sequence is preferably of a sufficient length and composition such that once incorporated into an amplification product, a tag-specific amplification oligomer can be used to participate in subsequent rounds for generating amplification product. One preferred tag sequence is from about 10 nucleotides in length to about 50 nucleotides in length. Moreover, it is recognized that insert sequences can be included with any of the promoter-based oligomer members of the current invention.

In a preferred embodiment, the amplification oligomer combination comprises at least one primer amplification oligomer member. Preferred primer amplification oligomers have a length that is from about 10 nucleobases to about 50 nucleobases, and have a nucleotide composition configured to specifically hybridize with hepatitis A virus or human parvovirus types 1, 2 and 3 to generate a detectable amplification product when used in an amplification reaction of the current invention. One preferred primer oligomer is from about 10 to about 50 nucleobases in length. Primer oligomer members of the current invention are described herein. These descriptions need not be repeated here. Other preferred primer oligomer members comprise a 5' tag sequence. A 5' tag sequence is any nucleic acid sequence that preferably does not stably hybridize with the target nucleic acid or interfere with the target binding sequence hybridizing with the target nucleic acid. Moreover, a 5' tag sequence is preferably of a sufficient length and composition such that once incorporated into an amplification product, a tag-specific amplification oligomer can be used to participate in subsequent rounds for generating amplification product. One preferred 5' tag sequence is from about 10 nucleotides in length to about 50 nucleotides in length. Another preferred tag sequence is about 12 nucleotides in length. Moreover, it is recognized that 5' tag sequences can be included with any of the primer oligomer members of the current invention.

Amplifying the target nucleic acid by transcription-mediated amplification produces many strands of nucleic acid from a single copy of target nucleic acid, thus permitting detection of the target by detecting probes that hybridize to the sequences of the amplification product. Generally, the reaction mixture includes the target nucleic acid and at least two amplification oligomers comprising at least one primer, at least one promoter primer, reverse transcriptase and RNA polymerase activities, nucleic acid synthesis substrates (deoxyribonucleoside triphosphates and ribonucleoside triphosphates) and appropriate salts and buffers in solution to produce multiple RNA transcripts from a nucleic acid template. Briefly, a promoter-primer hybridizes specifically to a portion of the target sequence. Reverse transcriptase that includes RNase H activity creates a first strand cDNA by 3' extension of the promoter-primer. The cDNA is hybridized with a primer downstream from the promoter primer and a new DNA strand is synthesized from the 3' end of the primer using the reverse transcriptase to create a dsDNA having a functional promoter sequence at one end. RNA polymerase binds to dsDNA at the promoter sequence and transcribes multiple transcripts or amplicons. These amplicons are further used in the amplification process, serving as a template for a new round of replication, to ultimately generate large amounts of single-stranded amplified nucleic acid from the initial target sequence (e.g., 100 to 3,000 copies of RNA synthesized from a single template). The process uses substantially constant reaction conditions (i.e., substantially isothermal). A typical 100 µl amplification reaction uses 75 µl of an amplification reagent mixture (11.6 mM Tris Base, 15.0 mM Tris-HCl, 22.7 mM MgCl$_2$, 23.3 mM KCl, 3.33% glycerol, 0.05 mM Zn-acetate (dihydrate), 0.665 mM each of dATP, dCTP, dGTP, and dTTP, 5.32 mM each of ATP, CTP, GTP, and UTP, pH 7) and 25 µl of an enzyme reagent mixture (700 U of T7 RNA polymerase, 1400 U of reverse transcriptase from Moloney Murine Leukemia Virus (MMLV-RT), 16 mM HEPES (free acid, dihydrate), 70 mM N-acety-L-cysteine, 3 mM EDTA, 0.05% (w/v) Na-azide, 20 mM Tris base, 50 mM KCl, 20% (v/v) anhydrous glycerol, 10% (v/v) TRITON® X-102, and 150 mM trehalose (dihydrate), pH 7), preferably mixed with the captured target nucleic acid retained on the solid particles. For the enzymatic activities, 1 U of T7 RNA polymerase incorporates 1 nmol of ATP into RNA in 1 hr at 37.deg. C. using a DNA template containing a T7 promoter, and 1 U of MMLV-RT incorporates 1 nmol of dTTP into DNA in 10 min at 37.deg. C. using 200-400 μmol oligo dT-primed poly(A) as a template. Amplification oligomers are in the range of about 5-20 pmoles/reaction, or more typically about 7-15 pmoles/reaction, or more typically about 5-15 pmoles/reaction or more typically from about 5-10 pmolex/reaction, these ranges including all whole and partial numbers therein.

In one preferred embodiment, a TMA reaction is performed using a combination of amplification oligomers, wherein said combination comprises at least one promoter primer oligomer member and at least one primer oligomer member, and wherein said combination is configured to generate amplification products for the detection of hepatitis A virus and/or human parvovirus types 1, 2 and 3. In one particular aspect, a TMA reaction is performed that uses at least one hepatitis A virus non-T7 amplification oligomer (SEQ ID NOs:1-11) and at least one hepatitis A virus promoter-based amplification oligomer (SEQ ID NOs: 12-28). In one particular aspect, a TMA reaction is performed that uses at least one parvovirus non-T7 amplification oligomer (SEQ ID NOs:75-87) and at least one parvovirus promoter-based amplification oligomer (SEQ ID NOs: 88-107). In one particular aspect, a multiplex TMA reaction is performed that uses at least one hepatitis A virus non-T7 amplification oligomer (SEQ ID NOs:1-11) and at least one hepatitis A virus promoter-based amplification oligomer (SEQ ID NOs: 12-28). In one particular aspect, a multiplex TMA reaction is performed that uses at least one parvovirus non-T7 amplification oligomer (SEQ ID NOs:75-87) and at least one parvovirus promoter-based amplification oligomer (SEQ ID NOs: 88-107). In one particular aspect, a multiplex TMA reaction is performed that uses at least one parvovirus non-T7 amplification oligomer (SEQ ID NOs:75-87), at least one parvovirus promoter-based amplification oligomer (SEQ ID NOs: 88-107), at least one hepatitis A virus non-T7 amplification oligomer (SEQ ID NOs:1-11) and at least one hepatitis A virus promoter-based amplification oligomer (SEQ ID NOs: 12-28). In an aspect of this embodiment, the amplification oligomer combination comprises at least one promoter primer oligomer member comprising a 5' promoter sequence, an internal tag sequence and a 3' target binding sequence. In an aspect of this embodiment, the amplification oligomer combination comprises at least one promoter primer oligomer member comprising a 5' promoter sequence, an internal tag sequence and a 3' target binding sequence, and also comprises at least one promoter primer oligomer member comprising a 5' promoter sequence and a 3' target binding sequence. In an aspect of this embodiment, the amplification oligomer combination comprises at least one primer oligomer member comprising a 5' tag sequence and a 3' target binding sequence. In an aspect of this embodiment, the amplification oligomer combination comprises at least one primer oligomer member comprising a 5' tag sequence and a 3' target binding sequence, and also comprises at least one primer oligomer member comprising a 3' target binding sequence.

In another preferred embodiment, the TMA reaction is performed with an amplification oligomer combination comprising at least one promoter primer oligomer member and at least one primer oligomer member, wherein configured to generate amplification products for the detection of human parvovirus types 1, 2 and 3 and/or comprising at least one promoter primer oligomer member and at least one primer oligomer member, wherein configured to generate amplification products for the detection of hepatitis A virus. In one embodiment, the TMA reaction for parvovirus is a quantitative amplification and detection reaction. In one embodiment the TMA reaction for hepatitis A virus is a quantitative amplification and detection reaction. In one embodiment, the TMA reaction for parvovirus and the TMA reaction for hepatitis A virus are quantitative amplification and detection reactions. In one aspect, these amplification reactions are multiplex amplification reactions, and detection of amplification products are performed in a detection step that uses one or more detection probes at SEQ ID NOs:58-74 and/or one or more detection probes at SEQ ID NOs:137-169. In one aspect, the amplification reactions are singleplex amplification reactions, and detection of amplification products are performed in a detection step that uses one or more detection probes at SEQ ID NOs:58-74 or one or more detection probes at SEQ ID NOs:137-169.

Either after or during the amplification reaction, the amplified sequences generated from the hepatitis A virus target nucleic acid and/or from the parvovirus target nucleic acid are detected, preferably by hybridization with at least one labeled nucleic acid probe that hybridizes specifically to a portion of the amplified sequence. Probe embodiments include those having a $T_m$ in the range of about 80.deg. C. to about 85.deg. C. Some preferred probe embodiments include oligomers having a nucleotide length of from about 15 to about 40 nucleotides and a nucleic acid sequence that is DNA, RNA or a combination there of and is configured to specifically hybridize with all or a portion of a region of a target sequence of a hepatitis A virus nucleic acid or a human parvovirus nucleic acid or amplified nucleic acid. Detection oligomers of the current invention can further comprise one or more LNA residues. Detection of the probe is accomplished by detecting a label that can be detected in a homogeneous reaction. Therefore, some preferred embodiments further comprise probes labeled with an acridinium ester (AE) compound using well-known methods that allow homogeneous detection (e.g., labels and detection methods are described in detail in U.S. Pat. No. 5,283,174 to Arnold, Jr., et al., U.S. Pat. No. 5,656,207 to Woodhead et al., and U.S. Pat. No. 5,658,737 to Nelson et al.). A chemiluminescent AE compound is attached to the probe sequence via a linker compound (substantially as described in U.S. Pat. Nos. 5,585,481 and 5,639,604 to Arnold, Jr., et al., e.g., see column 10, line 6 to column 11, line 3, and Example 8). In one embodiment, the labeled probe oligomer has at least one 2'-O-methoxy linkage in the nucleic acid backbone. In an embodiment of a typical detection step, the probe reagent included 100 mM succinate, 2% (w/v) LLS, 230 mM LiOH (monohydrate), 15 mM 2,2'-dithiodipyridine (ALDRITHIOL-2), 1.2 M LiCl, 20 mM EDTA, 20 mM EGTA, 3% (v/v) absolute ethanol, brought to about pH 4.7 with LiOH, and the selection reagent used for hydrolyzing the label on unbound probe included 600 mM boric acid, 182 mM NaOH, 1% (v/v) TRITON® X-100. Detection probe is added to the detection reaction at a range from about 1E7-5E7 relative light units (RLU) per reaction, more typically about 1E7-3E7 RLU per reaction, more typically 2E7-5E7 RLU per reaction, or more typically 2E7-4E7 RLU per reaction; wherein eh ranges include all whole and partial numbers therein. The signal was detected as RLU using a luminometer (e.g., LEADER™ 450HC+, Gen-Probe Incorporated, San Diego, Calif.).

To select DNA sequences appropriate for use as capture oligomers, amplification oligomers and detection probes, DNA sequences, including partial or complementary sequences, available from publicly accessible databases (e.g., GenBank) were aligned by matching regions of the same or similar sequences and compared using well known molecular biology techniques. Although sequence comparisons may be facilitated by use of algorithms, those skilled in the art can readily perform such comparisons manually and visually. Generally, portions of sequences that contain relatively few variants between the compared sequences were chosen as a basis for designing synthetic oligomers for use in the present invention. Other considerations in designing oligomers included the relative GC content (which affects $T_m$) and the relative absence of predicted secondary structure (which potentially form intramolecular hybrids) within a sequence, as determined by using well-known methods.

In one embodiment, the assay is carried out in a single tube using a 0.5 to 1 ml sample of body fluid (e.g., plasma) to detect target nucleic acid at a sensitivity of about 100 to 500 copies/ml of target DNA per reaction. In other embodiments, the assay detected higher numbers of target nucleic acid in the sample, which may be a pooled sample of individual samples.

Unless defined otherwise, all scientific and technical terms used herein have the same meaning as commonly understood by those skilled in the relevant art. General definitions of many of the terms used herein are provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and *Taber's Cyclopedic Medical Dictionary*, 17th ed. (F.A. Davis Co., Philadelphia, Pa., 1993). Unless mentioned otherwise, the techniques employed or contemplated herein are standard methodologies well known to one of ordinary skill in the art. The following examples illustrate some of the preferred embodiments of the invention and are provided for illustration only.

Example 1

Amplification of an HAV Target Using a Primer and a Promoter Provider and without Using Target Capture A hepatitis A virus amplification assay was set up using 1.25 IU of HAV per reaction and one of two amplification conditions: SEQ ID NO:2 and SEQ ID NO:18, or SEQ ID NO:2 and SEQ ID NO:13. Detection of amplification product was performed using a separating gel and ethidium bromide stain. The assays were set up by making a serial dilution of a stock of HAV target (WHO First International Standard from the National Institute for Biologic Standards and Controls (NIBSC #00/560, at 5E4 IU per vial)), and then the dilutions were added to separate wells of a 96-well plate. Each of the two amplification conditions was then added to separate wells containing a dilution. An isothermal amplification reaction was performed and at the end of the reaction, an aliquot of each reaction was transferred to a separate well of a gel and then stained with EtBr. The results of this study showed that each amplification condition detected as few as 1.25 IU of hepatitis A virus nucleic acids.

Example 2

Amplification of an HAV Target Using a Primer and a Promoter PROVIDER and Using Target Capture A hepatitis A virus amplification assay was set up as in Example 1, except that the assay included an initial target capture step of the different dilutions and except that detection of amplification product was done using a detection probe (SEQ ID NO:62). The assays were set up by first capturing the HAV target from each of the separate diluting and adding the captured HAV target nucleic acids to separate wells on a 96-well plate. The target capture oligomers used were from a pool of oligomer having a dT3dA30 tail and a K18 target capture region. The target capture regions of the target capture oligomers were synthesized to each have random assortments of G and U residues, thus the population of target capture oligomers used in this example was a mixed collection of sequences. The detection step was an end-point detection reaction and the results showed that this assay system had a 95% detection of at least 3.87 IU/mL of HAV target nucleic acid (Table 1).

TABLE 1

| 3-fold serial dilution | | | 2-fold serial dilution | | |
|---|---|---|---|---|---|
| IU/mL | Number of wells | Number of reactive wells | IU/mL | Number of wells | Number of reactive wells |
| 9 | 60 | 60 | 8 | 30 | 30 |
| 3 | 60 | 57 | 4 | 30 | 30 |
| 1 | 60 | 35 | 2 | 30 | 26 |
| 0.33 | 60 | 19 | 1 | 30 | 12 |
| 0.11 | 60 | 5 | 0.5 | 30 | 10 |
| 0 | 60 | 0 | 0 | 30 | 0 |

This experiment shows that using a non-specific target capture system combined with the amplification and detection condition provides a sensitive amplification and detection of HAV target nucleic acids, though amplification and detection was not as sensitive as seen for Example 1 wherein a known amount of target was added directly to the amplification reaction.

Example 3

Amplification of Parvovirus Genotypes 1, 2 & 3 Using a Primer and a Promoter Provider and Using Target Capture An amplification reaction was set up to test a plurality of amplification oligomer combinations for amplification of parvovirus genotype 1 at varying concentrations. The amplification assay was set up with all of the combinations of non-T7 amplification oligomer and T7 amplification oligomer that could be made from the following: combine each one of SEQ ID NOs:75-87 with each one of SEQ ID NOs:88-99, wherein each combination is just a single non-T7 and a single T7. Each amplification oligomer was designed to amplify parvovirus genotypes 1, 2 and 3. Target Nucleic Acid was SEQ ID NO:203. The stock nucleic acid was diluted and added to wells of reaction plates at 0 copies per reaction, 10 copies per reaction, 100 copies per reaction and 100,000 copies per reaction. Primerless amplification reagent was prepared as generally described above and added to each well of each reaction plate for the 0, 10, 100 and 100,000 copy reactions. The various primer conditions from the above combinations of Non-T7 and T7 amplification oligomers were added to separate wells on these plates. The amplification reaction was isothermal and included initial incubation steps at about 62 deg C. and about 42 deg C. for 10 and 20 minutes, respectively, followed by a 50 minute amplification at 42 deg C. in the presence of polymerase. Detection of amplification product was performed using SEQ ID NO:145 and a Leader HC luminometer. RLU detected for the plate having 0 copies of parvovirus was from 934 RLU to 14698 RLU. RLU detected for the plate having 10 copies of parvovirus per reaction was from 2,015 RLU to 8,040,373 RLU, with over half of the combinations providing a signal well above background. RLU detected for the plate having 100 copies of parvovirus per reaction was from 2,439 RLU to 8,114,133 RLU. RLU detected for the plate having 100,000 copies of parvovirus per reaction was from 495,680 RLU to 8,308,252 RLU. From the results of these assays, a number of combinations of amplification oligomers were identified that are useful for a parvovirus amplification reaction that amplifies as few as 10 copies of parvovirus.

A further assay was set up for the amplification and detection of each of parvovirus genotypes 1, 2 and 3. These amplification reactions used the following amplification oligomer conditions: SEQ ID NOs:80 & 92; SEQ ID NOs: 80 & 91; and SEQ ID NOs: 81 & 92, each of which are designed for amplification of the three parvovirus genotypes. Target nucleic acids were in vitro transcripts of a portion of each parvovirus genotype 1-3 (SEQ ID NOs: 200, 201 & 202, respectively) and were provided into the assay as a serial dilution from a sock concentration. Target capture was performed using the non-specific target capture system discussed in Example 2. Detection was an end-point detection using SEQ ID NO:146. The results of this amplification and detection assay showed that the three systems had consistent sensitivity down to at least 80 copies of target per mL, and had good sensitivity down to 5 copies/mL though there were variations in detection between the three genotypes (e.g., at 5 copies per mL, 40% of the wells with genotype 1 were reactive whereas only about 20% of the genotype 3 wells were reactive).

A further amplification reaction was performed for the amplification and detection of parvovirus nucleic acids wherein the amplification oligomer combination included a non-T7 amplification oligomer and two T7 amplification oligomers. The combinations of amplification oligomers were as follows: SEQ ID NOs:80, 90 & 99; SEQ ID NOs:80, 91 & 99; SEQ ID NOs:80, 92 & 99; SEQ ID NOs:81, 90 & 99, SEQ ID NOs:81, 91 & 99; SEQ ID NOs:81, 92 & 99; SEQ ID NOs:82, 90 & 99; SEQ ID NOs:82, 91 & 99; and SEQ ID NOs:82, 92 & 99. The amplification and detection reactions were set-up as generally described above, and each reaction was performed in 10 wells. The target nucleic acid was SEQ ID NO:203. The results showed that SEQ ID NOs:80, 90 & 99; SEQ ID NOs:80, 91 & 99; SEQ ID NOs:80, 92 & 99; and SEQ ID NOs:81, 91 & 99 all detected down to 50 copies of target nucleic acids at 100% reactivity for the wells, while the other combinations were from about 80% reactive to non-reactive.

Combinations SEQ ID NOs:80, 91 & 99; SEQ ID NOs: 80, 92 & 99 and SEQ ID NOs:82, 90 & 99 were then tested against SEQ ID NOs: 200-202, each target nucleic acid being provided at 45 copies per reaction, 15 copies per reaction and 5 copies per reaction. Each reaction condition was tested in 10 separate wells. Amplification and detection reactions were set up as is generally described above. All three amplification oligomer combinations were 100% reactive for detecting 45 copies of each parvovirus genotype. The three amplification oligomer combinations were from 100% reactive to 70% reactive detecting 15 copies of the three parvovirus genotypes. The three amplification oligomer combinations were from 70% reactive to 40% reactive detecting 5 copies of the three parvovirus genotypes. Thus, the combinations of parvovirus amplification oligomers were able to detect as few as 5 copies of each genotype with about 40%-70% efficiency.

Example 4

Amplification and Detection of Hepatitis a Virus in the Presence of Parvovirus

An amplification assay was performed to amplify and detect hepatitis A virus target nucleic acids in the presence of parvovirus nucleic acids. The HAV target nucleic acid was the WHO standard described in Example 1. A serial dilution of the HAV standard was made and each dilution was added to separate wells on a 96-well plate. 5E6 copies of SEQ ID NO:200 was spiked into each well. An HAV amplification reaction mixture was prepared to include from 5-10 pM/rxn of SEQ ID NOs:2 & 18. An end-point detection reaction mixture was prepared to include 5E6 RLU per reaction of SEQ ID NO:62. The amplification reaction was performed and then the reaction was stopped and the detection reaction was performed. The results from this assay show that 100% of the wells containing as low as 40 copies of HAV and 90% of the wells containing as low as 20 copies of HAV were detected in the presence of 5E6 copies of parvovirus.

Example 5

Quantitative Amplification and Detection of Parvovirus Target Nucleic Acids

A quantitative assay for the amplification and detection of parvovirus genotypes 1, 2 and 3 was performed. The parvovirus target nucleic acids were nucleic acids from the WHO International Reference Panel for Parvovirus B19 Genotypes (NIBSC 99/800 which is 5.98 log 10 IU/mL genotype 1, 5.94 log 10 IU/mL genotype 2, 5.97 log 10 IU/mL genotype 3 wherein an IU is about 0.12 copies of each genotype). The parvovirus target nucleic acids were diluted down to 10,000 IU/mL and 1,000 IU/mL and each of the dilutions was added to different wells of separate 96-well plates. The parvovirus amplification oligomer were SEQ ID NOs:91 & 131. The detection probe oligomer was SEQ ID NO:144. A parvovirus competitor sequence (SEQ ID NO:197) was spiked into the amplification reaction mix. Results are shown in Table 2.

TABLE 2

| Concentration of Target | Target Nucleic Acid | Number of wells | Predicted Log (IU/mL) | Observed Log (IU/mL) | SD |
|---|---|---|---|---|---|
| 1,000 IU/mL | Genotype 1 | 29 | 3.0 | 3.97 | 0.08 |
| 1,000 IU/mL | Genotype 2 | 29 | 3.0 | 3.69 | 0.38 |
| 1,000 IU/mL | Genotype 3 | 30 | 3.0 | 3.61 | 0.12 |
| 10,000 IU/mL | Genotype 1 | 30 | 4.0 | 4.93 | 0.07 |

TABLE 2-continued

| Concentration of Target | Target Nucleic Acid | Number of wells | Predicted Log (IU/mL) | Observed Log (IU/mL) | SD |
|---|---|---|---|---|---|
| 10,000 IU/mL | Genotype 2 | 30 | 4.0 | 4.68 | 0.15 |
| 10,000 IU/mL | Genotype 3 | 30 | 4.0 | 4.63 | 0.05 |

These results show that the current quantitative assay shows good linearity with the WHO standard target nucleic acids, though the genotype 2 assay quantified with a relatively higher variation from standard.

Example 6

Quantitative Amplification and Detection of Parvovirus Target Nucleic Acids Spiked into Parvovirus Negative Human Plasma Samples his quantitative amplification and detection assay was set up according to Example 5, above, except that 10,000 IU/1M of the target nucleic acids were resuspended in human plasma from donors determined to be negative for parvovirus. The expected amount of parvovirus detected in each sample was 4 Log(copies/mL), and the observed average results were 3.92(±0.059) Log(copies/mL). Thus, the quantitative parvovirus assay provides accurate results amplifying and detecting all parvovirus target nucleic acids in human plasma samples.

Example 7

Amplification and Detection of Hepatitis a Virus Nucleic Acids and Parvovirus Target Nucleic Acids Using Specific Target Capture An amplification and detection reaction was performed on target nucleic acids that were separated from a sample using target-specific target capture oligomers. The target capture oligomers for capture of hepatitis A virus nucleic acids are SEQ ID NOs:46-51, and the target capture oligomers for the capture of parvovirus nucleic acids are SEQ ID NOs:128-131. Target capture oligomers were used singly and in combinations (meaning two or more target capture oligomers targeting hepatitis A virus or two or more target capture oligomers targeting parvovirus) in a target capture reaction. Samples and reaction conditions were as described above for the hepatitis A virus singleplex reactions and for the parvovirus singleplex reactions. The single and combinations of specific target capture oligomers demonstrated improved sensitivity and capture efficiency compared to the non-specific target capture methods.

TABLE 3

Exemplary Oligomers, Reference Sequences and Regions

| SEQ ID NO: | Sequence | Description |
|---|---|---|
| 1 | CAGAGAATTATGAAAGTGGA | HAV Non-T7 amp oligo |
| 2 | AGTCAGAGAATTATGAAAGTGGA | HAV Non-T7 amp oligo |
| 3 | UGAGAGTCAGAGAATTATGAAAGTGGA | HAV Non-T7 amp oligo |
| 4 | AGTCAGAGAATTATGAAAGTGG | HAV Non-T7 amp oligo |
| 5 | CAGAGAATTATGAAAGTGG | HAV Non-T7 amp oligo |
| 6 | TGAGAGTCAGAGAATTATGAAAGTGG | HAV Non-T7 amp oligo |
| 7 | TCAGTGTTCAATGAATGT | HAV Non-T7 amp oligo |
| 8 | TTTACTCAGTGTTCAATGAATGT | HAV Non-T7 amp oligo |
| 9 | GGAGTTTACTCAGTGTTCAATGAATGT | HAV Non-T7 amp oligo |
| 10 | ATGAAAGTGGAGTTTACTCAGTGTTCAATGAATGT | HAV Non-T7 amp oligo |
| 11 | GAAAGTCAGAGAATAATGAAAGT | HAV Non-T7 amp oligo |
| 12 | AATTTAATACGACTCACTATAGGGAGAGGAAAATTAATCATGGTTTTATCAATGTG | HAV T7 amp oligo |
| 13 | AATTTAATACGACTCACTATAGGGAGAGGAAAATTAATCATGGTTTTITCAATGTG | HAV T7 amp oligo |
| 14 | AATTTAATACGACTCACTATAGGGAGAGCAGGAAAATTAATCATG | HAV T7 amp oligo |
| 15 | AATTTAATACGACTCACTATAGGGAGAGCAGGAAAATTAATCAT | HAV T7 amp oligo |
| 16 | AATTTAATACGACTCACTATAGGGAGAGCAGGAAAATTAATCA | HAV T7 amp oligo |
| 17 | AATTTAATACGACTCACTATAGGGAGAGCAGGAAAATTAATC | HAV T7 amp oligo |

TABLE 3-continued

Exemplary Oligomers, Reference Sequences and Regions

| SEQ ID NO: | Sequence | Description |
|---|---|---|
| 18 | AATTTAATACGACTCACTATAGGGAGAGGCATAGCTGCAGGAAAATTAATCATG | HAV T7 amp oligo |
| 19 | AATTTAATACGACTCACTATAGGGAGAGGCATAGCTGCAGGAAAATTAATCAT | HAV T7 amp oligo |
| 20 | AATTTAATACGACTCACTATAGGGAGAGGCATAGCTGCAGGAAAATTAATCA | HAV T7 amp oligo |
| 21 | AATTTAATACGACTCACTATAGGGAGAGGCATAGCTGCAGGAAAATTAATC | HAV T7 amp oligo |
| 22 | AATTTAATACGACTCACTATAGGGAGAACTCTTTCTAAAAAGCGTTTTGGAGAC | HAV T7 amp oligo |
| 23 | AATTTAATACGACTCACTATAGGGAGATCTTTCTAAAAAGCGTTTTGGAGAC | HAV T7 amp oligo |
| 24 | AATTTAATACGACTCACTATAGGGAGAACTCTTTCTAAAGAGCGTTTTGGAGAC | HAV T7 amp oligo |
| 25 | AATTTAATACGACTCACTATAGGGAGATCTTTCTAAAGAGCGTTTTGGAGAC | HAV T7 amp oligo |
| 26 | AATTTAATACGACTCACTATAGGGAGAACTCTTTCTAAAAAGCGTTTTGGAG | HAV T7 amp oligo |
| 27 | AATTTAATACGACTCACTATAGGGAGAACTCTTTCTAAAGAGCGTTTTGGAG | HAV T7 amp oligo |
| 28 | AATTTAATACGACTCACTATAGGGAGAggaaaattaatcatggttttatcaatgt | HAV T7 amp oligo |
| 29 | GGAAAATTAATCATGGTTTTATCAATGTG | Target hybridizing sequence of SEQ ID NO: 12 |
| 30 | GGAAAATTAATCATGGTTTTNTCAATGTG [N is inosine] | Target hybridizing sequence of SEQ ID NO: 13 |
| 31 | GCAGGAAAATTAATCATG | Target hybridizing sequence of SEQ ID NO: 14 |
| 32 | GCAGGAAAATTAATCAT | Target hybridizing sequence of SEQ ID NO: 15 |
| 33 | GCAGGAAAATTAATCA | Target hybridizing sequence of SEQ ID NO: 16 |
| 34 | GCAGGAAAATTAATC | Target hybridizing sequence of SEQ ID NO: 17 |
| 35 | GGCATAGCTGCAGGAAAATTAATCATG | Target hybridizing sequence of SEQ ID NO: 18 |
| 36 | GGCATAGCTGCAGGAAAATTAATCAT | Target hybridizing sequence of SEQ ID NO: 19 |
| 37 | GGCATAGCTGCAGGAAAATTAATCA | Target hybridizing sequence of SEQ ID NO: 20 |
| 38 | GGCATAGCTGCAGGAAAATTAATC | Target hybridizing sequence of SEQ ID NO: 21 |

TABLE 3-continued

Exemplary Oligomers, Reference Sequences and Regions

| SEQ ID NO: | Sequence | Description |
|---|---|---|
| 39 | ACTCTTTCTAAAAAGCGTTTTGGAGAC | Target hybridizing sequence of SEQ ID NO: 22 |
| 40 | TCTTTCTAAAAAGCGTTTTGGAGAC | Target hybridizing sequence of SEQ ID NO: 23 |
| 41 | ACTCTTTCTAAAGAGCGTTTTGGAGAC | Target hybridizing sequence of SEQ ID NO: 24 |
| 42 | TCTTTCTAAAGAGCGTTTTGGAGAC | Target hybridizing sequence of SEQ ID NO: 25 |
| 43 | ACTCTTTCTAAAAAGCGTTTTGGAG | Target hybridizing sequence of SEQ ID NO: 26 |
| 44 | ACTCTTTCTAAAGAGCGTTTTGGAG | Target hybridizing sequence of SEQ ID NO: 27 |
| 45 | ggaaaattaatcatggttttatcaatgt | Target hybridizing sequence of SEQ ID NO: 28 |
| 46 | GGUCCCUCUGAAAUUAACAUUGGUGUUCCAAAAAAAAAAAAAAAAAAAAAAAAAAA | HAV Target capture oligo |
| 47 | GUUCCAUCAUUCUUUUUAUGAACAUUUAAAAAAAAAAAAAAAAAAAAAAAAAAAA | HAV Target capture oligo (20BT3A30) |
| 48 | CCUUCGCCUUUUCCUCUCCAUGCCUGAUCUUUAAAAAAAAAAAAAAAAAAAAAAAAAAAA | HAV Target capture oligo |
| 49 | UCGCCUUUUCCUCUCCAUGCCUGAUCUUUAAAAAAAAAAAAAAAAAAAAAAAAAAA | HAV Target capture oligo |
| 50 | CCUUCGCCUUUUCCUCUCCAUGCCUGUUUAAAAAAAAAAAAAAAAAAAAAAAAAAAA | HAV Target capture oligo |
| 51 | GGCCCCACCACACAUUCCAGGAAGUUUAAAAAAAAAAAAAAAAAAAAAAAAAAAA | HAV Target capture oligo |
| 52 | GGUCCCUCUGAAAUUAACAUUGGUGUUCC | Target hybridizing sequence of SEQ ID NO: 46 |
| 53 | GUUCCAUCAUUCUUUUUAUGAACA | Target hybridizing sequence of SEQ ID NO: 47 |
| 54 | CCUUCGCCUUUUCCUCUCCAUGCCUGAUC | Target hybridizing sequence of SEQ ID NO: 48 |
| 55 | UCGCCUUUUCCUCUCCAUGCCUGAUC | Target hybridizing sequence of SEQ ID NO: 49 |
| 56 | CCUUCGCCUUUUCCUCUCCAUGCCUG | Target hybridizing sequence of SEQ ID NO: 50 |
| 57 | GGCCCCACCACACAUUCCAGGAAG | Target hybridizing sequence of SEQ ID NO: 51 |
| 58 | UCAGUGUUCAAUGAAUGU | HAV Detection probe |
| 59 | UCAGUGUUCAAUGAAUGU | HAV Detection probe |

TABLE 3-continued

Exemplary Oligomers, Reference Sequences and Regions

| SEQ ID NO: | Sequence | Description |
|---|---|---|
| 60 | UCAGUGUUCAAUGAAUGU | HAV Detection probe |
| 61 | UGUUCAAUGAAUGUGGUCUCC | HAV Detection probe |
| 62 | UGUUCAAUGAAUGUGGUCUCC | HAV Detection probe |
| 63 | UGUUCAAUGAAUGUGGUCUCC | HAV Detection probe |
| 64 | GUUCAAUGAAUGUGGUCUCCAAAACGCU | HAV Detection probe |
| 65 | GUUCAAUGAAUGUGGUCUCCAAAACGCU | HAV Detection probe |
| 66 | GAAUGUGGUCUCCAAAACGCU | HAV Detection probe |
| 67 | GAAUGUGGUCUCCAAAACGCT | HAV Detection probe |
| 68 | GAAUGUGGUCUCCAAAACGCT | HAV Detection probe |
| 69 | GUGGUCUCCAAAACGCUUUUUAGA | HAV Detection probe |
| 70 | GUGGUCUCCAAAACGCUUUUUAGA | HAV Detection probe |
| 71 | GUGGUCUCCAAAACGCUUUUUAGA | HAV Detection probe |
| 72 | GUGGUCUCCAAAACGCUUUUUAGA | HAV Detection probe |
| 73 | GUGGUCUCCAAAACGCUUUUUAGA | HAV Detection probe |
| 74 | GUCUCCAAAACGCUUUUUAG | HAV Detection probe |
| 75 | CCAGTANCAGTNA | (91AE6) Parvo Non-T7 amp oligo Independently, N is either G or I |
| 76 | TCATCCAGTAGCAGTG | Parvo Non-T7 amp oligo |
| 77 | TCACCCAGTAACAG | Parvo Non-T7 amp oligo |
| 78 | TCTGACCACCCCATGCCTTATCA | Parvo Non-T7 amp oligo |
| 79 | CTGACCACCCCATGCCTTATCA | Parvo Non-T7 amp oligo |
| 80 | CCACCCCATGCCTTATCA | Parvo Non-T7 amp oligo |
| 81 | GGACAGTTATCTGACCACCCCAT | Parvo Non-T7 amp oligo |
| 82 | CATGGACAGTTATCTGACCACC | Parvo Non-T7 amp oligo |
| 83 | CATCATTTTCAAAGTCATGGACAG | Parvo Non-T7 amp oligo |
| 84 | CATCATTTTCAGAGTCATGGACAG | Parvo Non-T7 amp oligo |
| 85 | CTCTCCAGACTTATATAGTCAT | Parvo Non-T7 amp oligo |
| 86 | CCTCTCTGTTTGACTTAGTTGCTC | Parvo Non-T7 amp oligo |
| 87 | CCTCTTTGTTTGACTTAGTTGCTC | Parvo Non-T7 amp oligo |
| 88 | AATTTAATACGACTCACTATAGGGAGAGCTAACTTGCCCAGGCTTGTGT | Parvo T7 amp oligo |
| 89 | AATTTAATACGACTCACTATAGGGAGAACGCTAACTTGCCCAGGCTTGTGT | Parvo T7 amp oligo |
| 90 | AATTTAATACGACTCACTATAGGGAGAGTTGTACGCTAACTTGCCCAGGCTTGTGT | Parvo T7 amp oligo |
| 91 | AATTTAATACGACTCACTATAGGGAGAGCTAACTTGCCCAGGCTTGTG | Parvo T7 amp oligo |
| 92 | AATTTAATACGACTCACTATAGGGAGAACGCTAACTTGCCCAGGCTTGTG | Parvo T7 amp oligo |

TABLE 3-continued

Exemplary Oligomers, Reference Sequences and Regions

| SEQ ID NO: | Sequence | Description |
|---|---|---|
| 93 | AATTTAATACGACTCACTATAGGGAGAGTTGTACGCTAACTTGCCCAGGCTTGTG | Parvo T7 amp oligo |
| 94 | AATTTAATACGACTCACTATAGGGAGAAACATAGTTAGTACCGGGTA | Parvo T7 amp oligo |
| 95 | AATTTAATACGACTCACTATAGGGAGACAACATAGTTAGTACCGGGTA | Parvo T7 amp oligo |
| 96 | AATTTAATACGACTCACTATAGGGAGACCAACATAGTTAGTACCGGGTA | Parvo T7 amp oligo |
| 97 | AATTTAATACGACTCACTATAGGGAGATGCGGGGCCCAGCTTGTA | Parvo T7 amp oligo |
| 98 | AATTTAATACGACTCACTATAGGGAGAGGCTATACCTAAAGTCATG | Parvo T7 amp oligo |
| 99 | AATTTAATACGACTCACTATAGGGAGAGGCTATACCTAAAGTCATGA | Parvo T7 amp oligo |
| 100 | AATTTAATACGACTCACTATAGGGAGAGCTATACCTAAAGTCATGA | Parvo T7 amp oligo |
| 101 | AATTTAATACGACTCACTATAGGGAGAACCTAAAGTCATGAATCCTTGCAG | Parvo T7 amp oligo |
| 102 | AATTTAATACGACTCACTATAGGGAGACCAACATAGTTAGTACCGGGGGT | Parvo T7 amp oligo |
| 103 | AATTTAATACGACTCACTATAGGGAGACCAACATAGTTAGTACCGGGGG | Parvo T7 amp oligo |
| 104 | AATTTAATACGACTCACTATAGGGAGACCAACATAGTTAGTACCGGGG | Parvo T7 amp oligo |
| 105 | AATTTAATACGACTCACTATAGGGAGACCAACATAGTTAGTACCGGG | Parvo T7 amp oligo |
| 106 | AATTTAATACGACTCACTATAGGGAGACCAACATAGTTAGTACCGG | Parvo T7 amp oligo |
| 107 | AATTTAATACGACTCACTATAGGGAGACCAACATAGTTAGTACCG | Parvo T7 amp oligo |
| 108 | GCTAACTTGCCCAGGCTTGTGT | Target hybridizing sequence of SEQ ID NO: 88 |
| 109 | ACGCTAACTTGCCCAGGCTTGTGT | Target hybridizing sequence of SEQ ID NO: 89 |
| 110 | GTTGTACGCTAACTTGCCCAGGCTTGTGT | Target hybridizing sequence of SEQ ID NO: 90 |
| 111 | GCTAACTTGCCCAGGCTTGTG | Target hybridizing sequence of SEQ ID NO: 91 |
| 112 | ACGCTAACTTGCCCAGGCTTGTG | Target hybridizing sequence of SEQ ID NO: 92 |
| 113 | GTTGTACGCTAACTTGCCCAGGCTTGTG | Target hybridizing sequence of SEQ ID NO: 93 |
| 114 | AACATAGTTAGTACCGGGTA | Target hybridizing sequence of SEQ ID NO: 94 |

TABLE 3-continued

Exemplary Oligomers, Reference Sequences and Regions

| SEQ ID NO: | Sequence | Description |
|---|---|---|
| 115 | CAACATAGTTAGTACCGGGTA | Target hybridizing sequence of SEQ ID NO: 95 |
| 116 | CCAACATAGTTAGTACCGGGTA | Target hybridizing sequence of SEQ ID NO: 96 |
| 117 | CCAGTANCAG | Amp oligo core sequence. SEQ ID NOS: 75-74 contain this N is preferably G or I. |
| 118 | GGCTATACCTAAAGTCATG | Target hybridizing sequence of SEQ ID NO: 98 |
| 119 | GGCTATACCTAAAGTCATGA | Target hybridizing sequence of SEQ ID NO: 99 |
| 120 | GCTATACCTAAAGTCATGA | Target hybridizing sequence of SEQ ID NO: 100 |
| 121 | ACCTAAAGTCATGAATCCTTGCAG | Target hybridizing sequence of SEQ ID NO: 101 |
| 122 | CCAACATAGTTAGTACCGGGGGT | Target hybridizing sequence of SEQ ID NO: 102 |
| 123 | CCAACATAGTTAGTACCGGGGG | Target hybridizing sequence of SEQ ID NO: 103 |
| 124 | CCAACATAGTTAGTACCGGGG | Target hybridizing sequence of SEQ ID NO: 104 |
| 125 | CCAACATAGTTAGTACCGGG | Target hybridizing sequence of SEQ ID NO: 105 |
| 126 | CCAACATAGTTAGTACCGG | Target hybridizing sequence of SEQ ID NO: 106 |
| 127 | CCAACATAGTTAGTACCG | Target hybridizing sequence of SEQ ID NO: 107 |
| 128 | ATGCGAGCAACTAAGTCAAACAGGGAGTTTAAAAAAAAAAAAAAAAAAAAAAAAAAAAA | Parvo Target capture oligo |
| 129 | TGCGGGGCCCAGCTTGTATTTAAAAAAAAAAAAAAAAAAAAAAAAAAAA | Parvo Target capture oligo |
| 130 | TGGCTATACCTAAAGTCATGAATCCTTTTAAAAAAAAAAAAAAAAAAAAAAAAAAAA | Parvo Target capture oligo |
| 131 | AGTACTGAAATCCATATCGGTTGTTTAAAAAAAAAAAAAAAAAAAAAAAAAAA | Parvo Target capture oligo |
| 132 | ATGCGAGCAACTAAGTCAAACAGGGAG | Target hybridizing sequence of SEQ ID NO: 128 |

TABLE 3-continued

Exemplary Oligomers, Reference Sequences and Regions

| SEQ ID NO: | Sequence | Description |
|---|---|---|
| 133 | TGCGGGGCCCAGCTTGTA | Target hybridizing sequence of SEQ ID NO: 97 and SEQ ID NO: 129 |
| 134 | TGGCTATACCTAAAGTCATGAATCCT | Target hybridizing sequence of SEQ ID NO: 130 |
| 135 | AGTACTGAAATCCATATCGGTTG | Target hybridizing sequence of SEQ ID NO: 131 |
| 136 | GAGTATATGGGTTTATTCCCA | Displacer oligo |
| 137 | UACAGAACCUAGAGGAGAAAAUG | Parvo Detection probe |
| 138 | UACAGAACCUAGAGGAGAA | Parvo Detection probe |
| 139 | GAACCUAGAGGAGAAAAUG | Parvo Detection probe |
| 140 | CAGAACCUAGAGGAGAA | Parvo Detection probe |
| 141 | CAGAACCUAGAGGAGAAAAUG | Parvo Detection probe |
| 142 | CgUGCAGAACCUAGAGGAGAA | Parvo Detection probe |
| 143 | CAUACAGAACCUAGAGGAGAA | Parvo Detection probe |
| 144 | AGUACAGAACCUAGAGGAGAA | Parvo Detection probe |
| 145 | UACAGAACCUAGAGGAGAA | Parvo Detection probe |
| 146 | UGCAGAACCUAGAGGAGAA | Parvo Detection probe |
| 147 | AGUGCAGAACCUAGAGGAGAA | Parvo Detection probe |
| 148 | CAGAACCUAGAGGAGAA | Parvo Detection probe |
| 149 | CAGAACCUAGAGGAGAA | Parvo Detection probe |
| 150 | CGUGCAGAACCUAGAGGAGAA | Parvo Detection probe |
| 151 | CGUGCAGAACCUAGAGGAGAA | Parvo Detection probe |
| 152 | CGUGCAGAACCUAGAGGAGAA | Parvo Detection probe |
| 153 | CGUGCAGAACCUAGAGGAGAA | Parvo Detection probe |
| 154 | CGUGCAGAACCUAGAGGAGAA | Parvo Detection probe |
| 155 | CGUACAGAACCUAGAGGAGAA | Parvo Detection probe |
| 156 | CGUGCAGAACCUAGAGGAGGAGAU | Parvo Detection probe |
| 157 | GUGCAGAACCUAGAGGAGAA | Parvo Detection probe |
| 158 | UGCAGAACCUAGAGGAGAA | Parvo Detection probe |
| 159 | GAACCUAGAGGAGAAGAUG | Parvo Detection probe |
| 160 | CAUGCAGAACCUAGAGGAGAA | Parvo Detection probe |
| 161 | CAUGCAGAACCUAGAGGAGAA | Parvo Detection probe |
| 162 | GCAGAACCUAGAGGAGAAAAUG | Parvo Detection probe |
| 163 | GAACCUAGAGGAGAAAAUG | Parvo Detection probe |
| 164 | GAACUUAGAGGAGAAAAUG | Parvo Detection probe |
| 165 | CAGAACCUAGAGGAGAA | Parvo Detection probe |

TABLE 3-continued

Exemplary Oligomers, Reference Sequences and Regions

| SEQ ID NO: | Sequence | Description |
|---|---|---|
| 166 | CAGAACCUAGAGGAGAA | Parvo Detection probe |
| 167 | CAGAACCUAGAGGAGAA | Parvo Detection probe |
| 168 | GAACCUAGAGGAGAAAAUG | Parvo Detection probe |
| 169 | GUAUUAUCUAGUGAAGACUUAC | Parvo Detection probe |
| 170 | CAGAGAATWATGAAAGT | Amp oligo core sequence (SEQ ID NOs: 1-6 & 11 share this) |
| 171 | CAGAGAATWATGAAAGTGG | Amp oligo core sequence (SEQ ID NOs: 1-6 share this) |
| 172 | TGARAGTCAGAGAATWATGAAAGTGGA | Amp oligo hybridizing region (SEQ ID NOs: 1-6 & 11 are contained within here) |
| 173 | GAATWATGAAAG | Amp oligo core sequence [truncated] (SEQ ID NOs: 1-6 & 11 share this) |
| 174 | gaaaatTGARAGTCAGAGAATWATGAAAGTGGARTTYAC | Amp oligo hybridizing region [extended] (SEQ ID NOs: 1-6 & 11 are contained within here) |
| 175 | GGAAAATTAATC | Amp oligo core sequence (SEQ ID NOs: 29-38 & 45 share this) |
| 176 | GGCATAGCTGCAGGAAAATTAATCATGGTTTTNTCAATGTG | Amp oligo hybridizing region (SEQ ID NOs: 29-38 & 45 are contained within here) [N Is preferably adenine or Inosine] |
| 177 | GAAAAAGGCATAGCTGCAGGAAAATTAATCATGGTTTTNTCAATGTGATGATG | Amp oligo hybridizing region [extended] (SEQ ID NOs: 29-38 & 45 are contained within here) [N Is preferably adenine or Inosine] |
| 178 | TCAGTGTTCAATGAATGTGGTCTCCAAAACGCTTTTTAGA | Detection probe hybridizing region (SEQ ID NOs 58-74 are contained within here) |
| 179 | ccaccccat | Amp oligo core sequence (SEQ ID NOs: 78-81 share this) |
| 180 | catggacag | Amp oligo core sequence (SEQ ID NOs: 82-84 share this) |
| 181 | catcattttcaRagtcatggacagttatctgaccacccccatgccttatcatccagtagcagtca | Amp oligo hybridizing region (SEQ ID NOs: 75-84 are contained within here) |
| 182 | TCTGACCACCCCCATGCCTTATCAtccagtagcagtca | Amp oligo hybridizing region (SEQ ID NOs: 75-80 are contained within here) |

TABLE 3-continued

Exemplary Oligomers, Reference Sequences and Regions

| SEQ ID NO: | Sequence | Description |
|---|---|---|
| 183 | CCACCCCCATGCCTTATCA | Amp oligo core sequence (SEQ ID NOs: 78-80 share this) |
| 184 | catcattttcaRagtcatggacagttatctgaccacccccat | Amp oligo hybridizing region (SEQ ID NOs: 81-84 are contained within here) |
| 185 | catcattttcaRagtcatggacagttatctgaccacc | Amp oligo hybridizing region (SEQ ID NOs: 82-84 are contained within here) |
| 186 | GCTAACTTGCCCAGGCTTGTG | Amp oligo core sequence (SEQ ID NOs: 108-113 share this) |
| 187 | GTTGTACGCTAACTTGCCCAGGCTTGTGT | Amp oligo hybridizing region (SEQ ID NOs: 108-113 are contained within here) |
| 188 | CTTGCCCAGGC | Amp oligo core sequence [truncated] (SEQ ID NOs: 108-113 share this) |
| 189 | GGGTAGTTGTACGCTAACTTGCCCAGGCTTGTGTAAGTC | Amp oligo hybridizing region [extended] (SEQ ID NOs: 108-113 are contained within here) |
| 190 | ACCTAAAGTCATG | Amp oligo core sequence (SEQ ID NOs: 118-121 share this) |
| 191 | GGCTATACCTAAAGTCATGAATCCTTGCAG | Amp oligo hybridizing region (SEQ ID NOs: 118-121 are contained within here) |
| 192 | CTAAAGTC | Amp oligo core sequence [truncated] (SEQ ID NOs: 118-121 share this) |
| 193 | CAGTTGGCTATACCTAAAGTCATGAATCCTTGCAGCACTG | Amp oligo hybridizing region [extended] (SEQ ID NOs: 118-121 are contained within here) |
| 194 | MRTRCAGAACYTAGAGGAGAAATGCAGTATTATCTAGTGAAGACTTAC | Detection probe hybridizing region (SEQ ID NOs 137-169 are contained within here) |
| 195 | MRTRCAGAACYTAGAGGAGAAATG | Detection probe hybridizing region (SEQ ID NOs 137-168 are contained within here) |
| 196 | AATTTAATACGACTCACTATAGGGAGA | T7 promoter sequence |
| 197 | CTTATCACACAAGCCTGGGCAAGTTAGCT | Tuner oligo |
| 198 | GenBank Accession number AB020564.1 and GI: 4001732 | HAV Reference Sequence |

TABLE 3-continued

Exemplary Oligomers, Reference Sequences and Regions

| SEQ ID NO: | Sequence | Description |
|---|---|---|
| 199 | GenBank Accession number AF162273.1 and GI: 5670171 | Parvo Reference Sequence |
| 200 | AAATATTAAAAGATCATTATAATATTTCTTTAGATAAT CCCCTAGAAAACCCATCCTCTCTGTTTGACTTAGTTGC TCGTATTAAAAATAACCTTAAAAACTCTCCAGACTTAT ATAGTCATCATTTTCAAAGTCATGGACAGTTATCTGAC CACCCCCATGCCTTATCATCCAGTAGCAGTCATGCAGA ACCTAGAGGAGAAGATGCAGTATTATCTAGTGAAGACT TACACAAGCCTGGGCAAGTTAGCGTACAACTACCCGGT ACTAACTATGTTGGGCCTGGCAATGAGCTACAAGCTGG GCCCCCGCAAAGTGCTGTTGACAGTGCTGCAAGGATTC ATGACTTTAGGTATAGCCAACTGGCTAAGTTGGGAATA AATCCATATACTCATTGGACTGTAGCAGATGAAGAGCT TTTAAAAAATATAAAAAATGAAACCGGGTTTCAAGCAC AAGTAGTAAAAGACTA | Type 1 synthetic construct. |
| 201 | AATATTAAAAGATCATTACAATATTTCTTTAGATAATC CCCTAGAAAACCCATCTTCCCTGTTTGACTTAGTTGCT CGTATTAAAAGTAATCTTAAAGACTCTCCAGACCTATA TAGTCATCATTTTCAAAGTCATGGACAGTTATCTGACC ACCCCCATGCCTTATCACCCAGTAGCAGTCATACAGAA CCTAGAGGAGAAAATGCAGTATTATCTAGTGAAGACTT ACACAAGCCTGGGCAAGTTAGCATACAACTACCCGGTA CTAACTATGTTGGGCCTGGCAATGAGCTACAAGCTGGG CCCCCGCAAAGTGCTGTGGACAGTGCTGCAAGGATTCA TGACTTTAGGTATAGCCAATTGGCTAAGCTGGGAATAA ACCCATATACTTATTGGACTGTAGCAGATGAGGAACTG TTAAAAAATATAAAAAATGAAACTGGGTTTCAAGCACA AGCAGTAAAAGATTA | Type 2 synthetic construct. |
| 202 | AAATTTTAAAAGATCATTACAACATTTCTTTAGACAAT CCTTTAGAAAACCCCTCTTCTTTATTTGACTTAGTTGC TCGCATTAAAAGCAATCTTAAAAACTCTCCAGACCTAT ATAGTCATCATTTTCAGAGCCATGGACAGTTATCTGAC CACCCCCATTCCTTATCACCCAGTAACAGTAGTACAGA ACCTAGAGGAGAAAATGCAGTATTATCTAGTGAAGACT TACACAAGCCTGGGCAAGTTAGCATACAATTACCCGGT ACTAACTATGTTGGGCCTGGCAATGAGCTACAAGCTGG GCCTCCGCAGAATGCTGTGGACAGTGCTGCAAGGATTC ATGACTTTAGGTATAGCCAATTGGCTAAGTTGGGAATA AATCCTTATACTCATTGGACGGTAGCAGATGAGGAATT GTTAAAAAATATAAAAAATGAAACAGGGTTTCAAGCAC AAGCAGTAAAAGACTA | Type 3 synthetic construct. |
| 203 | TTTGTCGGAAGCCCAGTTTCCTCCGAAGTTGTAGCTGC ATCGTGGGAAGAAGCCTTCTACACACCTTTGGCAGACC AGTTTCGTGAACTGTTAGTTGGGGTTGATTATGTGTGG GACGGTGTAAGGGGCTTACCTGTGTGTTGTGTGCAACA TATTAACAATAGTGGGGGAGGCTTGGGACTTTGTCCCC ATTGCATTAATGTAGGGGCTTGGTATAATGGATGGAAA TTTCGAGAATTTACTCCAGATTGGTGCGATGTAGCTGC CATGTGGGAGCTTCTAATCCCTTTTCTGTGCTAACCT GTAAAAAATGTGCTTACCTGTCTGGATTGCAAAGCTTT GTAGATTATGAGTAAAGAAAGTGGCAAATGGTGGGAAA GTAATGATAAATTTGCTAAAGCTGTGTATCAGCAATTT GTGGAATTTTATGAAAAAGTTACTGGAACAGACTTAGA GCTTATTCAAATATTAAAAGACCATTATAATATTTCTT TAGATAATCCCCTAGAAAACCCATCCTCTCTGTTTGAC TTAGTTGCTCGTATTAAAAATAACCTTAAAAACTCTCC AGACTTATATAGTCATCATTTTCAAAGTCATGGACAGT TATCTGACCACCCCCATGCCTTATCATCCAGTAGCAGT CATGCAGAACCTAGAGGAGAAAATGCAGTATTATCTAG TGAAGACTTACACAAGCCTGGGCAAGTTAGCGTACAAC TACCCGGTACTAACTATGTTGGGCCTGGCAATGAGCTA CAAGCTGGGCCCCCGCAAAGTGCTGTTGACAGTGCTGC AAGGATTCATGACTTTAGGTATAGCCAACTGGCTAAGT TGGGAATAAATCCATATACTCATTGGACTGTAGCAGAT GAAGAGCTTTTAAAAAATATAAAAAATGAAACTGGGTT TCAAGCACAAGTAGTAAAAGACTACTTTACTTTAAAAG | Parvovirus standard ARC-NTRLSSO WBN-035K99437 |

TABLE 3-continued

Exemplary Oligomers, Reference Sequences and Regions

| SEQ ID NO: | Sequence | Description |
|---|---|---|
| | GTGCAGCTGCCCCTGTGGCCCATTTTCAAGGAAGTTTG CCGGAAGTTCCCGCTTACAACGCCTCAGAAAAATACCC AAGCATgACTTCA | |

The present invention has been described in the context of particular examples and preferred embodiments. Those skilled in the art will appreciate that other embodiments are encompassed within the invention defined by the claims that follow.

What is claimed is:

1. An oligomer combination for detecting a hepatitis A virus (HAV) target nucleic acid in a sample, said oligomer combination comprising:

first and second amplification oligomers for amplifying an HAV nucleic acid target region, wherein (a) the first HAV amplification oligomer consists of a first target hybridizing sequence consisting of SEQ ID NO:2; and (b) the second HAV amplification oligomer is a promoter primer or promoter provider consisting of (i) a second target-hybridizing sequence consisting of SEQ ID NO:35 and (ii) a promoter sequence located 5 to the second target-hybridizing sequence.

2. The oligomer combination of claim 1, wherein the first HAV amplification oligomer and the second HAV amplification oligomer are contained in a kit.

3. A reaction mixture comprising an oligomer combination for detecting hepatitis A virus (HAV) target nucleic acid in a sample, wherein the oligomer combination comprises first and second amplification for amplifying an HAV nucleic acid target region, wherein
   (a) the first HAV amplification oligomer consists of a first target-hybridizing sequence consisting of SEQ ID NO:2; and
   (b) the second HAV amplification oligomer is a promoter primer or promoter provider consisting of (i) a second target-hybridizing sequence consisting of SEQ ID NO:35 and (ii) a promoter sequence located 5 to the second target-hybridizing sequence.

4. A method for detecting a hepatitis A virus (HAV) target nucleic acid in a sample, said method comprising:
   (A) providing a sample suspected of containing HAV;
   (B) contacting said sample with an oligomer combination for amplifying an HAV nucleic acid target region, said oligomer combination comprising:
   (I) a first HAV amplification oligomer consists of a first target hybridizing sequence consisting of SEQ ID NO:2; and
   (II) a second HAV amplification oligomer that is a promoter primer or promoter provider consisting of (i) a second target-hybridizing sequence consisting of SEQ ID NO:35 and (ii) a promoter sequence located 5' to the second target-hybridizing sequence;
   (C) performing an in vitro nucleic acid amplification reaction, wherein any HAV target nucleic acid present in said sample is used as a template for generating a HAV amplification product, wherein the amplification reaction is an isothermal amplification reaction; and
   (D) detecting the presence or absence of the HAV amplification product, wherein said detecting comprises contacting said in vitro nucleic acid amplification reaction with an HAV-specific detection probe oligomer configured to specifically hybridize to the HAV amplification product under conditions whereby the presence or absence of the HAV amplification product is determined, thereby indicating the presence or absence of HAV in said sample.

5. The method of claim 4, wherein the promoter sequence is a T7 promoter sequence.

6. The method of claim 5, wherein the T7 promoter sequence has the sequence shown in SEQ ID NO:196.

7. The method of claim 6, wherein the second HAV amplification oligomer has the sequence of SEQ ID NO: 18.

8. The method of claim 4, wherein step (B) further comprises contacting the sample with
   third and fourth amplification oligomers for amplifying the HAV nucleic acid target region, wherein (III) the third HAV amplification oligomer comprises a third target-hybridizing sequence that is from about 14 to about 27 contiguous nucleotides contained in the sequence of SEQ ID NO: 174 and that includes at least the sequence of SEQ ID NO: 173; and
   (IV) the fourth HAV amplification oligomer comprises a fourth target-hybridizing sequence that is from about 14 to about 30 contiguous nucleotides contained in the sequence of SEQ ID NO: 177 and that includes at least the sequence of SEQ ID NO:175;

wherein the third target-hybridizing sequence of is different from the first HAV target hybridizing sequence; and wherein the fourth target-hybridizing sequence is different from the second HAV target hybridizing sequence.

9. The method of claim 4, further comprising purifying the HAV target nucleic acid from other components in the sample before step (B).

10. The method of claim 9, wherein the purifying step comprises contacting the sample with at least one HAV-specific capture probe oligomer comprising a target-hybridizing sequence covalently attached to a sequence or moiety that binds to an immobilized probe,
   wherein said target-hybridizing sequence is selected from the group consisting of SEQ ID NOs:52-57, or
   wherein the HAV-specific capture probe oligomer has a sequence selected from the group consisting of SEQ ID NOs:46-51.

11. The method of claim 4, wherein the HAV-specific detection probe oligomer comprises a target-hybridizing sequence that is from about 14 to about 40 nucleotides in length and is configured to specifically hybridize to a target sequence contained within SEQ ID NO:198 from about nucleotide position 5965 to about nucleotide position 6028, or the HAV-specific detection probe target-hybridizing sequence is contained in the sequence of SEQ ID NO: 178, or the HAV-specific detection probe target-hybridizing sequence is selected from the group consisting of SEQ ID NOs:58-74.

12. The method of claim 4, wherein the HAV-specific detection probe comprises a label selected from the group consisting of
   (a) a chemiluminescent label;
   (b) a fluorescent label;
   (c) a quencher; and
   (d) a combination of two or more of (a), (b), and (c).

13. The method of claim 4, wherein the detecting step (D) occurs during the amplifying step (C).

14. The method of claim 13, wherein the HAV-specific detection probe comprises a fluorescent label, a quencher, or both.

15. The method of claim 11, wherein the HAV-specific detection probe is a TaqMan detection probe or a molecular beacon or a molecular torch, or wherein the HAV-specific detection probe further comprises a non-target-hybridizing sequence, and/or wherein the HAV-specific detection probe is a hairpin detection probe.

16. The method of claim 4, wherein the isothermal amplification reaction is a real-time isothermal amplification reaction.

17. The method of claim 4, wherein the sample is from an individual patient.

18. The method of claim 4, wherein the sample is pooled.

19. The method of claim 18, wherein the pooled sample is a pooled plasma sample.

20. The oligomer combination of claim 1, further comprising an HAV-specific detection probe oligomer, wherein the HAV-specific detection probe oligomer comprises a target-hybridizing sequence that is from about 14 to about 40 nucleotides in length and is configured to specifically hybridize to a target sequence contained within SEQ ID NO:198 from about nucleotide position 5965 to about nucleotide position 6028, or the HAV-specific detection probe target-hybridizing sequence is contained in the sequence of SEQ ID NO: 178, or the HAV-specific detection probe target-hybridizing sequence is selected from the group consisting of SEQ ID NOs:58-74.

21. The oligomer combination of claim 20, wherein the HAV-specific detection probe is a TaqMan detection probe or a molecular beacon or a molecular torch, or wherein the HAV-specific detection probe further comprises a non-target-hybridizing sequence, and/or wherein the HAV-specific detection probe is a hairpin detection probe.

22. The reaction mixture of claim 3, further comprising an HAV-specific detection probe oligomer, wherein the HAV-specific detection probe oligomer comprises a target-hybridizing sequence that is from about 14 to about 40 nucleotides in length and is configured to specifically hybridize to a target sequence contained within SEQ ID NO: 198 from about nucleotide position 5965 to about nucleotide position 6028, or the HAV-specific detection probe target-hybridizing sequence is contained in the sequence of SEQ ID NO: 178, or the HAV-specific detection probe target-hybridizing sequence is selected from the group consisting of SEQ ID NOs:58-74.

23. The reaction mixture of claim 22, wherein the HAV-specific detection probe is a TaqMan detection probe or a molecular beacon or a molecular torch, or wherein the HAV-specific detection probe further comprises a non-target-hybridizing sequence, and/or wherein the HAV-specific detection probe is a hairpin detection probe.

* * * * *

SEQUENCE LISTING

<160> NUMBER OF SEQ ID NOS: 203

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 1
cagagaatta tgaaagtgga                                               20

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 2
agtcagagaa ttatgaaagt gga                                           23

<210> SEQ ID NO 3
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 3
ugagagtcag agaattatga aagtgga                                       27

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 4
agtcagagaa ttatgaaagt gg                                            22

<210> SEQ ID NO 5
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 5
cagagaatta tgaaagtgg                                              19

<210> SEQ ID NO 6
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 6
tgagagtcag agaattatga aagtgg                                      26

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 7
tcagtgttca atgaatgt                                               18

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 8
tttactcagt gttcaatgaa tgt                                         23

<210> SEQ ID NO 9
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 9
ggagtttact cagtgttcaa tgaatgt                                     27

<210> SEQ ID NO 10
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 10
atgaaagtgg agtttactca gtgttcaatg aatgt                            35

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 11
gaaagtcaga gaataatgaa agt                                         23

<210> SEQ ID NO 12
<211> LENGTH: 56

```
<212> TYPE: DNA
<213> ORGANISM: Artificial Sequence
<220> FEATURE:
<223> OTHER INFORMATION: Synthetic Oligomer

<400> SEQUENCE: 12
aatttaatac gactcactat agggagagga aaattaatca tggtttatc aatgtg          56

<210> SEQ ID NO 13
<211> LENGTH: 56
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (48)..(48)
<223> OTHER INFORMATION: N is inosine

<400> SEQUENCE: 13
aatttaatac gactcactat agggagagga aaattaatca tggttttntc aatgtg         56

<210> SEQ ID NO 14
<211> LENGTH: 45
<212> TYPE: DNA
<213> ORGANISM: Artificial Sequence
<220> FEATURE:
<223> OTHER INFORMATION: Synthetic Oligomer

<400> SEQUENCE: 14
aatttaatac gactcactat agggagagca ggaaaattaa tcatg                     45

<210> SEQ ID NO 15
<211> LENGTH: 44
<212> TYPE: DNA
<213> ORGANISM: Artificial Sequence
<220> FEATURE:
<223> OTHER INFORMATION: Synthetic Oligomer

<400> SEQUENCE: 15
aatttaatac gactcactat agggagagca ggaaaattaa tcat                      44

<210> SEQ ID NO 16
<211> LENGTH: 43
<212> TYPE: DNA
<213> ORGANISM: Artificial Sequence
<220> FEATURE:
<223> OTHER INFORMATION: Synthetic Oligomer

<400> SEQUENCE: 16
aatttaatac gactcactat agggagagca ggaaaattaa tca                       43

<210> SEQ ID NO 17
<211> LENGTH: 42
<212> TYPE: DNA
<213> ORGANISM: Artificial Sequence
<220> FEATURE:
<223> OTHER INFORMATION: Synthetic Oligomer

<400> SEQUENCE: 17
aatttaatac gactcactat agggagagca ggaaaattaa tc                        42

<210> SEQ ID NO 18
<211> LENGTH: 54
<212> TYPE: DNA
<213> ORGANISM: Artificial Sequence
<220> FEATURE:
```

<223> OTHER INFORMATION: Synthetic Oligomer

<400> SEQUENCE: 18
aatttaatac gactcactat agggagaggc atagctgcag gaaaattaat catg　　　　54

<210> SEQ ID NO 19
<211> LENGTH: 53
<212> TYPE: DNA
<213> ORGANISM: Artificial Sequence
<220> FEATURE:
<223> OTHER INFORMATION: Synthetic Oligomer

<400> SEQUENCE: 19
aatttaatac gactcactat agggagaggc atagctgcag gaaaattaat cat　　　　53

<210> SEQ ID NO 20
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 20
aatttaatac gactcactat agggagaggc atagctgcag gaaaattaat ca　　　　52

<210> SEQ ID NO 21
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 21
aatttaatac gactcactat agggagaggc atagctgcag gaaaattaat c　　　　51

<210> SEQ ID NO 22
<211> LENGTH: 54
<212> TYPE: DNA
<213> ORGANISM: Artificial Sequence
<220> FEATURE:
<223> OTHER INFORMATION: Synthetic Oligomer

<400> SEQUENCE: 22
aatttaatac gactcactat agggagaact ctttctaaaa agcgttttgg agac　　　　54

<210> SEQ ID NO 23
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 23
aatttaatac gactcactat agggagatct ttctaaaaag cgttttggag ac　　　　52

<210> SEQ ID NO 24
<211> LENGTH: 54
<212> TYPE: DNA
<213> ORGANISM: Artificial Sequence
<220> FEATURE:
<223> OTHER INFORMATION: Synthetic Oligomer

<400> SEQUENCE: 24
aatttaatac gactcactat agggagaact ctttctaaag agcgttttgg agac　　　　54

```
<210> SEQ ID NO 25
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 25
aatttaatac gactcactat agggagatct ttctaaagag cgttttggag ac          52

<210> SEQ ID NO 26
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 26
aatttaatac gactcactat agggagaact ctttctaaaa agcgttttgg ag          52

<210> SEQ ID NO 27
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 27
aatttaatac gactcactat agggagaact ctttctaaag agcgttttgg ag          52

<210> SEQ ID NO 28
<211> LENGTH: 55
<212> TYPE: DNA
<213> ORGANISM: Artificial Sequence
<220> FEATURE:
<223> OTHER INFORMATION: Synthetic Oligomer

<400> SEQUENCE: 28
aatttaatac gactcactat agggagagga aaattaatca tggttttatc aatgt       55

<210> SEQ ID NO 29
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 29
ggaaaattaa tcatggtttt atcaatgtg                                    29

<210> SEQ ID NO 30
<211> LENGTH: 29
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (21)..(21)
<223> OTHER INFORMATION: N is inosine

<400> SEQUENCE: 30
ggaaaattaa tcatggtttt ntcaatgtg                                    29

<210> SEQ ID NO 31
<211> LENGTH: 18
<212> TYPE: DNA
```

```
<213> ORGANISM: Artificial Sequence
<220> FEATURE:
<223> OTHER INFORMATION: Synthetic Oligomer

<400> SEQUENCE: 31
gcaggaaaat taatcatg                                              18

<210> SEQ ID NO 32
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 32
gcaggaaaat taatcat                                               17

<210> SEQ ID NO 33
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 33
gcaggaaaat taatca                                                16

<210> SEQ ID NO 34
<211> LENGTH: 15
<212> TYPE: DNA
<213> ORGANISM: Artificial Sequence
<220> FEATURE:
<223> OTHER INFORMATION: Synthetic Oligomer

<400> SEQUENCE: 34
gcaggaaaat taatc                                                 15

<210> SEQ ID NO 35
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 35
ggcatagctg caggaaaatt aatcatg                                    27

<210> SEQ ID NO 36
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 36
ggcatagctg caggaaaatt aatcat                                     26

<210> SEQ ID NO 37
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 37
ggcatagctg caggaaaatt aatca                                      25
```

<210> SEQ ID NO 38
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 38
ggcatagctg caggaaaatt aatc                                          24

<210> SEQ ID NO 39
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 39
actctttcta aaaagcgttt tggagac                                       27

<210> SEQ ID NO 40
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 40
tctttctaaa aagcgttttg gagac                                         25

<210> SEQ ID NO 41
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 41
actctttcta aagagcgttt tggagac                                       27

<210> SEQ ID NO 42
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 42
tctttctaaa gagcgttttg gagac                                         25

<210> SEQ ID NO 43
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 43
actctttcta aaagcgttt tggag                                          25

<210> SEQ ID NO 44
<211> LENGTH: 25
<212> TYPE: DNA
<213> ORGANISM: Artificial Sequence
<220> FEATURE:

<210> SEQ ID NO 44
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 44
actctttcta aagagcgttt tggag                                    25

<210> SEQ ID NO 45
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 45
ggaaaattaa tcatggtttt atcaatgt                                 28

<210> SEQ ID NO 46
<211> LENGTH: 59
<212> TYPE: DNA
<213> ORGANISM: Artificial Sequence
<220> FEATURE:
<223> OTHER INFORMATION: Synthetic Oligomer

<400> SEQUENCE: 46
ggucccucug aaauuaacau uggguguucca aaaaaaaaa aaaaaaaaaa aaaaaaaa    59

<210> SEQ ID NO 47
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 47
guuccaucau ucuuuuuaug aacatttaaa aaaaaaaaa aaaaaaaaaa aaaaaaa     57

<210> SEQ ID NO 48
<211> LENGTH: 62
<212> TYPE: DNA
<213> ORGANISM: Artificial Sequence
<220> FEATURE:
<223> OTHER INFORMATION: Synthetic Oligomer

<400> SEQUENCE: 48
ccuucgccuu uuccucucca ugccugauct ttaaaaaaaa aaaaaaaaaa aaaaaaaaaa    60
aa                                                             62

<210> SEQ ID NO 49
<211> LENGTH: 59
<212> TYPE: DNA
<213> ORGANISM: Artificial Sequence
<220> FEATURE:
<223> OTHER INFORMATION: Synthetic Oligomer

<400> SEQUENCE: 49
ucgccuuuuc cucuccaugc cugaucttta aaaaaaaaa aaaaaaaaaa aaaaaaaa    59

<210> SEQ ID NO 50
<211> LENGTH: 59
<212> TYPE: DNA
<213> ORGANISM: Artificial Sequence
<220> FEATURE:
<223> OTHER INFORMATION: Synthetic Oligomer

<400> SEQUENCE: 50
ccuucgccuu uuccucucca ugccugttta aaaaaaaaa aaaaaaaaaa aaaaaaaa    59

<210> SEQ ID NO 51
<211> LENGTH: 57
<212> TYPE: DNA
<213> ORGANISM: Artificial Sequence
<220> FEATURE:
<223> OTHER INFORMATION: Synthetic Oligomer

<400> SEQUENCE: 51
ggccccacca cacauuccag gaagtttaaa aaaaaaaaaa aaaaaaaaaa aaaaaaa    57

<210> SEQ ID NO 52
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 52
ggucccucug aaauuaacau ugguguucc    29

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 53
guuccaucau ucuuuuuaug aaca    24

<210> SEQ ID NO 54
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 54
ccuucgccuu uuccucucca ugccugauc    29

<210> SEQ ID NO 55
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 55
ucgccuuuuc cucuccaugc cugauc    26

<210> SEQ ID NO 56
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 56
ccuucgccuu uuccucucca ugccug    26

<210> SEQ ID NO 57
<211> LENGTH: 24
<212> TYPE: DNA
<213> ORGANISM: Artificial Sequence
<220> FEATURE:

```
<223> OTHER INFORMATION: Synthetic Oligomer

<400> SEQUENCE: 57
ggccccacca cacauuccag gaag                                          24

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 58
ucaguguuca augaaugu                                                 18

<210> SEQ ID NO 59
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 59
ucaguguuca augaaugu                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 60
ucaguguuca augaaugu                                                 18

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 61
uguucaauga auguggucuc c                                             21

<210> SEQ ID NO 62
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 62
uguucaauga auguggucuc c                                             21

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 63
uguucaauga auguggucuc c                                             21
```

```
<210> SEQ ID NO 64
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 64
guucaaugaa ugggucucc aaaacgcu                                      28

<210> SEQ ID NO 65
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 65
guucaaugaa ugggucucc aaaacgcu                                      28

<210> SEQ ID NO 66
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 66
gaaugugguc uccaaaacgc u                                            21

<210> SEQ ID NO 67
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 67
gaaugugguc uccaaaacgc t                                            21

<210> SEQ ID NO 68
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 68
gaaugugguc uccaaaacgc t                                            21

<210> SEQ ID NO 69
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 69
guggucucca aaacgcuuuu uaga                                         24

<210> SEQ ID NO 70
<211> LENGTH: 24
<212> TYPE: DNA
<213> ORGANISM: Artificial Sequence
<220> FEATURE:
<223> OTHER INFORMATION: Synthetic Oligomer
```

```
<400> SEQUENCE: 70
guggucucca aaacgcuuuu uaga                                          24

<210> SEQ ID NO 71
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 71
guggucucca aaacgcuuuu uaga                                          24

<210> SEQ ID NO 72
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 72
guggucucca aaacgcuuuu uaga                                          24

<210> SEQ ID NO 73
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 73
guggucucca aaacgcuuuu uaga                                          24

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 74
gucuccaaaa cgcuuuuuag                                               20

<210> SEQ ID NO 75
<211> LENGTH: 13
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (7)..(7)
<223> OTHER INFORMATION: N is G or Inosine
<220> FEATURE:
<221> NAME/KEY: misc_feature
<222> LOCATION: (12)..(12)
<223> OTHER INFORMATION: N is G or Inosine

<400> SEQUENCE: 75
ccagtancag tna                                                      13

<210> SEQ ID NO 76
<211> LENGTH: 16
<212> TYPE: DNA
<213> ORGANISM: Artificial Sequence
<220> FEATURE:
<223> OTHER INFORMATION: Synthetic Oligomer
```

<400> SEQUENCE: 76
tcatccagta gcagtg                                                          16

<210> SEQ ID NO 77
<211> LENGTH: 14
<212> TYPE: DNA
<213> ORGANISM: Artificial Sequence
<220> FEATURE:
<223> OTHER INFORMATION: Synthetic Oligomer

<400> SEQUENCE: 77
tcacccagta acag                                                            14

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 78
tctgaccacc cccatgcctt atca                                                 24

<210> SEQ ID NO 79
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 79
ctgaccaccc ccatgcctta tca                                                  23

<210> SEQ ID NO 80
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 80
ccacccccat gccttatca                                                       19

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 81
ggacagttat ctgaccaccc ccat                                                 24

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 82
catggacagt tatctgacca cc                                                   22

<210> SEQ ID NO 83

<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 83
catcattttc aaagtcatgg acag         24

<210> SEQ ID NO 84
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 84
catcattttc agagtcatgg acag         24

<210> SEQ ID NO 85
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 85
ctctccagac ttatatagtc at           22

<210> SEQ ID NO 86
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 86
cctctctgtt tgacttagtt gctc         24

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 87
cctctttgtt tgacttagtt gctc         24

<210> SEQ ID NO 88
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 88
aatttaatac gactcactat agggagagct aacttgccca ggcttgtgt    49

<210> SEQ ID NO 89
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 89

```
aatttaatac gactcactat agggagaacg ctaacttgcc caggcttgtg t        51
```

<210> SEQ ID NO 90
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 90

```
aatttaatac gactcactat agggagagtt gtacgctaac ttgcccaggc ttgtgt    56
```

<210> SEQ ID NO 91
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 91

```
aatttaatac gactcactat agggagagct aacttgccca ggcttgtg            48
```

<210> SEQ ID NO 92
<211> LENGTH: 50
<212> TYPE: DNA
<213> ORGANISM: Artificial Sequence
<220> FEATURE:
<223> OTHER INFORMATION: Synthetic Oligomer

<400> SEQUENCE: 92

```
aatttaatac gactcactat agggagaacg ctaacttgcc caggcttgtg          50
```

<210> SEQ ID NO 93
<211> LENGTH: 55
<212> TYPE: DNA
<213> ORGANISM: Artificial Sequence
<220> FEATURE:
<223> OTHER INFORMATION: Synthetic Oligomer

<400> SEQUENCE: 93

```
aatttaatac gactcactat agggagagtt gtacgctaac ttgcccaggc ttgtg     55
```

<210> SEQ ID NO 94
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 94

```
aatttaatac gactcactat agggagaaac atagttagta ccgggta              47
```

<210> SEQ ID NO 95
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 95

```
aatttaatac gactcactat agggagacaa catagttagt accgggta             48
```

<210> SEQ ID NO 96
<211> LENGTH: 49
<212> TYPE: DNA

```
<213> ORGANISM: Artificial Sequence
<220> FEATURE:
<223> OTHER INFORMATION: Synthetic Oligomer

<400> SEQUENCE: 96
aatttaatac gactcactat agggagacca acatagttag taccgggta          49

<210> SEQ ID NO 97
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 97
aatttaatac gactcactat agggagatgc gggggcccag cttgta             46

<210> SEQ ID NO 98
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 98
aatttaatac gactcactat agggagaggc tacctaaa gtcatg               46

<210> SEQ ID NO 99
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 99
aatttaatac gactcactat agggagaggc tacctaaa gtcatga              47

<210> SEQ ID NO 100
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 100
aatttaatac gactcactat agggagagct atacctaaag tcatga             46

<210> SEQ ID NO 101
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 101
aatttaatac gactcactat agggagaacc taaagtcatg aatccttgca g       51

<210> SEQ ID NO 102
<211> LENGTH: 50
<212> TYPE: DNA
<213> ORGANISM: Artificial Sequence
<220> FEATURE:
<223> OTHER INFORMATION: Synthetic Oligomer

<400> SEQUENCE: 102
aatttaatac gactcactat agggagacca acatagttag taccgggggt         50
```

<210> SEQ ID NO 103
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 103
aatttaatac gactcactat agggagacca acatagttag taccgggggg         49

<210> SEQ ID NO 104
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 104
aatttaatac gactcactat agggagacca acatagttag taccggggg          48

<210> SEQ ID NO 105
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 105
aatttaatac gactcactat agggagacca acatagttag taccggg            47

<210> SEQ ID NO 106
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 106
aatttaatac gactcactat agggagacca acatagttag taccgg             46

<210> SEQ ID NO 107
<211> LENGTH: 45
<212> TYPE: DNA
<213> ORGANISM: Artificial Sequence
<220> FEATURE:
<223> OTHER INFORMATION: Synthetic Oligomer

<400> SEQUENCE: 107
aatttaatac gactcactat agggagacca acatagttag taccg              45

<210> SEQ ID NO 108
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 108
gctaacttgc ccaggcttgt gt                                       22

<210> SEQ ID NO 109
<211> LENGTH: 24
<212> TYPE: DNA
<213> ORGANISM: Artificial Sequence
<220> FEATURE:

<223> OTHER INFORMATION: Synthetic Oligomer

<400> SEQUENCE: 109
acgctaactt gcccaggctt gtgt                                              24

<210> SEQ ID NO 110
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 110
gttgtacgct aacttgccca ggcttgtgt                                         29

<210> SEQ ID NO 111
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 111
gctaacttgc ccaggcttgt g                                                 21

<210> SEQ ID NO 112
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 112
acgctaactt gcccaggctt gtg                                               23

<210> SEQ ID NO 113
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 113
gttgtacgct aacttgccca ggcttgtg                                          28

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 114
aacatagtta gtaccgggta                                                   20

<210> SEQ ID NO 115
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 115
caacatagtt agtaccgggt a                                                 21

```
<210> SEQ ID NO 116
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 116
ccaacatagt tagtaccggg ta                                              22

<210> SEQ ID NO 117
<211> LENGTH: 10
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (7)..(7)
<223> OTHER INFORMATION: N is G or Inosine

<400> SEQUENCE: 117 ccagtancag                                                            10

<210> SEQ ID NO 118
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 118
ggctatacct aaagtcatg                                                  19

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 119
ggctatacct aaagtcatga                                                 20

<210> SEQ ID NO 120
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 120
gctataccta aagtcatga                                                  19

<210> SEQ ID NO 121
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 121
acctaaagtc atgaatcctt gcag                                            24

<210> SEQ ID NO 122
<211> LENGTH: 23
<212> TYPE: DNA
```

<213> ORGANISM: Artificial Sequence
<220> FEATURE:
<223> OTHER INFORMATION: Synthetic Oligomer

<400> SEQUENCE: 122
ccaacatagt tagtaccggg ggt                                            23

<210> SEQ ID NO 123
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 123
ccaacatagt tagtaccggg gg                                             22

<210> SEQ ID NO 124
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 124
ccaacatagt tagtaccggg g                                              21

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 125
ccaacatagt tagtaccggg                                                20

<210> SEQ ID NO 126
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 126
ccaacatagt tagtaccgg                                                 19

<210> SEQ ID NO 127
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 127
ccaacatagt tagtaccg                                                  18

<210> SEQ ID NO 128
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 128
atgcgagcaa ctaagtcaaa cagggagttt aaaaaaaaaa aaaaaaaaaa aaaaaaaaaa    60

<210> SEQ ID NO 129
<211> LENGTH: 52
<212> TYPE: DNA
<213> ORGANISM: Artificial Sequence
<220> FEATURE:
<223> OTHER INFORMATION: Synthetic Oligomer

<400> SEQUENCE: 129
tgcgggggcc cagcttgtat ttaaaaaaaa aaaaaaaaa aaaaaaaaaa aa            52

<210> SEQ ID NO 130
<211> LENGTH: 59
<212> TYPE: DNA
<213> ORGANISM: Artificial Sequence
<220> FEATURE:
<223> OTHER INFORMATION: Synthetic Oligomer

<400> SEQUENCE: 130
tggctatacc taaagtcatg aatcctttta aaaaaaaaa aaaaaaaaaa aaaaaaaa       59

<210> SEQ ID NO 131
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 131
agtactgaaa tccatatcgg ttgtttaaaa aaaaaaaaa aaaaaaaaaa aaaaaa         56

<210> SEQ ID NO 132
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 132
atgcgagcaa ctaagtcaaa cagggag                                        27

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 133
tgcgggggcc cagcttgta                                                 19

<210> SEQ ID NO 134
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 134
tggctatacc taaagtcatg aatcct                                         26

<210> SEQ ID NO 135
<211> LENGTH: 23
<212> TYPE: DNA
<213> ORGANISM: Artificial Sequence
<220> FEATURE:

```
<223> OTHER INFORMATION: Synthetic Oligomer

<400> SEQUENCE: 135
agtactgaaa tccatatcgg ttg                                           23

<210> SEQ ID NO 136
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 136
gagtatatgg gtttattccc a                                             21

<210> SEQ ID NO 137
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 137
uacagaaccu agaggagaaa aug                                           23

<210> SEQ ID NO 138
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 138
uacagaaccu agaggagaa                                                19

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 139
gaaccuagag gagaaaaug                                                19

<210> SEQ ID NO 140
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 140
cagaaccuag aggagaa                                                  17

<210> SEQ ID NO 141
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 141
cagaaccuag aggagaaaau g                                             21
```

```
<210> SEQ ID NO 142
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 142
cgugcagaac cuagaggaga a                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 143
cauacagaac cuagaggaga a                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 144
aguacagaac cuagaggaga a                                              21

<210> SEQ ID NO 145
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 145
uacagaaccu agaggagaa                                                 19

<210> SEQ ID NO 146
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 146
ugcagaaccu agaggagaa                                                 19

<210> SEQ ID NO 147
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 147
agugcagaac cuagaggaga a                                              21

<210> SEQ ID NO 148
<211> LENGTH: 17
<212> TYPE: DNA
<213> ORGANISM: Artificial Sequence
<220> FEATURE:
<223> OTHER INFORMATION: Synthetic Oligomer
```

```
<400> SEQUENCE: 148
cagaaccuag aggagaa                                              17

<210> SEQ ID NO 149
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 149
cagaaccuag aggagaa                                              17

<210> SEQ ID NO 150
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 150
cgugcagaac cuagaggaga a                                         21

<210> SEQ ID NO 151
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 151
cgugcagaac cuagaggaga a                                         21

<210> SEQ ID NO 152
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 152
cgugcagaac cuagaggaga a                                         21

<210> SEQ ID NO 153
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 153
cgugcagaac cuagaggaga a                                         21

<210> SEQ ID NO 154
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 154
cgugcagaac cuagaggaga a                                         21

<210> SEQ ID NO 155
<211> LENGTH: 21
```

```
<212> TYPE: DNA
<213> ORGANISM: Artificial Sequence
<220> FEATURE:
<223> OTHER INFORMATION: Synthetic Oligomer

<400> SEQUENCE: 155
cguacagaac cuagaggaga a                                              21

<210> SEQ ID NO 156
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 156
cgugcagaac cuagaggagg agau                                           24

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 157
gugcagaacc uagaggagaa                                                20

<210> SEQ ID NO 158
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 158
ugcagaaccu agaggagaa                                                 19

<210> SEQ ID NO 159
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 159
gaaccuagag gagaagaug                                                 19

<210> SEQ ID NO 160
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 160
caugcagaac cuagaggaga a                                              21

<210> SEQ ID NO 161
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 161
```

```
caugcagaac cuagaggaga a                                                21

<210> SEQ ID NO 162
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 162
gcagaaccua gaggagaaaa ug                                               22

<210> SEQ ID NO 163
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 163
gaaccuagag gagaaaaug                                                   19

<210> SEQ ID NO 164
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 164
gaacuuagag gagaaaaug                                                   19

<210> SEQ ID NO 165
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 165
cagaaccuag aggagaa                                                     17

<210> SEQ ID NO 166
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 166
cagaaccuag aggagaa                                                     17

<210> SEQ ID NO 167
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 167
cagaaccuag aggagaa                                                     17

<210> SEQ ID NO 168
<211> LENGTH: 19
<212> TYPE: DNA
<213> ORGANISM: Artificial Sequence
```

-continued

```
<220> FEATURE:
<223> OTHER INFORMATION: Synthetic Oligomer

<400> SEQUENCE: 168
gaaccuagag gagaaaaug                                              19

<210> SEQ ID NO 169
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 169
guauuaucua gugaagacuu ac                                          22

<210> SEQ ID NO 170
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 170
cagagaatwa tgaaagt                                                17

<210> SEQ ID NO 171
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 171
cagagaatwa tgaaagtgg                                              19

<210> SEQ ID NO 172
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 172
tgaragtcag agaatwatga aagtgga                                     27

<210> SEQ ID NO 173
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 173
gaatwatgaa ag                                                     12

<210> SEQ ID NO 174
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 174
gaaaattgar agtcagagaa twatgaaagt ggarttyac                        39
```

```
<210> SEQ ID NO 175
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 175
ggaaaattaa tc                                                          12

<210> SEQ ID NO 176
<211> LENGTH: 41
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (33)..(33)
<223> OTHER INFORMATION: N is A or Inosine

<400> SEQUENCE: 176
ggcatagctg caggaaaatt aatcatggtt ttntcaatgt g                          41

<210> SEQ ID NO 177
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (39)..(39)
<223> OTHER INFORMATION: N is A or Inosine

<400> SEQUENCE: 177
gaaaaaggca tagctgcagg aaaattaatc atggttttnt caatgtgatg atg            53

<210> SEQ ID NO 178
<211> LENGTH: 40
<212> TYPE: DNA
<213> ORGANISM: Artificial Sequence
<220> FEATURE:
<223> OTHER INFORMATION: Synthetic Oligomer

<400> SEQUENCE: 178
tcagtgttca atgaatgtgg tctccaaaac gcttttaga                             40

<210> SEQ ID NO 179
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 179 ccaccccccat                                                            10

<210> SEQ ID NO 180

<400> SEQUENCE: 180

000

<210> SEQ ID NO 181
<211> LENGTH: 65
<212> TYPE: DNA
```

<213> ORGANISM: Artificial Sequence
<220> FEATURE:
<223> OTHER INFORMATION: Synthetic Oligomer

<400> SEQUENCE: 181
catcattttc aragtcatgg acagttatct gaccaccccc atgccttatc atccagtagc        60
agtca        65

<210> SEQ ID NO 182
<211> LENGTH: 38
<212> TYPE: DNA
<213> ORGANISM: Artificial Sequence
<220> FEATURE:
<223> OTHER INFORMATION: Synthetic Oligomer

<400> SEQUENCE: 182
tctgaccacc cccatgcctt atcatccagt agcagtca        38

<210> SEQ ID NO 183
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 183 ccaccccat gccttatca        19

<210> SEQ ID NO 184
<211> LENGTH: 42
<212> TYPE: DNA
<213> ORGANISM: Artificial Sequence
<220> FEATURE:
<223> OTHER INFORMATION: Synthetic Oligomer

<400> SEQUENCE: 184
catcattttc aragtcatgg acagttatct gaccaccccc at        42

<210> SEQ ID NO 185
<211> LENGTH: 37
<212> TYPE: DNA
<213> ORGANISM: Artificial Sequence
<220> FEATURE:
<223> OTHER INFORMATION: Synthetic Oligomer

<400> SEQUENCE: 185
catcattttc aragtcatgg acagttatct gaccacc        37

<210> SEQ ID NO 186
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 186
gctaacttgc ccaggcttgt g        21

<210> SEQ ID NO 187
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 187
gttgtacgct aacttgccca ggcttgtgt                                        29

<210> SEQ ID NO 188
<211> LENGTH: 11
<212> TYPE: DNA
<213> ORGANISM: Artificial Sequence
<220> FEATURE:
<223> OTHER INFORMATION: Synthetic Oligomer

<400> SEQUENCE: 188
cttgcccagg c                                                           11

<210> SEQ ID NO 189
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 189
gggtagttgt acgctaactt gcccaggctt gtgtaagtc                             39

<210> SEQ ID NO 190
<211> LENGTH: 13
<212> TYPE: DNA
<213> ORGANISM: Artificial Sequence
<220> FEATURE:
<223> OTHER INFORMATION: Synthetic Oligomer

<400> SEQUENCE: 190
acctaaagtc atg                                                         13

<210> SEQ ID NO 191
<211> LENGTH: 30
<212> TYPE: DNA
<213> ORGANISM: Artificial Sequence
<220> FEATURE:
<223> OTHER INFORMATION: Synthetic Oligomer

<400> SEQUENCE: 191
ggctatacct aaagtcatga atccttgcag                                       30

<210> SEQ ID NO 192

<400> SEQUENCE: 192

000

<210> SEQ ID NO 193
<211> LENGTH: 40
<212> TYPE: DNA
<213> ORGANISM: Artificial Sequence
<220> FEATURE:
<223> OTHER INFORMATION: Synthetic Oligomer

<400> SEQUENCE: 193
cagttggcta tacctaaagt catgaatcct tgcagcactg                            40

<210> SEQ ID NO 194
<211> LENGTH: 49
<212> TYPE: DNA
<213> ORGANISM: Artificial Sequence
<220> FEATURE:
<223> OTHER INFORMATION: Synthetic Oligomer

<400> SEQUENCE: 194

```
mrtrcagaac ytagaggaga aratgcagta ttatctagtg aagacttac              49

<210> SEQ ID NO 195
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 195
mrtrcagaac ytagaggaga aratg                                        25

<210> SEQ ID NO 196
<211> LENGTH: 27
<212> TYPE: DNA
<213> ORGANISM: Artificial Sequence
<220> FEATURE:
<223> OTHER INFORMATION: Synthetic Oligomer

<400> SEQUENCE: 196
aatttaatac gactcactat agggaga                                      27

<210> SEQ ID NO 197
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 197
cttatcacac aagcctgggc aagttagct                                    29

<210> SEQ ID NO 198
<211> LENGTH: 7477
<212> TYPE: DNA
<213> ORGANISM: Hepatitis A virus
<300> PUBLICATION INFORMATION:
<308> DATABASE ACCESSION NUMBER: GenBank / AB020564.1  GI:4001732
<309> DATABASE ENTRY DATE: 2001-08-04
<313> RELEVANT RESIDUES IN SEQ ID NO: (1)..(7477)

<400> SEQUENCE: 198
ttcaagaggg gtctccggag ttttccggag cccctcttgg aagtccatgg tgaggggact     60
tgatacctca ccgccgtttg cctaggctat aggctaaatt tccctttccc tgtccttccc    120
ctattcccct ttgttttgtt tgtaaatatt aattcctgca ggttcagggt tctttaatct    180
gtttctctat aagaacactc aattttcacg ctttctgtct tctttcttcc agggctctcc    240
ccttgcccta ggctctggcc gttgcgcccg gcggggtcaa ctccatgatt agcatggagc    300
tgtaggagtc taaattgggg acgcagatgt ttgggacgtc accttgcagt gttaacttgg    360
ctttcatgaa cctctttgat ctttcacaag aggtaggcta cgggtgaaac ctcttaggct    420
aatacttcta tgaagagatg ccttggatag ggtaacagcg gcggatattg gtgagttgtt    480
aagacaaaaa ccattcaacg ccgaaggact ggttctcatc cagtggatgc attgagtgaa    540
ttgattgtca aggctgtctc taggtttaat cccagacctc tctgtgctta gggcaaacac    600
tatttggcct taaatgggat cctgtgagag ggggtccctc cattgacagc tggactgttc    660
tttggggcct tatgtggtgt ttgcctctga ggtactcagg ggcatttagg tttttcctca    720
ttcttaaaca ataatgaata tgtccaaaca aggaattttc cagactgttg ggagtggcct    780
tgaccacatc ctgtctctgg cagatattga ggaagaacaa atgattcagt ccgttgatag    840
```

```
gactgcagtg actggtgctt cttattttac ttctgtggac caatcgtcag ttcacactgc    900
tgaggttggc tcacatcaaa ttgaacctTT gaaaacctct gttgataaac ctggttctaa    960
gaagactcag ggggagaagt ttttcttgat tcactctgct gattggctta ctacacatgc   1020
tcttttTcat gaagttgcaa aattggatgt ggtgaaatta ctgtataatg agcaatttgc   1080
tgtccaaggc ttgttgagat atcacacata tgcaagattt ggcattgaga ttcaagttca   1140
gataaaccct acacccttTc agcaaggggg attaatttgt gccatggttc ctggtgacca   1200
aagttatggt tcaatagcat ccttgactgt ttatcctcat ggtctgttaa attgtaacat   1260
caacaatgtt gttagaataa aggttccatt catttatact agaggtgctt atcattttaa   1320
agatccacag tacccagttt gggaattaac aatcagagtt tggtcagagt tgaatattgg   1380
aacaggaact tcggcttaca cttcacttaa cgttttagct aggtttacag atttggagtt   1440
acatggttta actcctcttt ctacacagat gatgagaaat gaatttagag ttagtactac   1500
tgaaaatgtt gtaaacttgt caaattatga agatgcaagg gcaaaaatgt cttttgcttt   1560
ggatcaggaa gattggaagt ctgatccctc tcaaggtggt ggaattaaaa ttactcattt   1620
tactacttgg acatccattc caaccttagc tgcccagttt ccgtttaatg cttcagattc   1680
ggttgggcaa caaattaaag ttattccagt ggacccatat ttttTccaga tgacaaacac   1740
taatcctgac caaaaatgta taactgccct ggcttctatt tgtcagatgt tttgtttttg   1800 gagggggagat cttgtttttg attttcaggt ttTttccaact aaatatcatt caggtagatt   1860
attgttttgt tttgttcctg ggaatgagtt aatagatgtt actggaatta cattaaagca   1920
ggcaactact gctccttgtg cagtgatgga cattacagga gtgcaatcaa ctttgagatt   1980
tcgtgttcct tggatttctg atacacccta tcgagtaaat aggtacacga agtcggcaca   2040
tcaaaaaggt gagtacactg ccattggaaa gcttattgtg tactgttaca atagactgac   2100
ttctccttct aatgttgctt ctcatgttag agttaatgtt tatctttcag caattaatct   2160
ggaatgtttt gctcctcttt atcatgctat ggatgttacc acacaagttg agatgattc    2220 aggaggtttt tcaacaacag tttctactga gcagaatgtt cctgatcccc aagttggcat   2280
aacaaccatg agggacctaa aagggaaagc caatagagga aagatggatg tttcaggtgt   2340
gcaagcacct gtgggagcta tcacaacaat tgaggatcca gttttagcaa agaaagtgcc   2400
tgagacattt cctgaattga aacctggaga gtctagacat acatcagatc atatgtctat   2460
ttataaattt atgggaaggt ctcattttct gtgtacttTt acttttaatt caaataataa   2520
agagtacaca tttccaataa ctctgtcttc gacttctaat cctcctcatg gtttaccatc   2580
aacattaagg tggttcttca atctgtttca gttgtataga ggaccattgg atttgacaat   2640
tattatcaca ggagccactg atgtggatgg tatggcctgg ttcactccag taggccttgc   2700
tgtcgacacc ccttgggtgg aaaaggagtc agctttgtct attgattaca aaactgctct   2760
tggagctgtt agatttaata caagaagaac agggaatatt cagattagat tgccatggta   2820
ttcttattTg tatgccgtgt ctggagcact ggatggtctg ggggataaaa cagattccac   2880
atttggattg gtttccattc agattgcaaa ttacaatcat tctgatgaat atttgtcctt   2940
tagttgctat ttgtctgtta cagaacaatc agagttctat tttcctagag ctccattaaa   3000
ttcaaatgct atgttgtcca ctgagtccat gatgagcaga attgcagctg ggacttgga    3060 gtcatcggtg gatgatccta gatcagagga ggacagaaga tttgagagtc atatagaaag   3120
taggaaacca tacaaagaat tgagattgga ggttggcaaa caaagactca agtatgctca   3180
ggaagaactg tcaaatgagg tgcttccacc tcctaggaaa ataaagggggc tattttcaca   3240
```

```
agctaaaatt tctctttttt atactgagga gcatgaaata atgaaatttt cttggagagg    3300
agtaactgct gacactaggg ctttgagaag atttggattc tctatggctg ctggtagaag    3360
tgtgtggact cttgagatgg atgctggagt tcttactgga agattggtca gattgaatga    3420
tgagaaatgg acagaaatga aagatgataa aattgtttca ttaatcgaaa aattcacaag    3480
caacaaatat tggtctaaag tgaattttcc acatggaatg ttagatcttg aagaaattgc    3540
tgccaactct aaagattttc caaatatgtc tgagacagat ttgtgtttcc tgttgcattg    3600
gctgaatcca agaaaataa atttagcaga tagaatgctt ggattgtctg gagtgcagga    3660
aattaaagaa cagggtgttg gattgatagc agagtgtaga actttcttgg attctattgc    3720
tgggactctg aaatccatga tgtttggatt tcatcattct gtgactgttg aaattataaa    3780
tactgtgctt tgttttgtta agagtggaat tctactctat gtcatacaac aattgaacca    3840
agatgagcac tcccacataa ttggtttgtt gagagtcatg aattatgcag atattggctg    3900
ctcagttatt tcatgtggca agttttttc taaaatgtta gaaacagttt ttaattggca    3960
aatggactcc agaatgatgg agctgagaac tcagagcttt tccaattggc taagagacat    4020
ttgttcagga attactattt ttaaaagttt taaggatgcc atatattggt tatatacaaa    4080
attgaaggat ttttatgaag taaattatgg caagaagaag gatgttctta atattcttaa    4140
agataaccag caaaaatag aaaaagctat tgaagaagca gacaattttt gcattttgca    4200
aattcaagat gtagaaaaat ttgatcagta tcagaaaggg gttgatttaa tacaaaagct    4260
gagaactgtt cattcaatgg ctcaagttga ccctagcctt gggttcatt tgtcacctct    4320 tagagattgt atagccagag tccaccaaaa gctcaagaat cttggatcta taaatcaggc    4380
catggtgaca agtagtgagc cagttgtttg ctatttatat ggcaaaagag gaggagggaa    4440
aagcttgact tcaattgcat tggcaaccaa gatttgtaaa cactatggtg ttgaacctga    4500
gaaaaatatt tacactaaac ctgtggcttc agactattgg gatggttata gtggacaatt    4560
ggtttgcatt attgatgata ttggccaaaa tacaacagat gaagattggt cagatttttg    4620
tcaattagtg tcaggatgcc caatgagatt gaatatggct tctcttgagg agaagggcag    4680
acatttttcc tctccttta taatagcaac ttcaaattgg tcaaatccaa gtccaaaaac    4740
agtttatgtt aaggaagcaa ttgatcgtag gcttcatttt aaggttgaag ttaaacctgc    4800 ttcattttt aaaaatcctc ataatgatat gttaaatgtt aatttggcta aaacaaatga    4860
tgcaattaag gacatgtctt gtgttgatct agtaatggat ggacataaca tttcattgat    4920
ggatttactt agttctttag tgatgacagt tgaaattagg aagcaaaaata tgagtgaatt    4980 catggagttg tggtcccagg gaatctcaga tgatgacaat gatagtgcag tagctgagtt    5040
tttccaatct tttccatctg gtgaaccatc aaattccaaa ttatctagtt ttttccaatc    5100
tgtcactaat cacaagtggg ttgctgtggg agctgcagtt ggcattcttg gagtgcttgt    5160
gggaggatgg ttcgtgtaca agcatttctc ccgcaaagag gaagaaccaa ttccagctga    5220
agggggttat catggcgtga ctaagcccaa acaggtgatt aaattggatg cagatccagt    5280
agagtctcag tcaactttag aaatagcagg attagttagg aaaaatttgg ttcagtttgg    5340
agttggggag aaaaatggat gtgtgagatg ggttatgaat gccttgggag tgaaggatga    5400
ttggttatta gtaccttctc atgcttacaa atttgaaaag gattatgaaa tgatggagtt    5460
ttatttcaat agaggtggaa cttactattc aatttcagct ggaaatgttg ttattcaatc    5520
tttagatgtg gggtttcaag atgttgttct aatgaaggtt cctacaattc ccaagtttag    5580
```

```
agatattact caacatttta ttaagaaagg agatgtacct agagccttga atcgcttggc    5640
aacattagtg acaactgtta atggaactcc tatgttaatt tctgagggac cattaaagat    5700
ggaggaaaaa gccacttatg ttcataagaa gaatgatggt accacagttg atttgactgt    5760
tgatcaggca tggagaggaa aaggtgaagg tcttcctgga atgtgtggtg gggctctggt    5820
gtcatcaaat cagtccatac agaatgcaat tttgggtatt catgttgctg aggaaattc    5880 aattcttgtg gcaaagttgg ttactcaaga aatgttccaa atattgata gaaaattga    5940 aagtcagaga ataatgaaag tggaattcac tcagtgttca atgaatgtag tctccaaaac    6000 gcttttttaga aagagtccca ttcatcatca cattgataaa accatgatta atttctgc    6060 agctatgcct tttctaaag ttgaaattga tccaatggct gtgatgttgt ctaaatattc    6120
attacctctt gtagaagaac cagaggatta caaagaagct tcagtttttt atcaaaacaa    6180
gatagtaggc aagactcagt tagttgatga ctttttagat cttgatatgg ccattacagg    6240
ggctccaggc attgatgcta ttaatatgga ttcatctcct gggtttcctt atgttcaaga    6300
aaaattgact aaaagagatt taatttggtt ggatgaaaat ggtttgctgc taggagttca    6360
tccaagattg gctcagagaa ttttatttaa cactgtcatg atggaaaatt gttctgacct    6420
agatgttgtt tttacaactt gtccaaaaga tgaattgaga cctttagaga aagttttgga    6480
atcaaaaaca agagcaattg atgcttgtcc tttggattat acaattttat gtcgaatgta    6540
ctggggtcca gctattagtt atttttcattt gaatccaggg tttcacacag tgttgctat    6600 tggcatagat cctgatagac agtgggatga attatttaaa ccaatgataa gatttggaga    6660
tgttggtctt gatttagatt ttctgcctt tgatgctagt cttagtccat ttatgatcag    6720
ggaggcgggt agaatcatga gtgaattatc tggaacacca tctcatttg aacggctct    6780 tatcaatact atcattttatt ctaaacattt gctgtacaat tgttgttatc atgtctgtgg    6840
ttcaatgcct tctgggtccc cttgtacagc tttgttgaat tcaattatta caacattaa    6900 tttgtattat gtgtttttcta aaatatttgg aaagtctcca gttttcttt gtcaagctct    6960 gaggatcctt tgttatggag atgatgtttt gatagttttt tccagagatg ttcaaattga    7020
taatcttgat ttgattggac agaaaattgt ggatgaattc aaaaaacttg gcatgacagc    7080
cacttcagct gataaaaatg tgcctcaact gaagccagtt tcagaattga ccttcttaa    7140 aagatctttt aatttggtgg aggacagaat taggcctgca atttcagaaa agacaatttg    7200
gtctttgata gcttggcaga gaagcaacgc tgagtttgag cagaatttag aaaatgctca    7260
gtggtttgct tttatgcatg gctatgagtt ttatcagaaa ttttattatt tgttcagtc    7320 ctgtttggag aaagagatga tagaatatag gcttaaatct tatgattggt ggagaatgag    7380
attttatgac cagtgtttca tttgtgacct ttcatgattt gtttaaacaa attttcttaa    7440
aatttctgag gtttgtttat ttcttttatc agtaaat                            7477
```

<210> SEQ ID NO 199
<211> LENGTH: 5594
<212> TYPE: DNA
<213> ORGANISM: Erythrovirus B19
<300> PUBLICATION INFORMATION:
<308> DATABASE ACCESSION NUMBER: GenBank / AF162273.1 GI:5670171
<309> DATABASE ENTRY DATE: 1999-08-02
<313> RELEVANT RESIDUES IN SEQ ID NO: (1)..(5594)

<400> SEQUENCE: 199

```
ccaaatcaga tgccgccggt cgccgccggt aggcgggact tccggtacaa gatggcggac     60
aattacgtca tttcctgtga cgtcatttcc tgtgacgtca cttccggtgg gcgggacttc    120
```

```
cggaattagg gttggctctg ggccagcttg cttggggttg ccttgacact aagacaagcg    180
gcgcgccgct tgtcttagtg gcacgtcaac cccaagcgct ggcccagagc caaccctaat    240
tccggaagtc ccgcccaccg gaagtgacgt cacaggaaat gacgtcacag gaaatgacgt    300
aattgtccgc catcttgtac cggaagtccc gcctaccggc ggcgaccggc ggcatctgat    360
ttggtgtctt cttttaaatt ttagcgggct ttttccccgc cttatgcaaa tgggcagcca    420
ttttaagtgt ttcactataa ttttattggt cagttttgta acggttaaaa tgggcggagc    480
gtaggcgggg actacagtat atatagcacg gcactgccgc agctctttct ttctgggctg    540 cttttttcctg gactttcttg ctgtttttg tgagctaact aacaggtatt tatactactt    600
gttaacatac taacatggag ctatttagag gggtgcttca agtttcttct aatgttctgg    660
actgtgctaa cgataactgg tggtgctctt tactggatttt agacacttct gactgggaac    720
cactaactca tactaacaga ctaatggcaa tatacttaag cagtgtggct tctaagcttg    780
actttaccgg ggggccacta gcggggtgct tgtactttt tcaagtagaa tgtaacaaat    840
ttgaagaagg ctatcatatt catgtggtta ttgggggggcc agggttaaac cccagaaacc    900
tcacagtgtg tgtagagggg ttatttaata atgtacttta tcaccttgta actgaaaatg    960
taaagctaaa attttttgcca ggaatgacta caaaaggcaa atactttaga gatggagagc    1020
agtttataga aaactattta atgaaaaaaaa tacctttaaa tgttgtatgg tgtgttacta    1080
atattgatgg atatatagat acctgtattt ctgctacttt tagaagggga gcttgccatg    1140
ccaagaaacc ccgcattacc acagccataa atgacactag tagtgatgct ggggagtcta    1200
gcggcacagg ggcagaggtt gtgccaatta atgggaaggg aactaaggct agcataaagt    1260
ttcaaactat ggtaaactgg ttgtgtgaaa acagagtgtt tacagaggat aagtggaaac    1320
tagttgactt taaccagtac actttactaa gcagtagtca cagtggaagt tttcaaattc    1380
aaagtgcact aaaactagca atttataaag caactaattt agtgcctaca agcacatttc    1440
tattgcatac agactttgag caggttatgt gtattaaaga caataaaatt gttaaattgt    1500
tactttgtca aaactatgac cccctattag tggggcagca tgtgttaaag tggattgata    1560
aaaaatgtgg caagaaaaat acactgtggt tttatgggcc gccaagtaca ggaaaaacaa    1620
acttggcaat ggccattgct aaaagtgttc cagtatatgg catggttaac tggaataatg    1680
aaaactttcc atttaatgat gtagcaggga aaagcttggt ggtctgggat gaaggtatta    1740
ttaagtctac aattgtagaa gctgcaaaag ccatttttagg cgggcaaccc accagggtag    1800
atcaaaaaat gcgtggaagt gtagctgtgc ctggagtacc tgtggttata accagcaatg    1860
gtgacattac ttttgttgta agcgggaaca ctacaacaac tgtacatgct aaagccttaa    1920
aagagcgaat ggtaaagtta aactttactg taagatgcag ccctgacatg gggttactaa    1980
cagaggctga tgtacaacag tggcttacat ggtgtaatgc acaaagctgg gaccactatg    2040
aaaactgggc aataaactac acttttgatt tccctggaat taatgcagat gccctccacc    2100
cagacctcca aaccaccccca attgtcacag acaccagtat cagcagcagt ggtggtgaaa    2160
gctctgaaga actcagtgaa agcagctttt ttaacctcat caccccaggc gcctggaaca    2220
ctgaaacccc gcgctctagt acgcccatcc ccgggaccag ttcaggagaa tcatttgtcg    2280
gaagctcagt ttcctccgaa gttgtagctg catcgtggga agaagccttc tacacacctt    2340
tggcagacca gtttcgtgaa ctgttagttg gggttgatta tgtgtgggac ggtgtaaggg    2400
gtttacctgt gtgttgtgtg caacatatta acaatagtgg gggaggcttg ggactttgtc    2460
```

```
cccattgcat taatgtaggg gcttggtata atggatggaa atttcgagaa tttaccccag    2520
atttggtgcg gtgtagctgc catgtgggag cttctaatcc cttttctgtg ctaacctgca    2580
aaaaatgtgc ttacctgtct ggattgcaaa gctttgtaga ttatgagtaa agaaagtggc    2640
aaatggtggg aaagtgatga taaatttgct aaagctgtgt atcagcaatt tgtggaattt    2700
tatgaaaagg ttactggaac agacttagag cttattcaaa tattaaaaga tcactataat    2760
atttctttag ataatcccct agaaaaccca tcctctctgt ttgacttagt tgctcgtatt    2820
aaaaataacc ttaaaaactc tccagactta tatagtcatc attttcaaag tcatggacag    2880
ttatctgacc accccatgc cttatcatcc agtagcagtc atgcagaacc tagaggagaa     2940
aatgcagtat tatctagtga agacttacac aagcctgggc aagttagcgt acaactaccc    3000
ggtactaact atgttgggcc tggcaatgag ctacaagctg ggccccgca aagtgctgtt     3060 gacagtgctg caaggattca tgactttagg tatagccaac tggctaagtt gggaataaat    3120
ccatatactc attggactgt agcagatgaa gagcttttaa aaatataaa aaatgaaact     3180 gggtttcaag cacaagtagt aaaagactac tttactttaa aaggtgcagc tgcccctgtg    3240
gcccattttc aaggaagttt gccggaagtt cccgcttaca acgcctcaga aaaatacccca   3300 agcatgactt cagttaattc tgcagaagcc agcactggtg caggaggggg tggcagtaat    3360
cctgtcaaaa gcatgtggag tgaggggggcc acttttagtg ccaactctgt aacttgtaca   3420
ttttccagac agttttttaat tcctatgac ccagagcacc attataaggt gttttctccc    3480
gcagcaagca gctgccacaa tgccagtgga aaggaggcaa aggtttgcac aattagtccc    3540
ataatgggat actcaacccc atggagatat ttagatttta atgctttaaa tttattttt    3600 tcacctttag agtttcagca cttaattgaa aattatggaa gtatagctcc tgatgcttta    3660
actgtaacca tatcagaaat tgctgttaag gatgttacag acaaaactgg aggggggta    3720 caggttactg acagcactac agggcgccta tccatgttag tagaccatga atacaagtac    3780
ccatatgtgt taggacaagg tcaggatact ttagccccag aacttcctat ttgggtatac    3840
tttccccctc aatatgctta cttaacagta ggagatgtta acacacaagg aatctctgga    3900
gacagcaaaa aattagcaag tgaagaatca gcattttatg ttttggaaca cagttctttt    3960
cagcttttag gtacaggagg tacagcaact atgtcttata agtttcctcc agtgccccca    4020
gaaaatttag agggctgcag tcaacacttt tatgaaatgt acaatcccctt atacggatcc    4080 cgcttagggg ttcctgacac attaggaggt gacccaaaat ttagatcttt aacacatgaa    4140
gaccatgcaa ttcagcccca aaacttcatg ccagggccac tagtaaactc agtgtctaca    4200
aaggagggag acagctctaa tactggagct ggaaaagcct taacaggcct tagcacaggc    4260
acctctcaaa acactagaat atccttacgc cctgggccag tgtcacagcc ataccaccac    4320
tgggacacag ataaatatgt tccaggaata aatgccattt ctcatggtca gaccacttat    4380
ggtaacgctg aagacaaaga gtatcagcaa ggagtgggta gatttccaaa tgaaaaagaa    4440
cagctaaaac agttacaggg tttaaacatg cacacctatt tccccaataa aggaacccag    4500
caatatacag atcaaattga gcgcccccta atggtgggtt ctgtatggaa cagaagagcc    4560
cttcactatg aaagccagct gtggagtaaa attccaaatt tagatgacag ttttaaaact    4620
cagtttgcag ccttaggagg atgggggtttg catcagccac ctcctcaaat attttttaaaa  4680 atattaccac aaagtgggcc aattggaggt attaaatcaa tgggaattac taccttagtt    4740
cagtatgccg tgggaattat gacagtaact atgacattta aattgggggcc ccgtaaagct   4800 acgggacggt ggaatcctca acctggagta tatcccccgc acgcagcagg tcatttacca    4860
```

```
tatgtactat atgaccccac agctacagat gcaaaacaac accacaggca tggatacgaa    4920
aagcctgaag aattgtggac agccaaaagc cgtgtgcacc cattgtaaac actccccacc    4980
gtgccctcag ccaggatgcg taactaaacg cccaccagta ccacccagac tgtacctgcc    5040
ccctcctgta cctataagac agcctaacac aaaagatata gacaatgtag aatttaagta    5100
cttaaccaga tatgaacaac atgttattag aatgttaaga ttgtgtaata tgtatcaaaa    5160
tttagaaaaa taaacatttg ttgtggttaa aaaattatgt tgttgcgctt taaaaattta    5220
aaagaagaca ccaaatcaga tgccgccggt cgccgccggt aggcgggact tccggtacaa    5280
gatggcggac aattacgtca tttcctgtga cgtcatttcc tgtgacgtca cttccggtgg    5340
gcgggacttc cggaattagg gttggctctg gccagcgct tggggttgac gtgccactaa     5400
gacaagcggc gcgccgcttg tcttagtgtc aaggcaaccc caagcaagct ggcccagagc    5460
caaccctaat tccggaagtc ccgcccaccg gaagtgacgt cacaggaaat gacgtcacag    5520
gaaatgacgt aattgtccgc catcttgtac cggaagtccc gcctaccggc ggcgaccggc    5580
ggcatctgat ttgg                                                     5594

<210> SEQ ID NO 200
<211> LENGTH: 472
<212> TYPE: DNA
<213> ORGANISM: Artificial Sequence
<220> FEATURE:
<223> OTHER INFORMATION: Synthetic Oligomer

<400> SEQUENCE: 200
aaatattaaa agatcattat aatatttctt tagataatcc cctagaaaac ccatcctctc      60
tgtttgactt agttgctcgt attaaaaata accttaaaaa ctctccagac ttatatagtc     120
atcattttca aagtcatgga cagttatctg accaccccca tgccttatca tccagtagca     180
gtcatgcaga acctagagga gaagatgcag tattatctag tgaagactta cacaagcctg     240
ggcaagttag cgtacaacta cccggtacta actatgttgg gcctggcaat gagctacaag     300
ctgggccccc gcaaagtgct gttgacagtg ctgcaaggat tcatgacttt aggtatagcc     360
aactggctaa gttgggaata aatccatata ctcattggac tgtagcagat gaagagcttt     420
taaaaaatat aaaaaatgaa accgggtttc aagcacaagt agtaaaagac ta             472

<210> SEQ ID NO 201
<211> LENGTH: 471
<212> TYPE: DNA
<213> ORGANISM: Artificial Sequence
<220> FEATURE:
<223> OTHER INFORMATION: Synthetic Oligomer

<400> SEQUENCE: 201
aatattaaaa gatcattaca atatttcttt agataatccc ctagaaaacc catcttccct      60
gtttgactta gttgctcgta ttaaaagtaa tcttaaagac tctccagacc tatatagtca    120
tcattttcaa agtcatggac agttatctga ccaccccat gccttatcac ccagtagcag     180
tcatacagaa cctagaggag aaaatgcagt attatctagt gaagacttac acaagcctgg    240
gcaagttagc atacaactac ccggtactaa ctatgttggg cctggcaatg agctacaagc    300
tgggcccccg caaagtgctg tggacagtgc tgcaaggatt catgactta ggtatagcca    360 attggctaag ctgggaataa acccatatac ttattggact gtagcagatg aggaactgtt   420
aaaaaatata aaaaatgaaa ctgggtttca agcacaagca gtaaaagatt a             471
```

```
<210> SEQ ID NO 202
<211> LENGTH: 472
<212> TYPE: DNA
<213> ORGANISM: Artificial Sequence
<220> FEATURE:
<223> OTHER INFORMATION: Synthetic Oligomer

<400> SEQUENCE: 202
aaattttaaa agatcattac aacatttctt tagacaatcc tttagaaaac ccctcttctt    60
tatttgactt agttgctcgc attaaaagca atcttaaaaa ctctccagac ctatatagtc   120
atcattttca gagccatgga cagttatctg accaccccca ttccttatca cccagtaaca   180
gtagtacaga acctagagga gaaaatgcag tattatctag tgaagactta cacaagcctg   240
ggcaagttag catacaatta cccggtacta actatgttgg gcctggcaat gagctacaag   300
ctgggcctcc gcagaatgct gtggacagtg ctgcaaggat tcatgacttt aggtatagcc   360
aattggctaa gttgggaata aatccttata ctcattggac ggtagcagat gaggaattgt   420 taaaaatat aaaaaatgaa acagggtttc aagcacaagc agtaaaagac ta            472

<210> SEQ ID NO 203
<211> LENGTH: 1039
<212> TYPE: DNA
<213> ORGANISM: Artificial Sequence
<220> FEATURE:
<223> OTHER INFORMATION: Synthetic Oligomer

<400> SEQUENCE: 203
tttgtcggaa gcccagtttc ctccgaagtt gtagctgcat cgtgggaaga agccttctac    60
acacctttgg cagaccagtt tcgtgaactg ttagttgggg ttgattatgt gtgggacggt   120 gtaagggct tacctgtgtg ttgtgtgcaa catattaaca atagtggggg aggcttggga   180
ctttgtcccc attgcattaa tgtaggggct tggtataatg gatggaaatt tcgagaattt   240
actccagatt tggtgcgatg tagctgccat gtgggagctt ctaatccctt ttctgtgcta   300
acctgtaaaa aatgtgctta cctgtctgga ttgcaaagct ttgtagatta tgagtaaaga   360
aagtggcaaa tggtgggaaa gtaatgataa atttgctaaa gctgtgtatc agcaatttgt   420
ggaattttat gaaaaagtta ctggaacaga cttagagctt attcaaatat aaaagacca   480 ttataatatt tctttagata atcccctaga aaacccatcc tctctgtttg acttagttgc   540
tcgtattaaa aataaccta aaaactctcc agacttatat agtcatcatt ttcaaagtca   600
tggacagtta tctgaccacc cccatgcctt atcatccagt agcagtcatg cagaacctag   660
aggagaaaat gcagtattat ctagtgaaga cttacacaag cctgggcaag ttagcgtaca   720 actaccggt actaactatg ttgggcctgg caatgagcta caagctgggc cccgcaaag   780 tgctgttgac agtgctgcaa ggattcatga ctttaggtat agccaactgg ctaagttggg   840
aataaatcca tatctcatt ggactgtagc agatgaagag cttttaaaaa atataaaaaa   900
tgaaactggg tttcaagcac aagtagtaaa agactacttt actttaaaag gtgcagctgc   960
ccctgtggcc cattttcaag gaagtttgcc ggaagttccc gcttacaacg cctcagaaaa   1020
atacccaagc atgacttca                                                1039
```